(12) United States Patent
Miyashita et al.

(10) Patent No.: US 12,338,254 B2
(45) Date of Patent: Jun. 24, 2025

(54) ORGANIC COMPOUND AND ORGANIC LIGHT-EMITTING DEVICE

(71) Applicant: CANON KABUSHIKI KAISHA, Tokyo (JP)

(72) Inventors: Hirokazu Miyashita, Kanagawa (JP); Jun Kamatani, Tokyo (JP); Naoki Yamada, Tokyo (JP); Hiroki Ohrui, Tokyo (JP); Yosuke Nishide, Kanagawa (JP); Satoru Shiobara, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 741 days.

(21) Appl. No.: 17/667,419

(22) Filed: Feb. 8, 2022

(65) Prior Publication Data

US 2022/0259229 A1 Aug. 18, 2022

(30) Foreign Application Priority Data

Feb. 9, 2021 (JP) ................ 2021-018706

(51) Int. Cl.
| | |
|---|---|
| C07D 519/00 | (2006.01) |
| C07D 487/00 | (2006.01) |
| H10K 85/60 | (2023.01) |
| F21K 9/60 | (2016.01) |
| F21S 43/145 | (2018.01) |

(Continued)

(52) U.S. Cl.
CPC ......... *C07D 519/00* (2013.01); *C07D 487/00* (2013.01); *H10K 85/615* (2023.02); *H10K 85/6572* (2023.02); *H10K 85/6574* (2023.02); *F21K 9/60* (2016.08); *F21S 43/145* (2018.01); *F21Y 2115/15* (2016.08); *G03G 15/04054* (2013.01); *G03G 2215/0409* (2013.01); *G09F 9/335* (2021.05); *H04N 23/631* (2023.01); *H10K 50/11* (2023.02); *H10K 50/12* (2023.02); *H10K 2101/10* (2023.02); *H10K 2101/30* (2023.02); *H10K 2101/40* (2023.02)

(58) Field of Classification Search
None
See application file for complete search history.

(56) References Cited

FOREIGN PATENT DOCUMENTS

| | | |
|---|---|---|
| KR | 20120070468 A | 6/2012 |
| WO | 2017017205 A1 | 2/2017 |

*Primary Examiner* — Robert S Loewe
(74) *Attorney, Agent, or Firm* — Canon U.S.A., Inc. IP Division

(57) ABSTRACT

An organic compound represented by formula [1]:

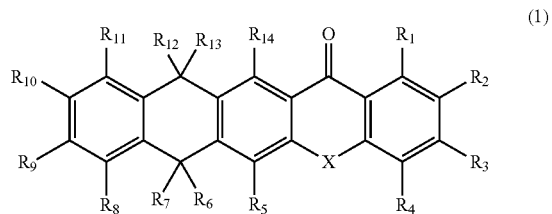

where $R_1$ to $R_{14}$ are each independently selected from the group consisting of a hydrogen atom and substituents, wherein at least one of $R_1$ to $R_4$ and $R_8$ to $R_{11}$ is an amino group or an amino group-containing group, and X is oxygen, sulfur, selenium, tellurium, or a $CR_{15}R_{16}$ group, wherein $R_{15}$ and $R_{16}$ are each independently selected from the group consisting of a hydrogen atom and substituents.

21 Claims, 9 Drawing Sheets

| COMPOUND | STRUCTURE | HOMO DISTRIBUTION | LUMO DISTRIBUTION | ENERGY DIFFERENCE BETWEEN $S_1$ AND $T_1$ (eV) |
|---|---|---|---|---|
| EXEMPLIFIED COMPOUND B-1 | 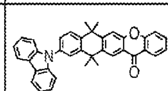 | | | 0.14 |
| EXEMPLIFIED COMPOUND B-2 | 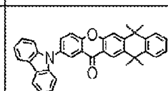 | | | 0.21 |
| EXEMPLIFIED COMPOUND D-1 | 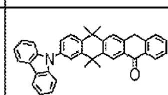 | | | 0.22 |
| COMPARATIVE COMPOUND 1 | 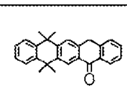 | | | 0.47 |

(51) Int. Cl.
*F21Y 115/15* (2016.01)
*G03G 15/04* (2006.01)
*G09F 9/33* (2006.01)
*H04N 23/63* (2023.01)
*H10K 50/11* (2023.01)
*H10K 50/12* (2023.01)
*H10K 101/10* (2023.01)
*H10K 101/30* (2023.01)
*H10K 101/40* (2023.01)

FIG. 1

| COMPOUND | STRUCTURE | HOMO DISTRIBUTION | LUMO DISTRIBUTION | ENERGY DIFFERENCE BETWEEN $S_1$ AND $T_1$ (eV) |
|---|---|---|---|---|
| EXEMPLIFIED COMPOUND B-1 | 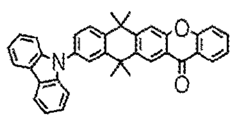 | | | 0.14 |
| EXEMPLIFIED COMPOUND B-2 | 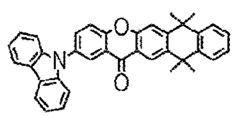 | | | 0.21 |
| EXEMPLIFIED COMPOUND D-1 | 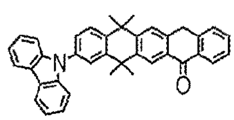 | | | 0.22 |
| COMPARATIVE COMPOUND 1 | 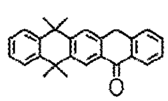 | | | 0.47 |

| COMPOUND | STRUCTURE | DIRECTION PERPENDICULAR TO MOLECULAR PLANE | DIRECTION PARALLEL TO MOLECULAR PLANE | DIHEDRAL ANGLE |
|---|---|---|---|---|
| EXEMPLIFIED COMPOUND B-3 | 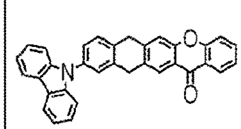 |  |  | 0.1° |
| COMPARATIVE COMPOUND 2 | 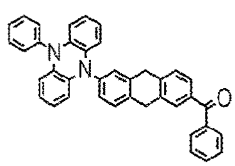 |  |  | 30.4° |

| COMPOUND | STRUCTURE | DIRECTION PERPENDICULAR TO MOLECULAR PLANE | DIRECTION PARALLEL TO MOLECULAR PLANE | DIHEDRAL ANGLE |
|---|---|---|---|---|
| EXEMPLIFIED COMPOUND B-1 | 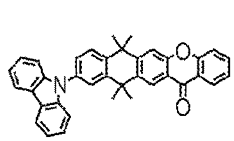 |  |  | 0.7° |
| EXEMPLIFIED COMPOUND B-3 | 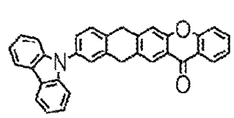 |  |  | 36.1° |

ORGANIC COMPOUND AND ORGANIC LIGHT-EMITTING DEVICE

BACKGROUND OF THE INVENTION

Field of the Invention

The present disclosure relates to an organic compound and an organic light-emitting device containing the organic compound.

Description of the Related Art

Organic light-emitting devices (hereinafter, also referred to as "organic electroluminescent devices" or "organic EL devices") are electronic devices each including a pair of electrodes and an organic compound layer disposed between these electrodes. The injection of electrons and holes from these pairs of electrodes generates excitons in the light-emitting organic compound in the organic compound layer, and when the excitons return to the ground state, the organic light-emitting device emits light.

Recently, organic light-emitting devices have made remarkable progress and have achieved low-driving voltage, various emission wavelengths, and fast response time. The use thereof has enabled the development of thinner and lighter light-emitting apparatuses.

Examples of high-efficiency light-emitting devices include devices containing high-efficiency materials, such as phosphorescent materials and delayed fluorescent materials.

Korean Patent Publication No. 2012-070468 describes compound A-1 below. International Publication No. 2017/017205 describes compound A-2 below.

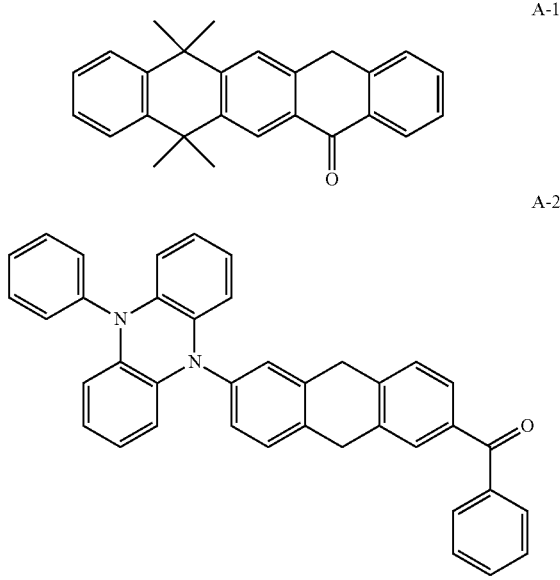

However, when compound A-1 described in Korean Patent Publication No. 2012-070468 is used for an organic light-emitting device, the device has a disadvantage in terms of luminous efficiency. When compound A-2 described in International Publication No. 2017/017205 is used for an organic light-emitting device, the device has a disadvantage in terms of driving durability.

SUMMARY OF THE INVENTION

The present disclosure has been accomplished in light of the foregoing disadvantages and provides an organic compound that has high chemical stability and that can be used as a material for an organic light-emitting device. The present disclosure also provides an organic light-emitting device having superior luminous efficiency and driving durability characteristics.

An organic compound according to an embodiment of the present disclosure is represented by formula [1]:

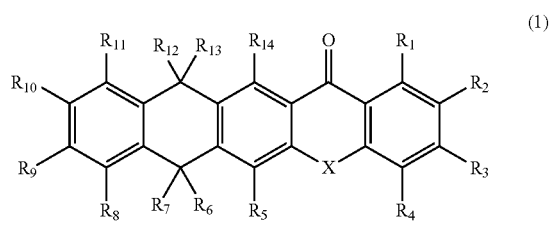

where in formula [1], $R_1$ to $R_{14}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group, $R_6$ and $R_7$ are optionally taken together to form a ring structure, $R_{12}$ and $R_{13}$ are optionally taken together to form a ring structure, wherein at least one of $R_1$ to $R_4$ and $R_8$ to $R_{11}$ is a substituted or unsubstituted amino group or a group containing a substituted or unsubstituted amino group, and groups bonded to a nitrogen atom of a substituted or unsubstituted amino group are optionally taken together to form a ring structure, and X is oxygen, sulfur, selenium, tellurium, or a $CR_{15}R_{16}$ group, wherein $R_{15}$ and $R_{16}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group.

Further features of the present disclosure will become apparent from the following description of exemplary embodiments with reference to the attached drawings.

BRIEF DESCRIPTION OF THE DRAWINGS

FIG. 1 illustrates electron orbital distributions of highest occupied molecular orbitals (HOMOs) and lowest unoccupied molecular orbitals (LUMOs).

DESCRIPTION OF THE EMBODIMENTS

Organic Compound

Figure 2:
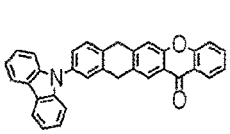
FIG. 2 illustrates the flatness of molecules.
Figure 2:
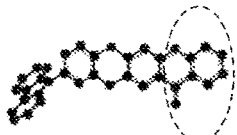
Figure 2:
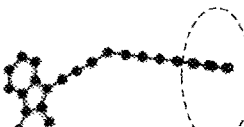
Figure 2:
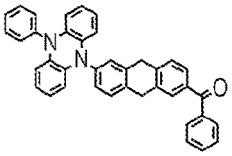
Figure 2:
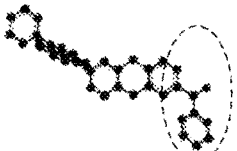
Figure 2:
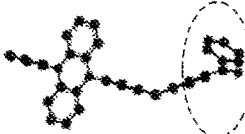

An organic compound according to an embodiment will be described. The organic compound according to this embodiment is represented by formula [1] below.

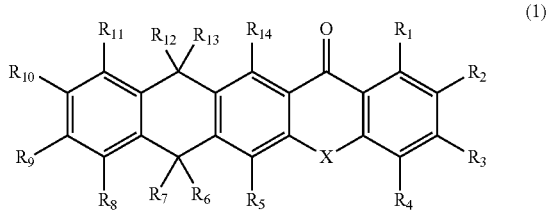

(1)

$R_1$ to $R_{14}$ $R_1$ to $R_{14}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group. $R_6$ and $R_7$ may be taken together to form a ring structure, and $R_{12}$ and $R_{13}$ may be taken together to form a ring structure. At least one of $R_1$ to $R_4$ and $R_8$ to $R_{11}$ is a substituted or unsubstituted amino group or a group containing a substituted or unsubstituted amino group. Groups bonded to a nitrogen atom of a substituted or unsubstituted amino group may be taken together to form a ring structure.

Non-limiting examples of the halogen atom include fluorine, chlorine, bromine, and iodine.

Non-limiting examples of the alkyl group include a methyl group, an ethyl group, a n-propyl group, an isopropyl group, a n-butyl group, a tert-butyl group, a sec-butyl group, an octyl group, a cyclohexyl group, a 1-adamantyl group, and a 2-adamantyl group. As the alkyl group, an alkyl group having 1 to 10 carbon atoms can be used.

Non-limiting examples of the alkoxy group include a methoxy group, an ethoxy group, a propoxy group, a 2-ethyloctyloxy group, and a benzyloxy group. As the alkoxy group, an alkoxy group having 1 to 10 carbon atoms can be used.

Non-limiting examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, ab N-mesityl-N-phenylamino group, an N,N-dimesitylamino group, an N-phenyl-N-(4-tert-butylphenyl)amino group, an N-phenyl-N-(4-trifluoromethylphenyl)amino group, an N-piperidyl group, a carbazolyl group, and an acridyl group.

Further examples of the amino group include amino groups each having any of structures illustrated below. In the following structural formulae, each * represents a binding position.

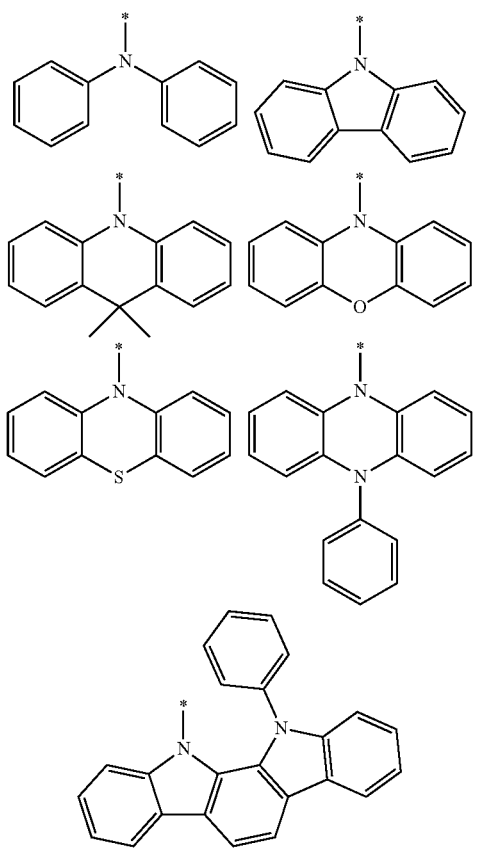

-continued
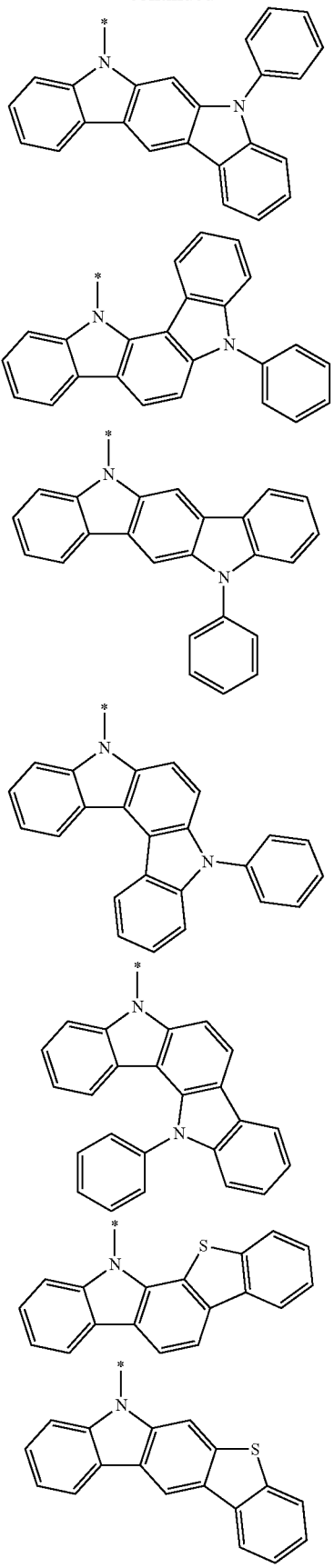
-continued
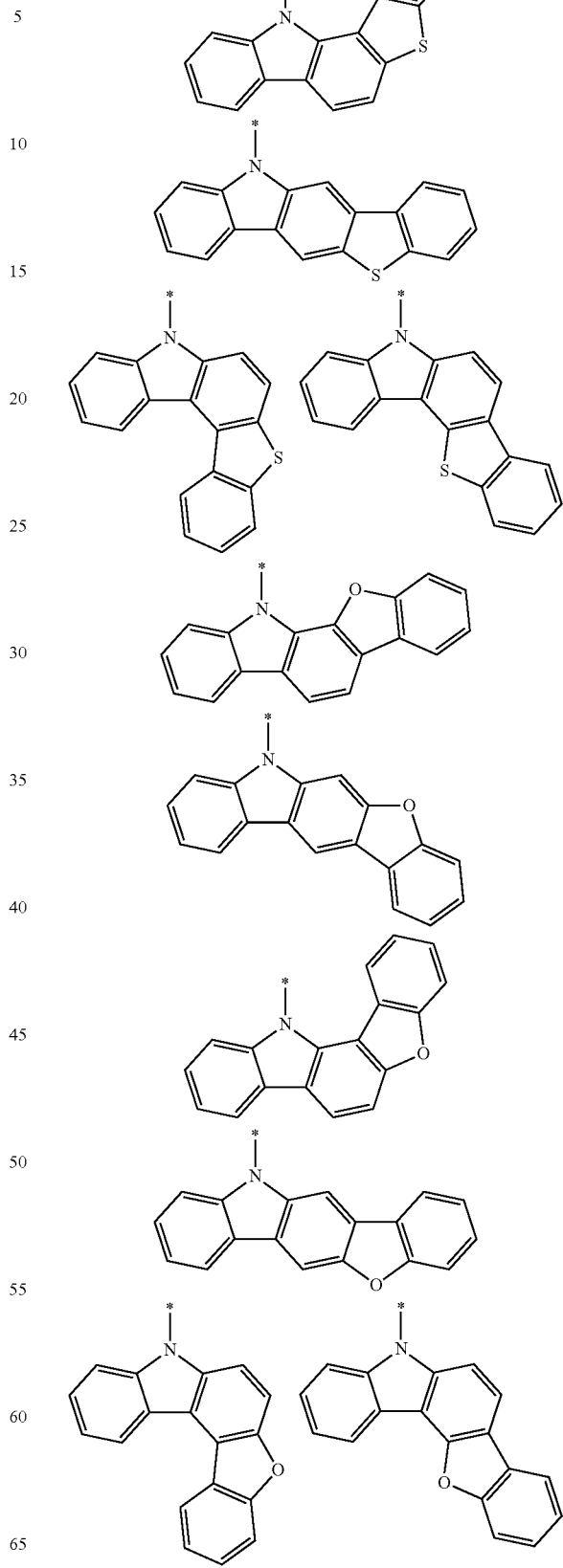

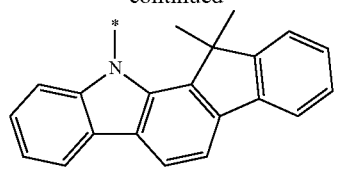
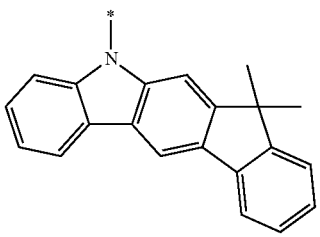
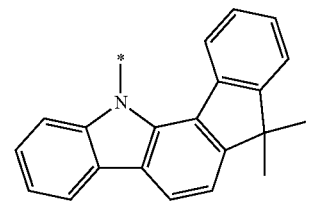
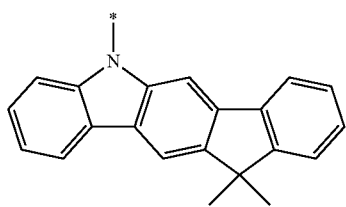
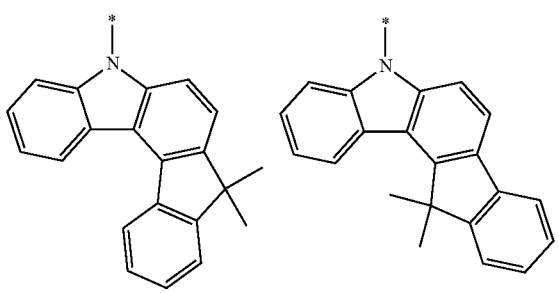
Among these, an amino group having any of the following structures can be used. In the following structural formulae, each * represents a binding position.
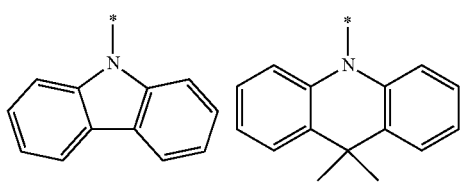
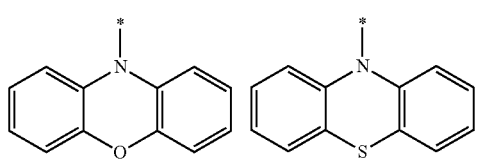
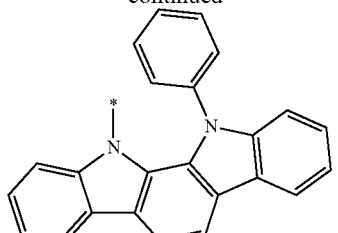
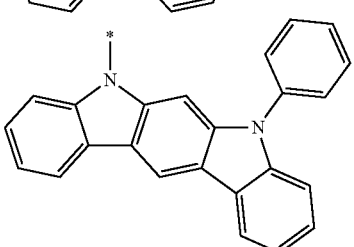
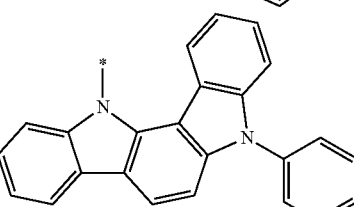
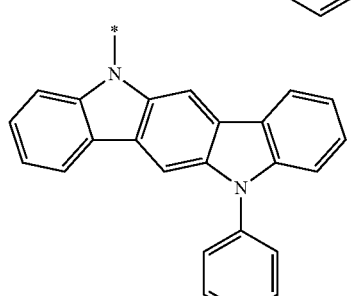
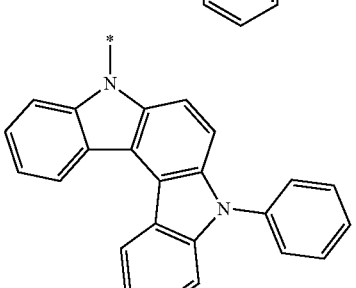
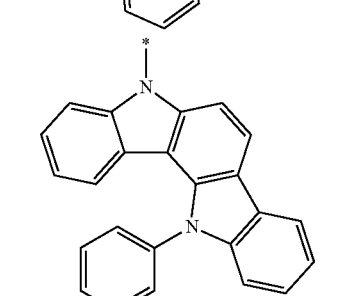
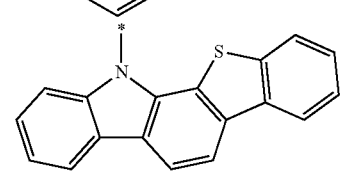

-continued

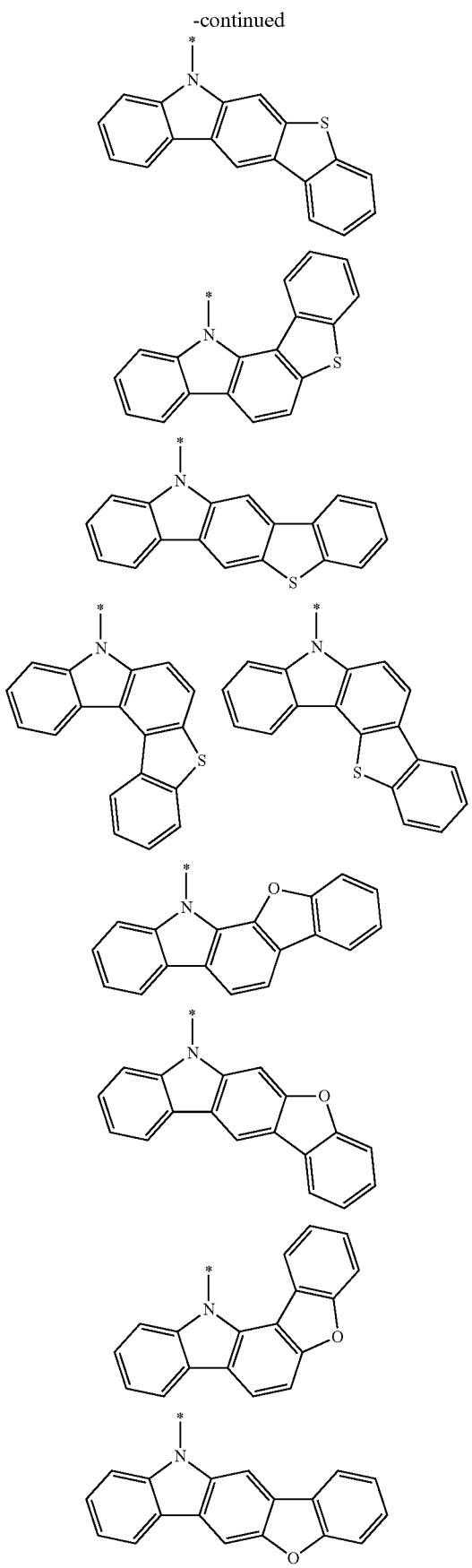

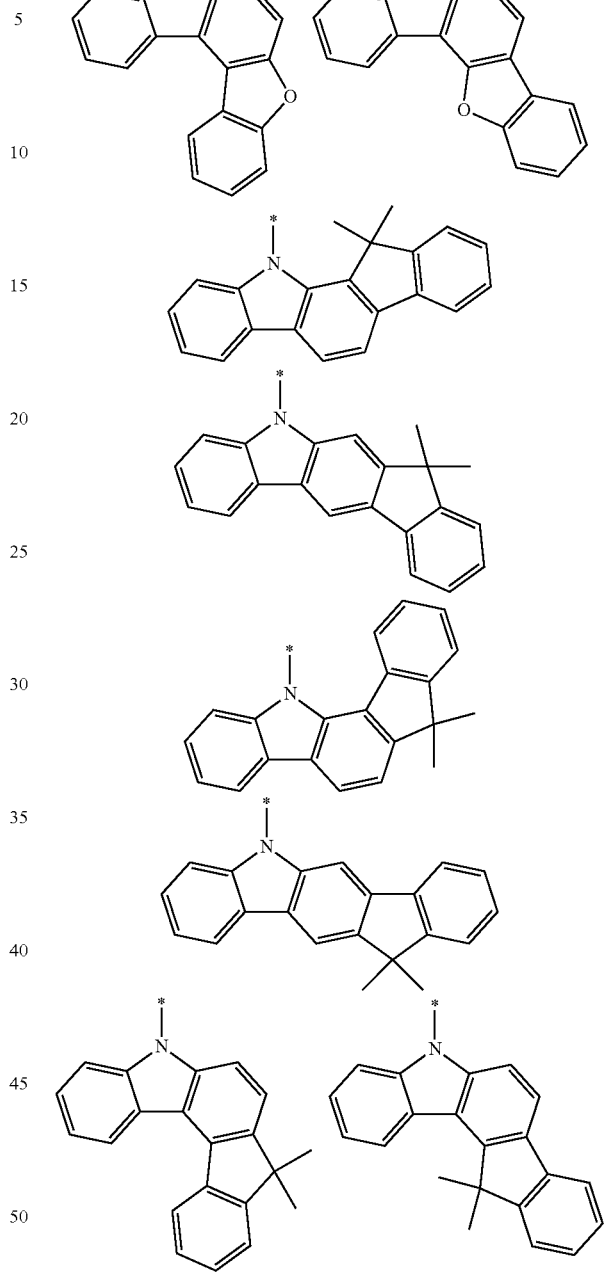

Non-limiting examples of the aromatic hydrocarbon group include a phenyl group, a naphthyl group, an indenyl group, a biphenyl group, a terphenyl group, a fluorenyl group, a phenanthryl group, a triphenylenyl group, a pyrenyl group, an anthracenyl group, a perylenyl group, a chrysenyl group, and a fluoranthenyl group. As the aromatic hydrocarbon group, an aromatic hydrocarbon group having 6 to 60 carbon atoms can be used.

Non-limiting examples of the heterocyclic group include a pyridyl group, a pyrimidinyl group, a pyrazinyl group, a triazinyl group, a benzofuranyl group, a benzothiophenyl group, a dibenzofuranyl group, a dibenzothiophenyl group, an oxazolyl group, an oxadiazolyl group, a thiazolyl group, a thiadiazolyl group, a carbazolyl group, an acridinyl group, and a phenanthrolinyl group. As the heterocyclic group, a heterocyclic group having 3 to 60 carbon atoms can be used.

Non-limiting examples of the aryloxy group include a phenoxy group and a naphthoxy group.

Non-limiting examples of the heteroaryloxy group include a furanyloxy group and a thienyloxy group.

Non-limiting examples of the silyl group include a trimethylsilyl group and a triphenylsilyl group.

Non-limiting examples of substituents that may be further contained in the alkyl group, the alkoxy group, the amino group, the aromatic hydrocarbon group, the heterocyclic group, the aryloxy group, and the heteroaryloxy group include alkyl groups, such as a methyl group, an ethyl group, a n-propyl group, an isopropyl group, a n-butyl group, and a tert-butyl group; aralkyl groups, such as a benzyl group; aromatic hydrocarbon groups, such as a phenyl group, a biphenyl group, and a naphthyl group; heterocyclic groups, such as a pyridyl group, a pyrrolyl group, a pyrazinyl group, and a triazinyl group; amino groups, such as a dimethylamino group, a diethylamino group, a dibenzylamino group, a diphenylamino group, and a ditolylamino group; alkoxy groups, such as a methoxy group, an ethoxy group, and a propoxy group; aryloxy groups, such as a phenoxy group; halogen atoms, such as fluorine, chlorine, bromine, and iodine atoms; and a cyano group. Groups bonded to the nitrogen atoms of amino groups that may be further contained may be taken together to form ring structures.

Each of $R_6$, $R_7$, $R_{12}$, and $R_{13}$ may not be a hydrogen atom. At least one of $R_8$ to $R_{11}$ can be a substituted or unsubstituted amino group or a group containing a substituted or unsubstituted amino group, or can be a group containing a substituted or unsubstituted amino group.

$R_1$ to $R_5$ and $R_{14}$ can each be a hydrogen atom, a substituted or unsubstituted alkyl group, a phenyl group, a biphenyl group, a naphthyl group, a pyridyl group, a pyrazinyl group, a triazinyl group, fluorine, or a cyano group.
X X is oxygen, sulfur, selenium, tellurium, or a $CR_{15}R_{16}$ group. X can be selected from oxygen and sulfur.

$R_{15}$ and $R_{16}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group.

Specific examples of the halogen atom, the alkyl group, the alkoxy group, the amino group, the aromatic hydrocarbon group, the heterocyclic group, the aryloxy group, the heteroaryloxy group, and the silyl group that are represented by $R_{15}$ and $R_{16}$ include, but are not limited to, the same as those described for $R_1$ to $R_{14}$. As the alkyl group, an alkyl group having 1 to 10 carbon atoms can be used. As the alkoxy group, an alkoxy group having 1 to 10 carbon atoms can be used. As the aromatic hydrocarbon group, an aromatic hydrocarbon group having 6 to 60 carbon atoms can be used. As the heterocyclic group, a heterocyclic group having 3 to 60 carbon atoms can be used. Specific examples of substituents that may further be contained in the alkyl group, the alkoxy group, the amino group, the aromatic hydrocarbon group, the heterocyclic group, the aryloxy group, and the heteroaryloxy group include, but are not limited to, the same as those described for $R_1$ to $R_{14}$.

A method for synthesizing an organic compound according to this embodiment of the present disclosure will be described below. The organic compound according to the embodiment of the present disclosure is synthesized, for example, by a reaction scheme described below.

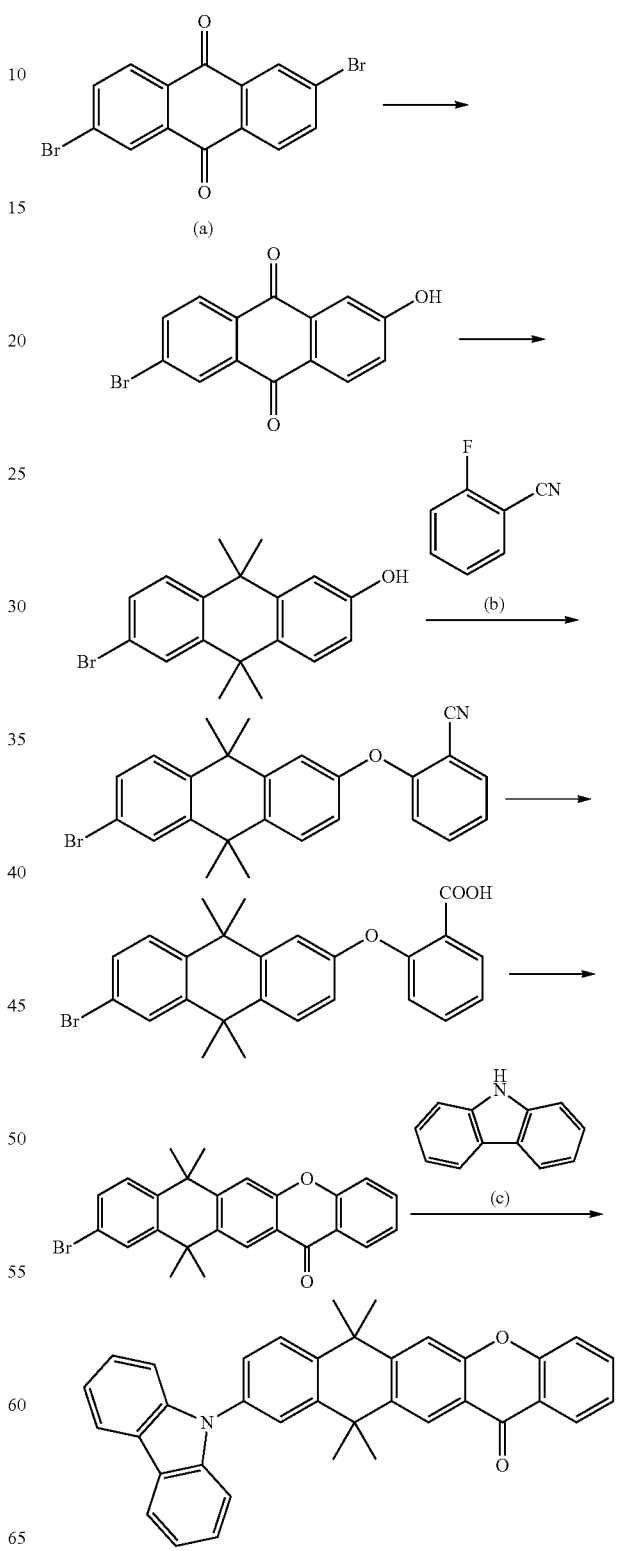

Here, the compound represented by formula [1] can be synthesized by appropriately changing compounds (a) to (c). The synthesis method is not limited thereto.

The organic compound according to the embodiment has features described below. Thus, the use of the organic compound according to the embodiment for an organic light-emitting device allows the organic light-emitting device to have high luminous efficiency and superior driving durability characteristics. A basic skeleton in this embodiment is a skeleton in which in the compound represented by formula [1], $R_1$ to $R_{14}$ are each a hydrogen atom, and in addition, when X is a $CR_{12}R_{13}$ group, $R_{12}$ and $R_{13}$ are each a hydrogen atom.

(1) The organic compound has a small energy gap between $S_1$ and $T_1$ because it has, as a basic skeleton, a structure in which an electron-withdrawing carbonyl group is bonded to the tetrahydroanthracene skeleton while incorporated into a ring structure and in which at least one of $R_1$ to $R_4$ and $R_8$ to $R_{11}$ is an electron-donating amino group or a group containing an electron-donating amino group.

(2) The organic compound has a deep highest occupied molecular orbital (HOMO) level because it has, as the basic skeleton, the structure in which the electron-withdrawing carbonyl group is bonded to the tetrahydroanthracene skeleton while incorporated into the ring structure.

(3) The organic compound has a high degree of flatness and superior carrier transport ability because it has, as the basic skeleton, the structure in which the electron-withdrawing carbonyl group is bonded to the tetrahydroanthracene skeleton while incorporated into the ring structure.

Features (1) to (3) mentioned above will be described below.

(1) The organic compound has a small energy gap between $S_1$ and $T_1$ because it has, as a basic skeleton, a structure in which an electron-withdrawing carbonyl group is bonded to the tetrahydroanthracene skeleton while incorporated into a ring structure and in which at least one of $R_1$ to $R_4$ and $R_8$ to $R_{11}$ is an electron-donating amino group or a group containing an electron-donating amino group.

The inventors have focused on electron distributions of the highest occupied molecular orbital (HOMO) and the lowest unoccupied molecular orbital (LUMO) of the compound represented by formula [1] in creating the organic compound.

As illustrated in FIG. 1, in each of exemplified compounds B-1, B-2, and D-1 according to the embodiment, a moiety occupying the electron orbital distribution of the HOMO and a moiety occupying the electron orbital distribution of the LUMO are separated. That is, only a small moiety occupies both HOMO and LUMO.

This leads to a small overlap integral and a small energy difference between the excited singlet state ($S_1$) and the excited triplet state ($T_1$). Specifically, the energy gaps between $S_1$ and $T_1$ of B-1, B-2, and D-1 are as small as 0.14 eV, 0.21 eV, and 0.22 eV, respectively. In contrast, the energy gap between $S_1$ and $T_1$ of comparative compound 1 is as large as 0.47 eV.

The above feature is the effect due to the fact that the organic compound has, as the basic skeleton, the structure in which the electron-withdrawing carbonyl group is bonded to the tetrahydroanthracene skeleton while incorporated into the ring structure and in which at least one of $R_1$ to $R_4$ and $R_8$ to $R_{11}$ is an electron-donating amino group or a group containing an electron-donating amino group. Regarding a structure with no amino group, such as comparative compound 1, there is a large overlap between a moiety occupying the electron orbital distribution of the HOMO and a moiety occupying the electron orbital distribution of the LUMO. This results in a large energy gap between $S_1$ and $T_1$. Comparative compound 1 is compound A-1 described in Korean Patent Publication No. 2012-070468.

The above calculation results were visualized using molecular orbital calculations. As the molecular orbital calculation method, the density functional theory (DFT), which is widely used at present, was used with the B3LYP functional and 6-31G* as the basis function. The molecular orbital calculation method was performed using Gaussian 09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010), which is widely used at present.

As described above, the compound according to the embodiment is characterized by having a small energy difference between $S_1$ and $T_1$. When the compound according to the embodiment is used in the light-emitting layer of an organic light-emitting device, it is possible to provide the device with high luminous efficiency. The reason for this is as follows: For excitons consisting of singlet and triplet excitons in a ratio of 1:3, the triplet excitons, which undergo thermal deactivation normally, can be used for delayed fluorescence from the excited singlet state due to the small energy difference between $S_1$ and $T_1$. To convert the triplet excitons into the excited singlet state, a smaller energy difference between $S_1$ and $T_1$ is advantageous because of a smaller energy barrier. The compound according to the embodiment has a small energy difference between $S_1$ and $T_1$, easily converts the triplet excitons into the excited singlet state, and thus can provide a device having high luminous efficiency.

(2) The organic compound has a deep highest occupied molecular orbital (HOMO) level because it has, as the basic skeleton, the structure in which the electron-withdrawing carbonyl group is bonded to the tetrahydroanthracene skeleton while incorporated into the ring structure.

The compound according to the embodiment has a fused polycyclic structure in which the electron-withdrawing carbonyl group is bonded to the tetrahydroanthracene skeleton while incorporated into the ring structure. The presence of the fused polycyclic structure as an electron-withdrawing moiety results in deeper HOMO and LUMO levels (farther from the vacuum level).

Here, a material having a deep HOMO level is a material that is not easily oxidized, in other words, a material having high oxidation stability. Thus, the material itself is less susceptible to deterioration by oxygen and moisture. Organic light-emitting devices are commonly susceptible to deterioration by oxygen and moisture. The material having high oxidation stability can be used for organic light-emitting devices.

Table 1 indicates a comparison of the HOMO energy levels of the compounds B-1 and B-2 according to the embodiment with comparative compound 2. Comparative compound 2 is the compound A-2 described in International Publication No. 2017/017205. As described in Table 1, the HOMO levels of the compounds according to the embodiment are as deep as −6.19 eV and −5.36 eV (far from the vacuum level). Thus, the compound can be said to be a material having high oxidation stability. This is presumably because the compound has a structure in which the electron-withdrawing carbonyl group is bonded while incorporated into the ring structure. In contrast, the HOMO level of comparative compound 2 is as shallow as −4.10 eV, and thus comparative compound 2 is a material having low oxidation stability. Comparative compound 2 also has an electron-withdrawing carbonyl group that is not incorporated into a ring structure; thus, the HOMO energy is considered to be shallow.

As described above, the use of the compound, having superior oxidation stability, according to the embodiment for an organic light-emitting device results in superior driving durability.

The compound according to the embodiment has the fused polycyclic structure in which five 6-membered rings are fused in a plane while the electron-withdrawing carbonyl group is bonded to the tetrahydroanthracene skeleton and incorporated into the ring structure. Thus, the moieties of this fused polycyclic structure tend to overlap with each other.

Here, as described in feature (1) above, the LUMO distribution of the compound according to the embodiment is localized to the fused polycyclic structure, which is the structure in which the electron-withdrawing carbonyl group is bonded to the tetrahydroanthracene skeleton while incorporated into the ring structure.

Typically, in organic light-emitting devices, hole carriers are transported by hopping conduction through HOMOs of organic materials, and electron carriers are transported by hopping conduction through LUMOs thereof. In the compound according to the embodiment, as illustrated in FIG. 1, the LUMO portions are located in the fused polycyclic structures each having a high degree of flatness; thus, the LUMOs overlap strongly with each other to facilitate the

TABLE 1

| Compound | Structure | HOMO(eV) |
|---|---|---|
| Exemplified compound B-1 | 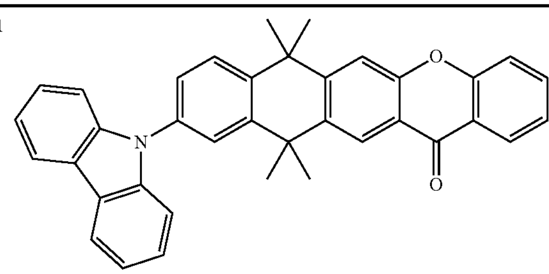 | −6.19 |
| Exemplified compound B-2 | 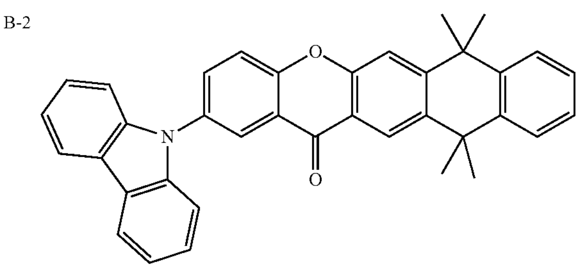 | −5.36 |
| Comparative compound 2 | 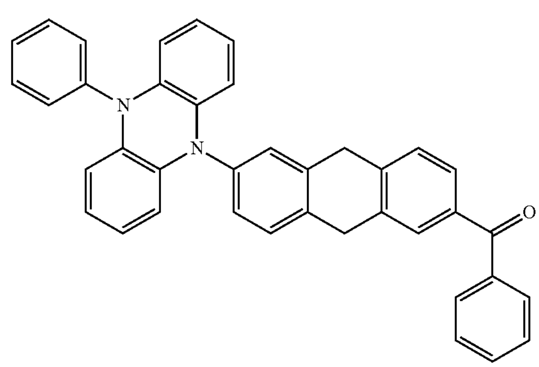 [SMILES: O=C(c1ccccc1)c1ccc2c(c1)Cc1ccc(N3c4ccccc4N(c4ccccc4)c4ccccc43)cc1C2] | −4.10 |

(3) The organic compound has a high degree of flatness and superior carrier transport ability because it has, as the basic skeleton, the structure in which the electron-withdrawing carbonyl group is bonded to the tetrahydroanthracene skeleton while incorporated into the ring structure.

hopping conduction of electron carriers through the LUMOs. That is, the compound according to the embodiment is a material having superior carrier transport ability. The use of the compound for an organic light-emitting device enables the device to be driven at a low voltage, and to have superior durability characteristics because of reductions in unnecessary carrier trapping and charge concentration.

FIG. 2 indicates a comparison of the compound B-3 according to the embodiment and comparative compound 2 in terms of the flatness of the carbonyl group with the benzene ring attached thereto (regions surrounded by dotted lines in FIG. 2). As described in FIG. 2, the compound according to the embodiment has a high degree of flatness in the fused polycyclic structure where the LUMO is localized, and the dihedral angle is as small as 0.1°. Thus, this compound can be said to be a material having superior carrier transport ability. The dihedral angle of comparative compound 2 is as large as 30.4°, thus resulting in a low degree of flatness. This results in a large intermolecular distance at the LUMO portions and thus low carrier transport ability.

As described above, the use of the compound, having superior carrier transport ability, according to the embodiment for an organic light-emitting device results in superior driving durability.

The organic compound can further satisfy the conditions (4) to (7) described below.

(4) Each of $R_6$, $R_7$, $R_{12}$, and $R_{13}$ is not a hydrogen atom.

This is because, when this condition is satisfied, the flatness of the fused polycyclic structure containing the electron-withdrawing carbonyl group is improved. This facilitates the overlap between the moieties of the fused polycyclic structures to improve the carrier transport ability of the compound according to the embodiment as described in feature (3) above.

Figure 3:
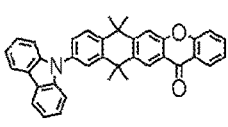
FIG. 3 illustrates the flatness of molecules.
Figure 3:
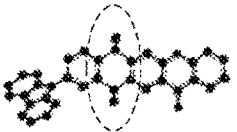
Figure 3:
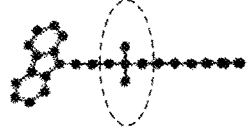
Figure 3:
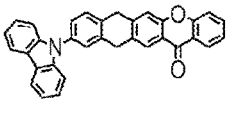
Figure 3:
Figure 3:

FIG. 3 illustrates a comparison of the compounds B-1 and B-3 according to the embodiment in terms of the flatness at the benzene ring of the tetrahydroanthracene skeleton (regions surrounded by dotted lines in FIG. 3). As described in FIG. 3, the dihedral angles of the compounds B-1 and B-3 are 0.7° and 36.1°, respectively. This indicates that the compound B-1 has a higher degree of flatness than the compound B-3 and thus is a material having superior carrier transport ability.

(5) At least one of $R_8$ to $R_{11}$ is an amino group or an amino group-containing group.

This is because when this condition is satisfied, the distance between the electron-withdrawing carbonyl group and the electron-donating amino group in the basic skeleton is increased to improve the separation between the electron orbital distributions of the HOMO and the LUMO described in feature (1) above.

This results in a smaller energy gap between $S_1$ and $T_1$. Specifically, as described in FIG. 1, the energy gaps between the $S_1$ and $T_1$ of exemplified compounds B-1 and B-2 are 0.14 eV and 0.21 eV, respectively. This indicates that the energy gap between $S_1$ and $T_1$ is smaller in exemplified compound B-1, in which any of $R_8$ to $R_{11}$ is an amino group, than exemplified compound B-2, in which any of $R_1$ to $R_4$ is an amino group. This is advantageous for reverse inter-system crossing and increases delayed fluorescence; thus, it is possible to provide a device having high luminous efficiency.

In addition, when this condition is satisfied, the HOMO energy is deeper (farther from the vacuum level). Specifically, as described in Table 1, the HOMO energies of exemplified compounds B-1 and B-2 are −6.19 eV and −5.36 eV, respectively. This indicates that the HOMO energy of exemplified compound B-1, in which any of $R_8$ to $R_{11}$ is an amino group, is deeper than that of exemplified compound B-2, in which any of $R_1$ to $R_4$ is an amino group. As described in feature (2) above, the material has high oxidation stability; thus, it is possible to provide a device having superior driving durability.

(6) At least one of $R_8$ to $R_{11}$ is an amino group having any of structures described below, where each * represents a binding position.

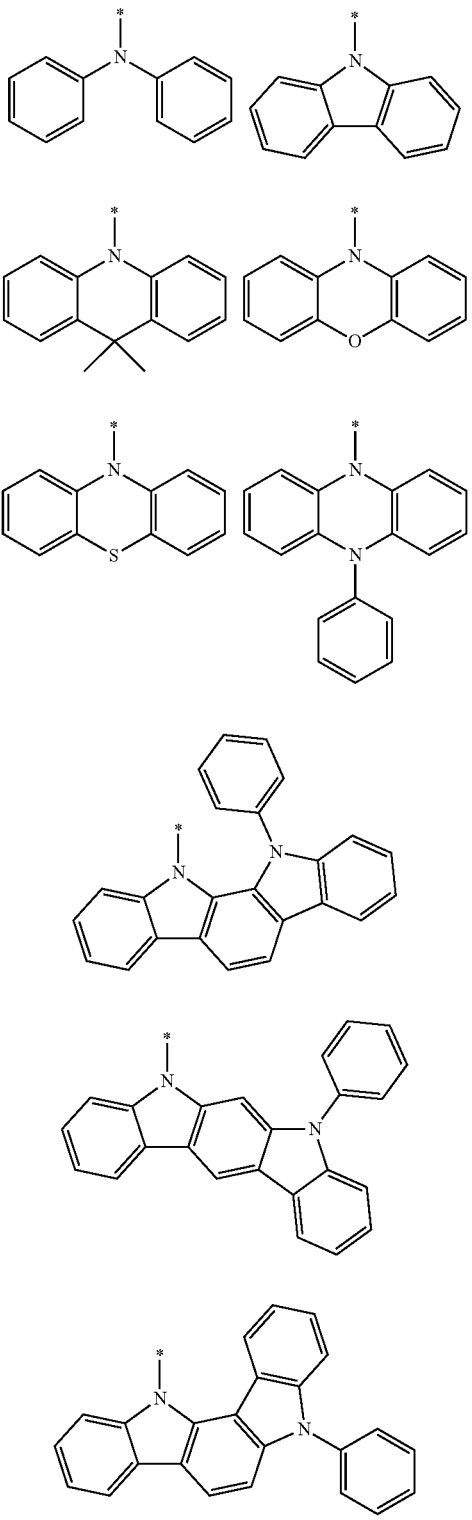

-continued
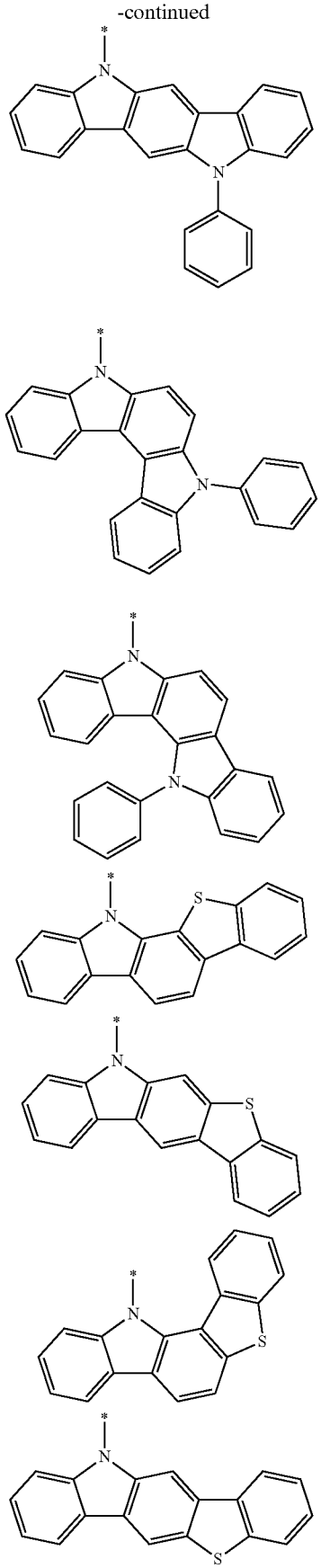
-continued
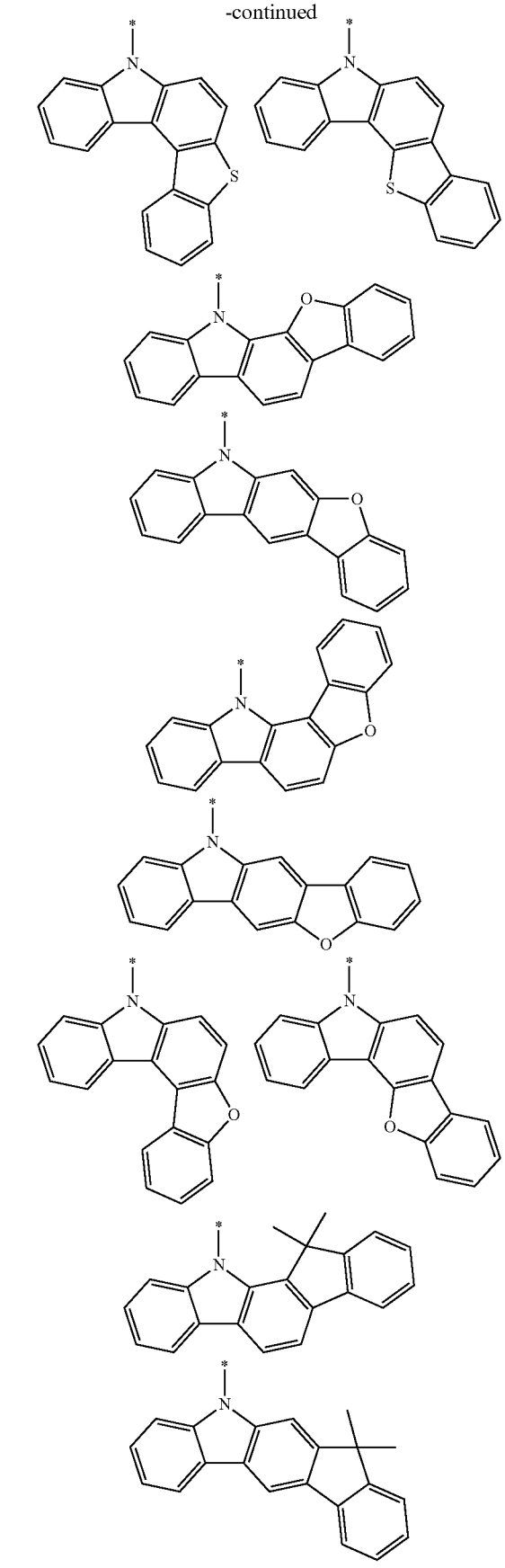

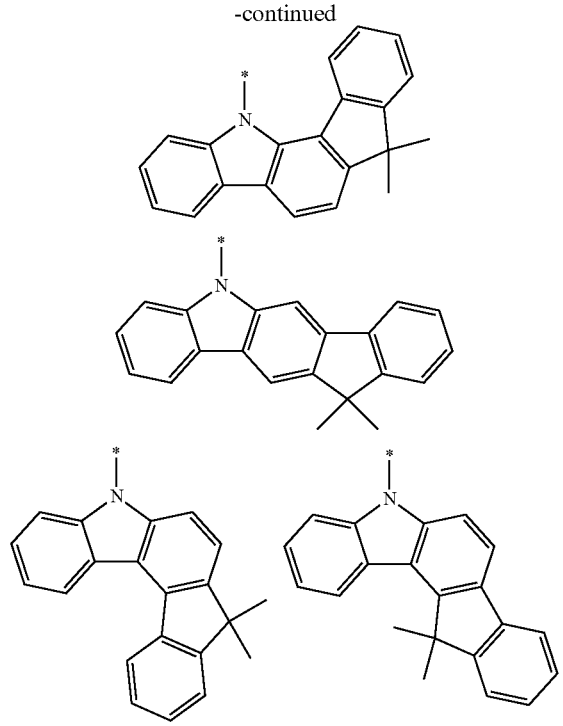

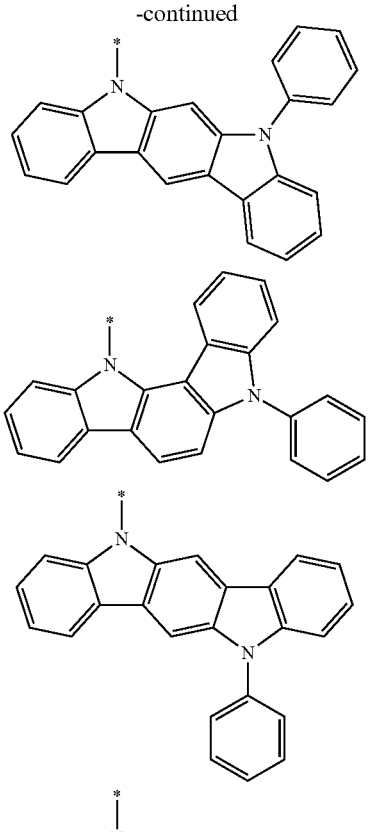

This is because when this condition is satisfied, the molecular flatness of the amino group where the HOMO is localized is improved, and thus the hole transport ability based on hopping conduction through the HOMO is improved, as described in feature (3) above. Accordingly, the material has a superior ability to transport both hole and electron carriers and thus advantageously improves the driving voltage and the driving durability of an organic light-emitting device.

At least one of $R_8$ to $R_{11}$ can be an amino group having any of the following structures, where each * represents a binding position.

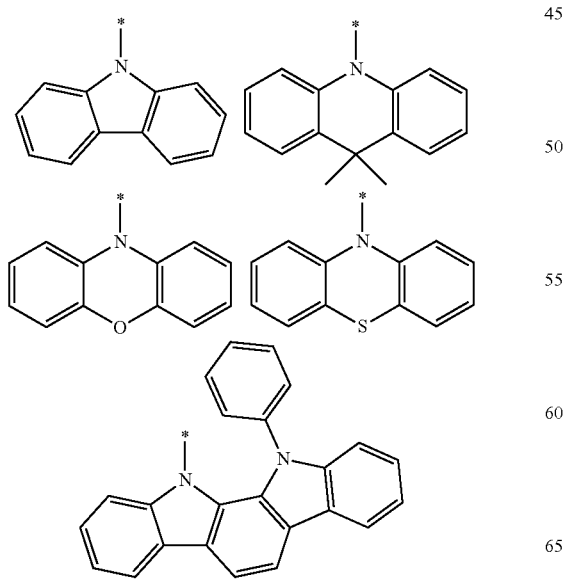

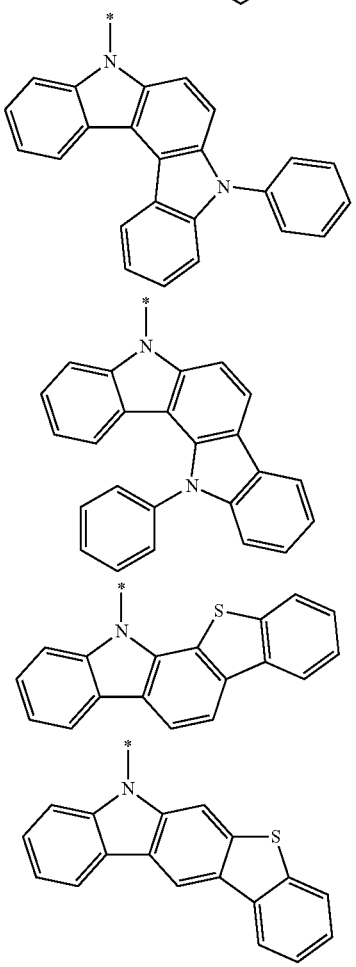

-continued

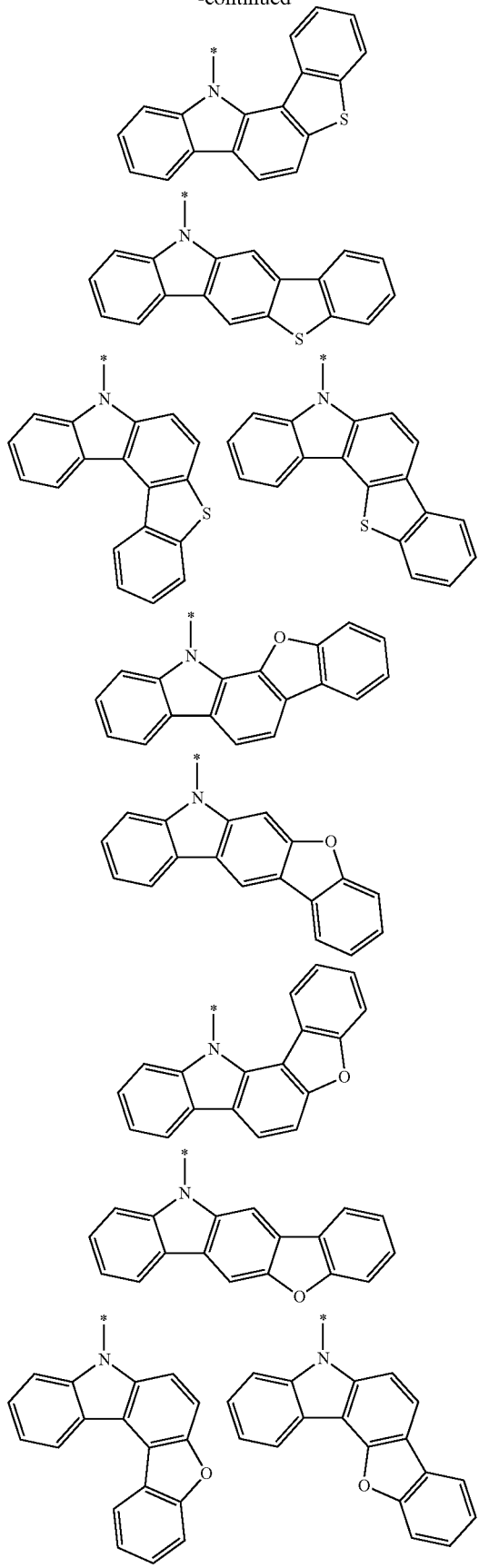

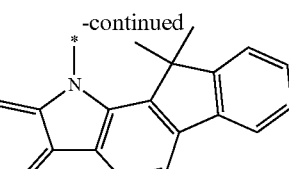
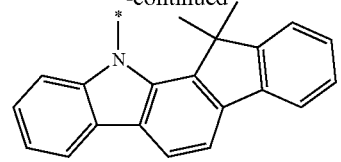
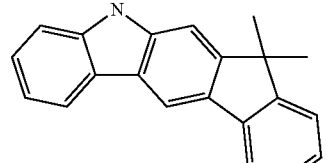
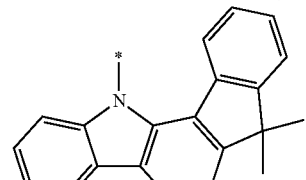
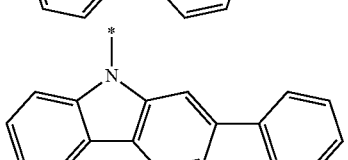
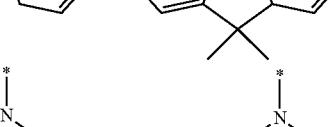
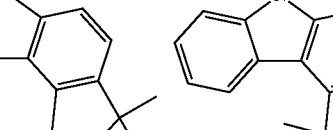
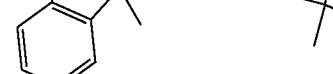

(7) X is selected from oxygen and sulfur.

When this condition is satisfied, the energy gap between $S_1$ and $T_1$ is small. As described in feature (1) above, this is advantageous for reverse intersystem crossing and increases delayed fluorescence; thus, it is possible to provide a device having high luminous efficiency.

Specifically, as described in FIG. 1, the energy gaps between $S_1$ and $T_1$ of exemplified compounds B-1 and D-1 are 0.14 eV and 0.22 eV, respectively. This indicates that the energy gap between $S_1$ and $T_1$ is smaller in exemplified compound B-1, in which X is oxygen, than in exemplified compound D-1, in which X is $C(Me)_2$. This is advantageous for reverse intersystem crossing and increases delayed fluorescence, which is advantageous for higher efficiency of an organic light-emitting device.

Furthermore, the compound according to the embodiment can be used in the light-emitting layer of an organic light-emitting device. In this case, the compound has the following features.

(8) The compound according to the embodiment is mixed with a host material in the light-emitting layer to facilitate exciton recombination of the compound according to the embodiment, thereby providing the light-emitting device with high efficiency.

(9) The mixture of the compound according to the embodiment and the host material in the light-emitting layer and the presence of a light-emitting material provide the light-emitting device with high efficiency and high color purity.

(10) The use of a hydrocarbon compound as the light-emitting material provides the light-emitting device with high efficiency and good durability characteristics.

Features (8) to (10) above will be described below.

(8) The compound according to the embodiment is mixed with a host material in the light-emitting layer to facilitate exciton recombination of the compound according to the embodiment, thereby providing the light-emitting device with high efficiency.

The compound according to the embodiment contains an electron-withdrawing carbonyl group and an electron-donating amino group. Thus, when the compound according to the embodiment is mixed with the host material in the light-emitting layer of the organic light-emitting device, the LUMO of the compound according to the embodiment is at a lower level (farther from the vacuum level) than the host material, and the HOMO of the compound according to the embodiment is at a higher level (closer to the vacuum level) than the host material.

Accordingly, in the light-emitting layer, electrons and holes fed from the transport layers are trapped by the compound according to the embodiment, and exciton recombination occurs. As described in feature (1) above, the compound according to the embodiment has a small energy difference between $S_1$ and $T_1$, can efficiently produce delayed fluorescence in the light-emitting layer, and can use a larger number of triplet excitons for light emission. This effect is especially significant when the host material is a hydrocarbon compound. The reason for this is that the larger energy differences between the HOMO and LUMO of the host and those of the compound according to the embodiment leads to easier trapping of electrons and holes. The hydrocarbon compound is a compound that consists of only carbon and hydrogen.

(9) The mixture of the compound according to the embodiment and the host material in the light-emitting layer and the presence of a light-emitting material provide the light-emitting device with high efficiency and high color purity.

A light-emitting device having even higher efficiency and color purity is provided by mixing the compound according to the embodiment with the host material in the light-emitting layer and doping the light-emitting layer with a light-emitting material having a high emission quantum yield used as a light-emitting material or a light-emitting material whose emission spectrum suitable for exhibiting high color purity. In this case, in order to facilitate exciton recombination, the compound according to the embodiment needs to be contained in a concentration sufficient to preferentially trap electrons and holes in the light-emitting layer, and needs to be preferably contained in a concentration of 0.01% or more by mass and 20% or less by mass, more preferably 1% or more by mass and 15% or less by mass. As a light-emitting material, a smaller doping concentration is less susceptible to the influence of concentration quenching and a change in emission spectrum due to the interaction between molecules. Thus, the light-emitting layer can be doped with the light-emitting material other than the compound according to the embodiment. The doping concentration of the light-emitting material is preferably 0.1% or more by mass and 45% or less by mass, more preferably 1% or more by mass and 30% or less by mass. This provides the light-emitting device with high efficiency and high color purity.

(10) The use of a hydrocarbon compound as the light-emitting material provides the light-emitting device with high efficiency and good durability characteristics.

The compound according to the embodiment contains a strong electron-withdrawing carbonyl group. Because of this, as a light-emitting material serving as a dopant described in feature (9) above, a light-emitting material that does not contain an amino group, which is an electron-donating group, can be used, and a compound consisting of a hydrocarbon can be used. The reason for this is that an amino group-containing light-emitting material may interact with the carbonyl group of the compound according to the embodiment in the light-emitting layer to cause a decrease in luminous efficiency due to exciplex formation and a change in the emission spectrum of the light-emitting material, thereby deteriorating the color purity of the light-emitting device.

An amino group-containing light-emitting material is easily oxidized due to its low ionization potential and thus has poor device durability. For this reason, a hydrocarbon compound can be used as a light-emitting material, and a five-membered ring-containing fused polycyclic compound can be used. This is because the structure is less susceptible to oxidation due to its higher ionization potential. A hydrocarbon compound is a compound consisting of only carbon and hydrogen.

As described above, the organic light-emitting device having high luminous efficiency can be provided by mixing the compound according to the embodiment with the host material in the light-emitting layer. Here, the light-emitting material may be the compound according to the embodiment. In addition, a light-emitting material may be mixed, and the compound according to the embodiment may function as an assist material. The use of a light-emitting material with good color purity makes it possible to provide an organic light-emitting device with high efficiency and high color purity. When the host material is a hydrocarbon compound, the compound according to the embodiment can easily trap electrons and holes to contribute to higher efficiency.

Specific examples of the organic compound according to the embodiment are illustrated below. However, the present disclosure is not limited thereto.

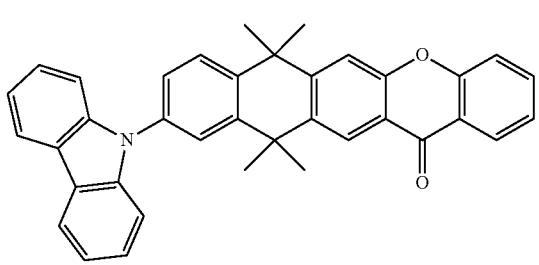

B-1

B-2
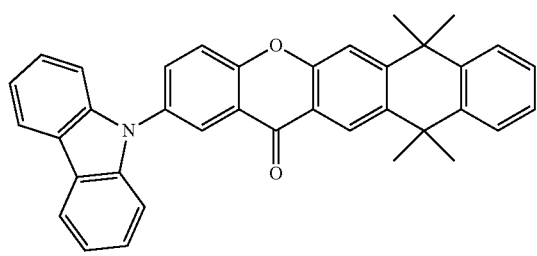
B-3
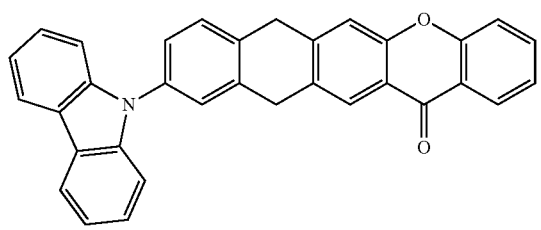
B-4
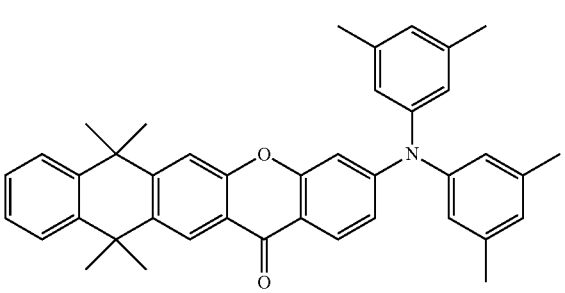
B-5
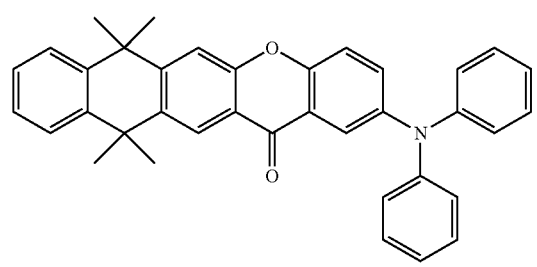
B-6
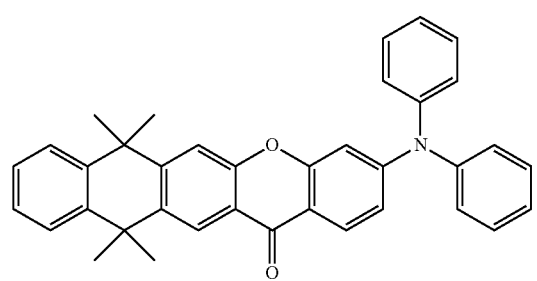
B-7
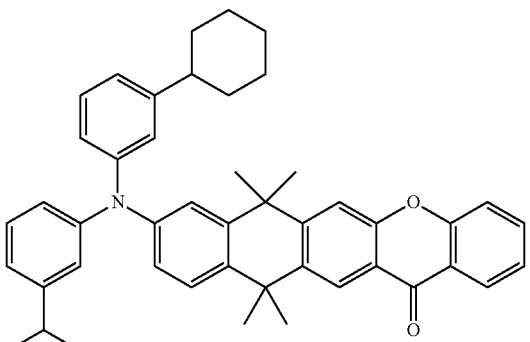
B-8
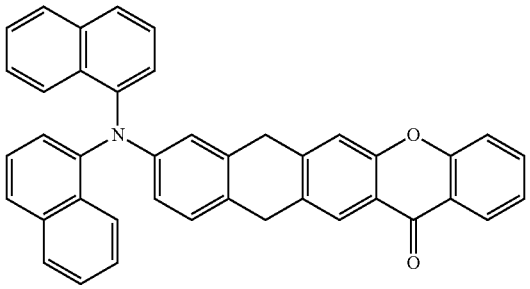
B-9
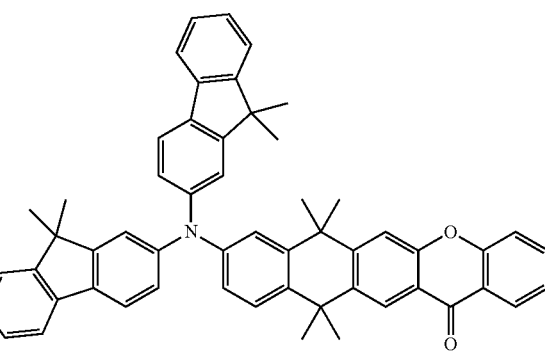
B-10
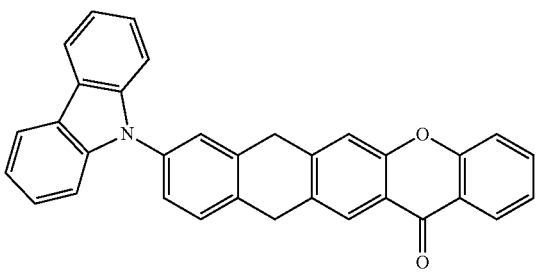

B-11
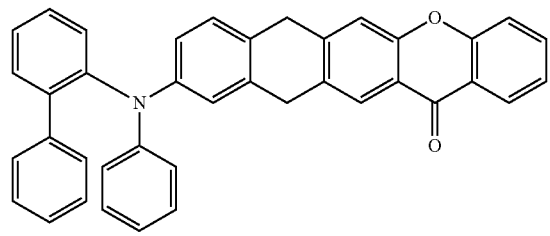
B-16
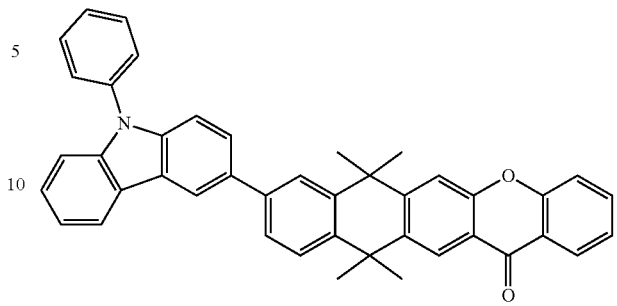
B-12
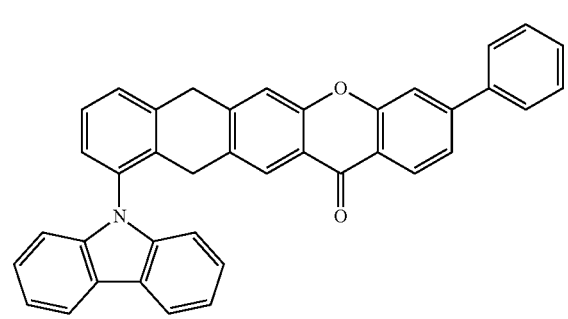
B-17
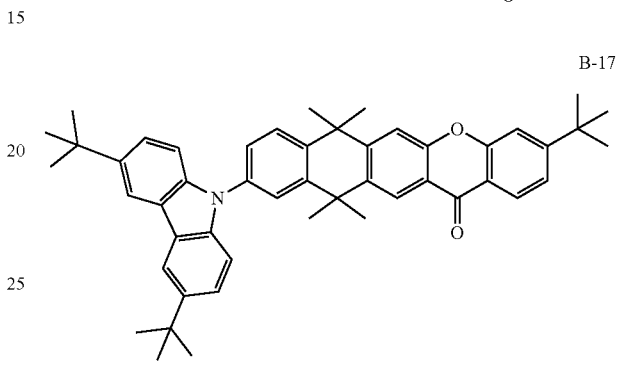
B-13
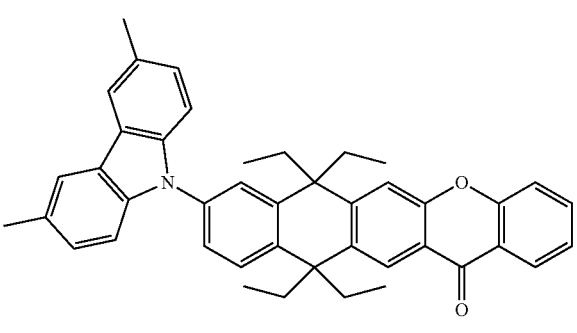
B-18
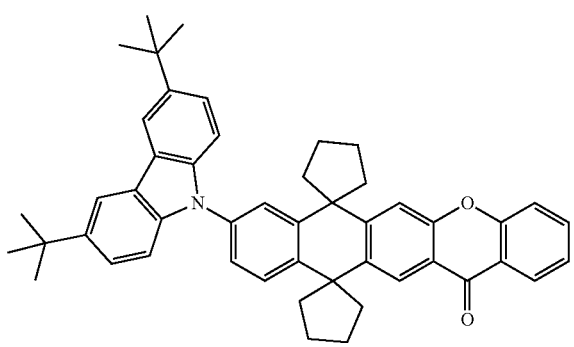 (positions approximate)
B-14
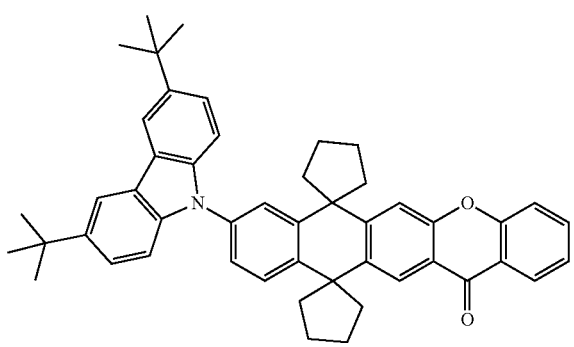
B-19
B-15
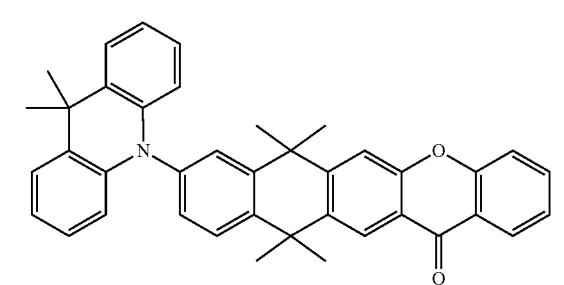
B-20
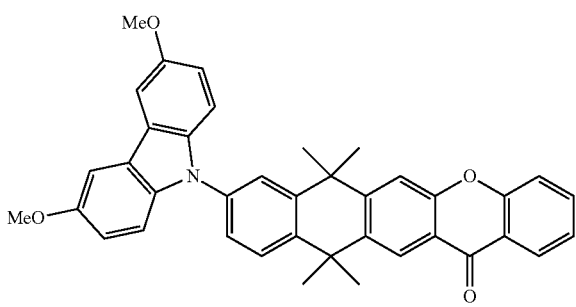

-continued
B-21
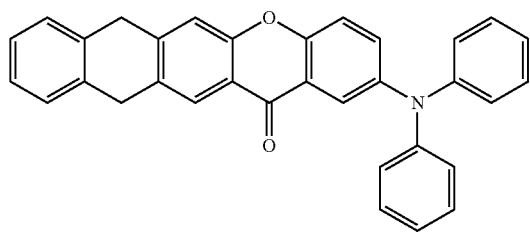
B-22
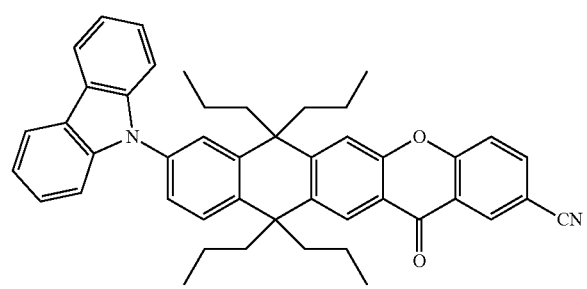
B-23
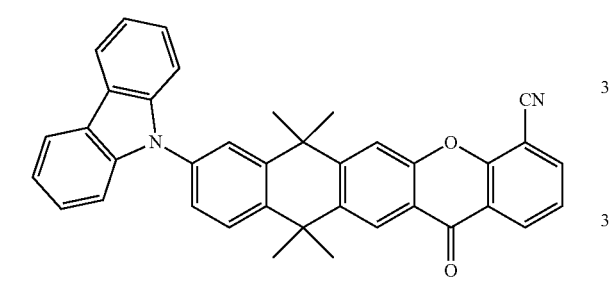
B-24
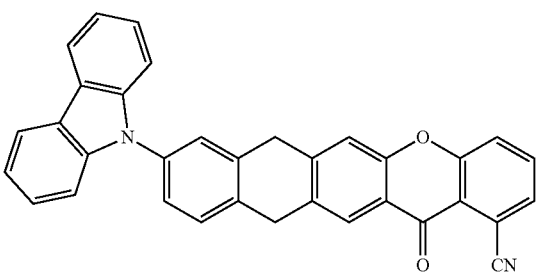
B-25
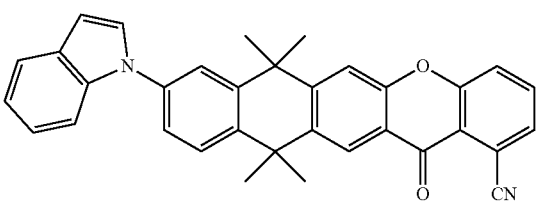
B-26
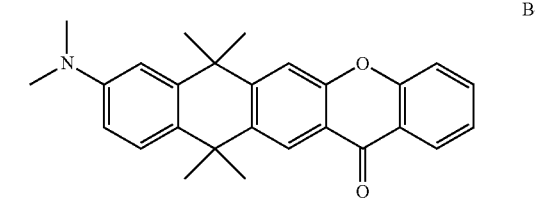
B-27
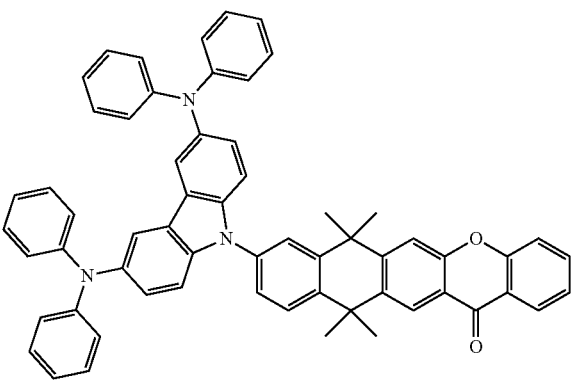
B-28
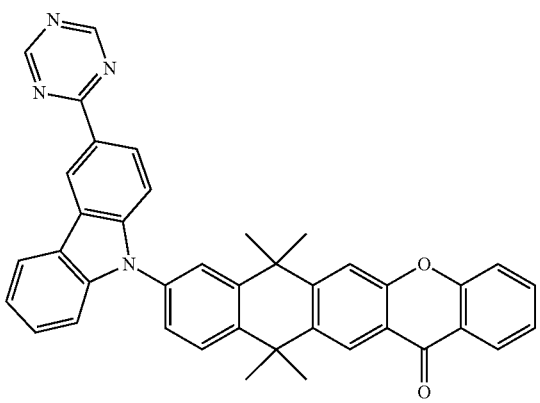
C-1
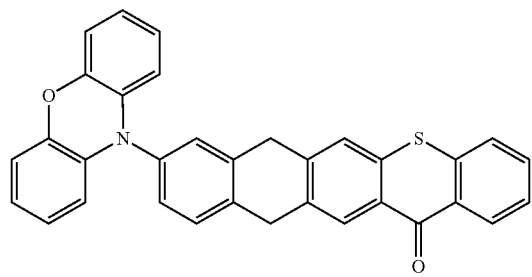
C-2
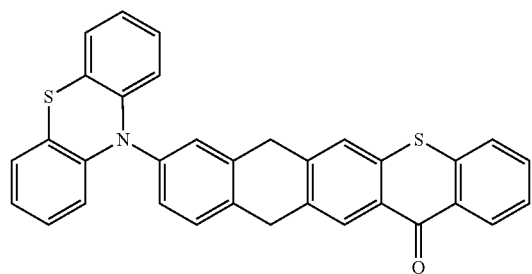

C-3
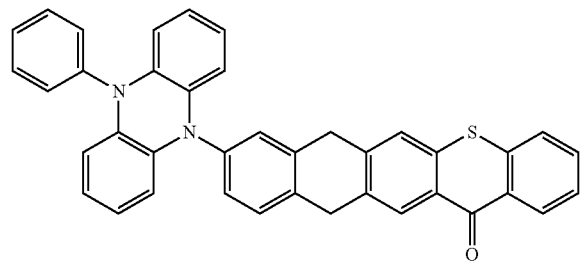
C-4
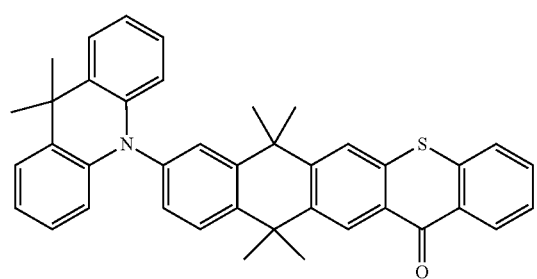
C-5
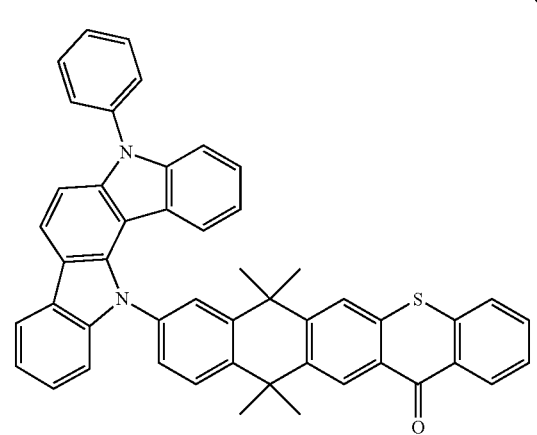
C-6
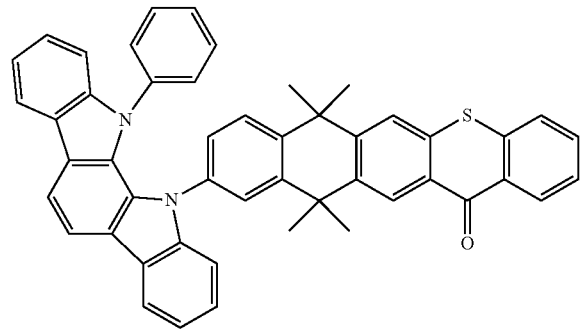
C-7
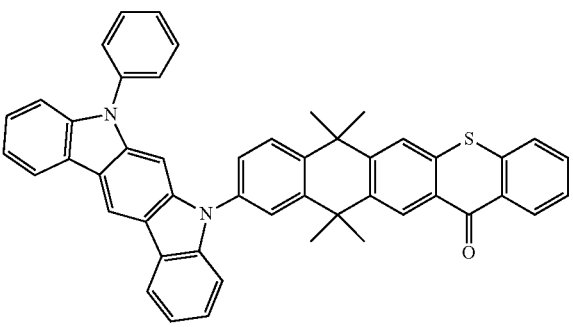
C-8
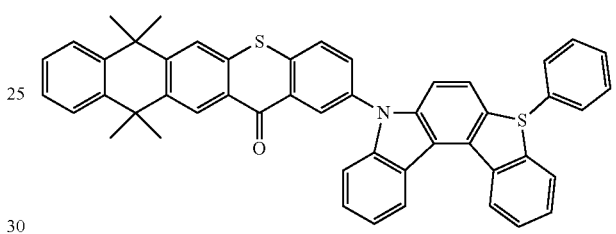
C-9
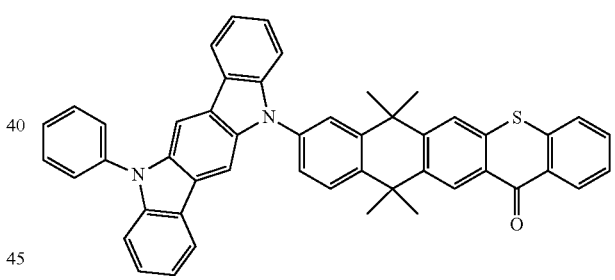
C-10
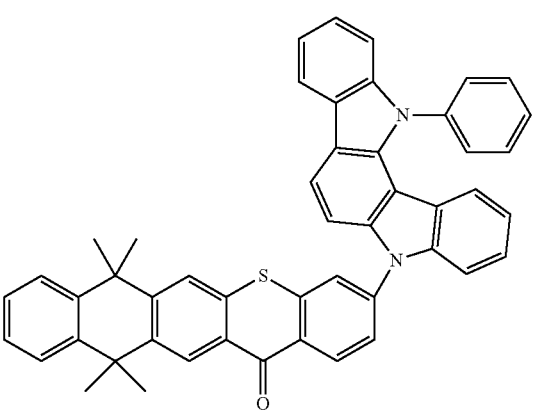

C-11
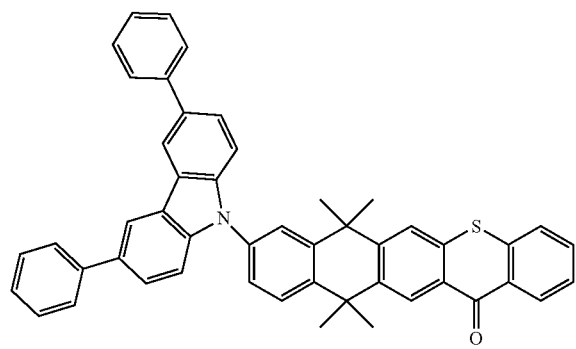
C-12
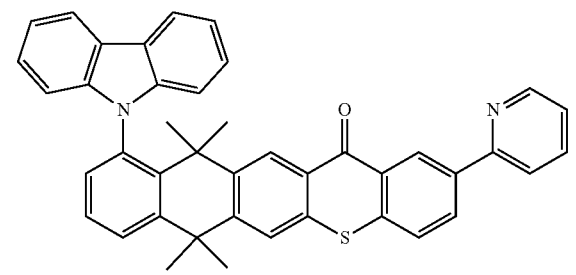
C-13
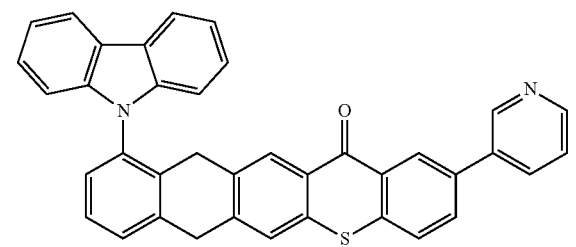
C-14
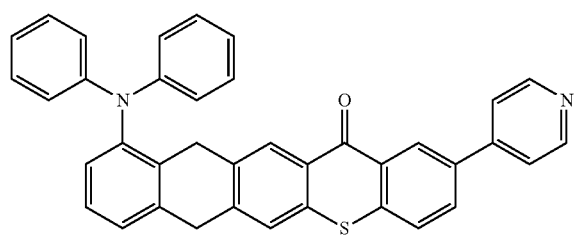
C-15
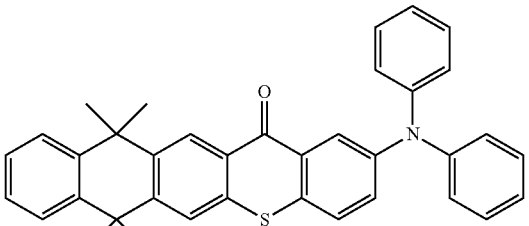
C-16
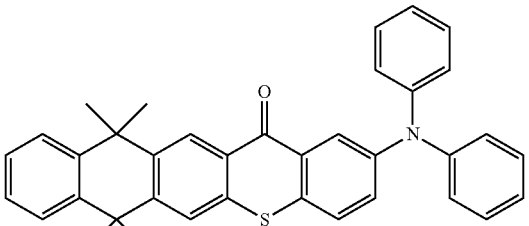
C-17
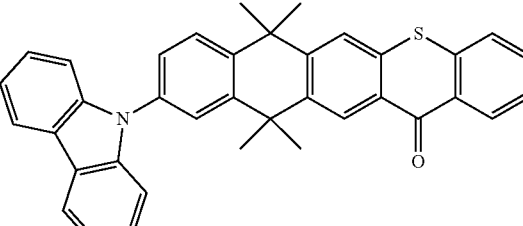
C-18
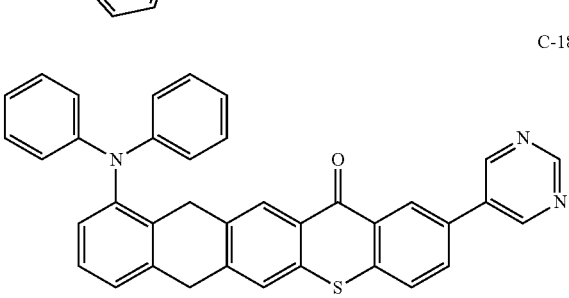
C-19
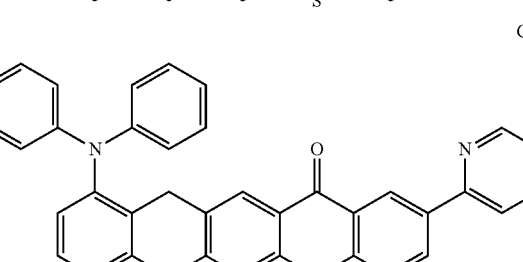
C-20
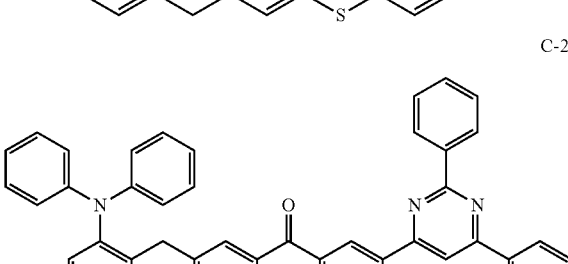
C-21
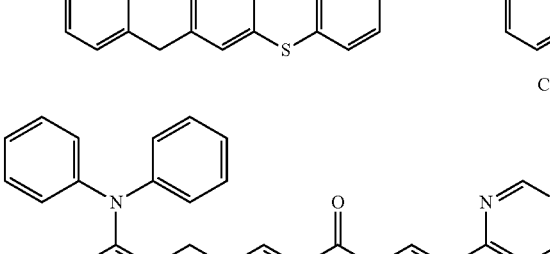

C-22
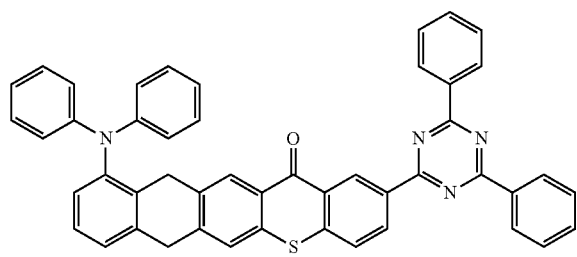
C-27
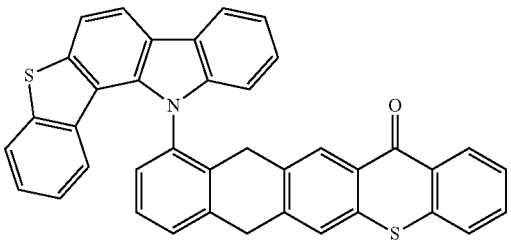
C-23
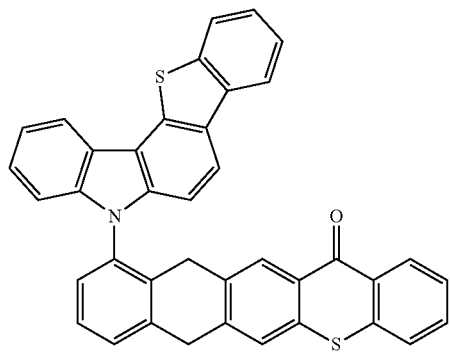
C-28
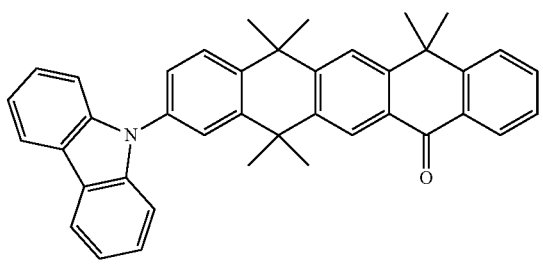
C-24
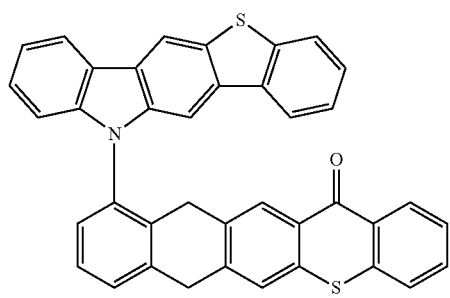
D-1
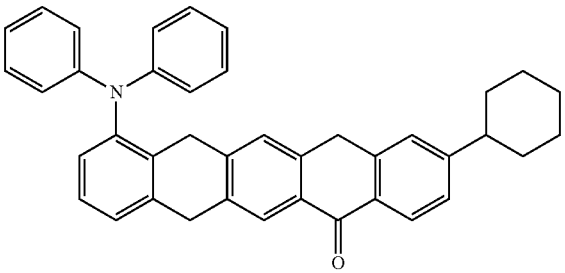
C-25
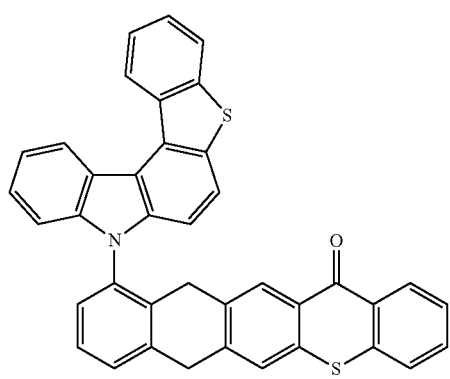
D-2
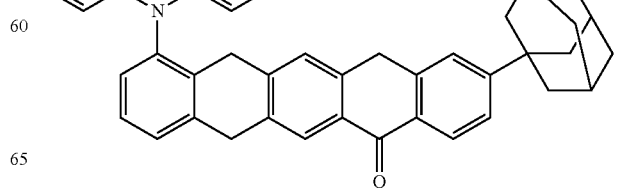
C-26
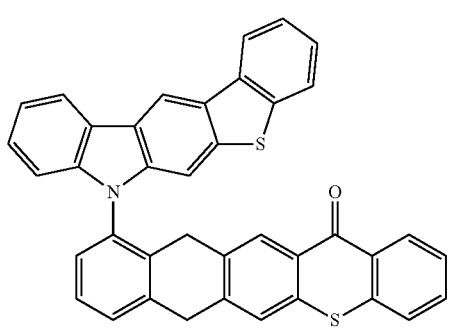
D-3

D-4
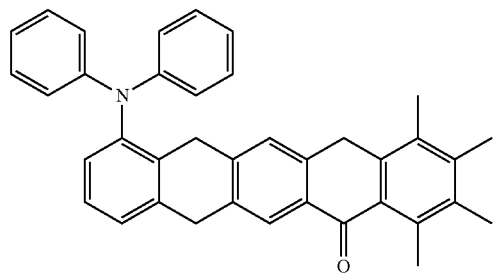
D-5
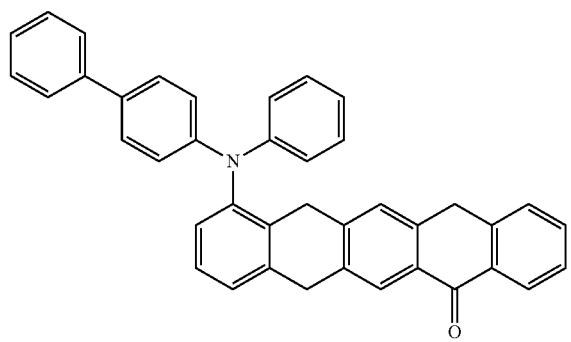
D-6
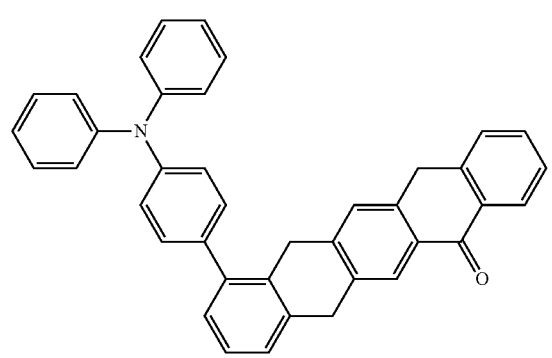
D-7
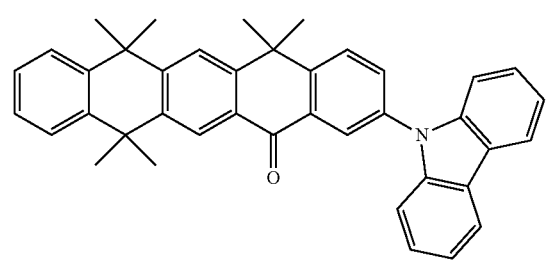
D-8
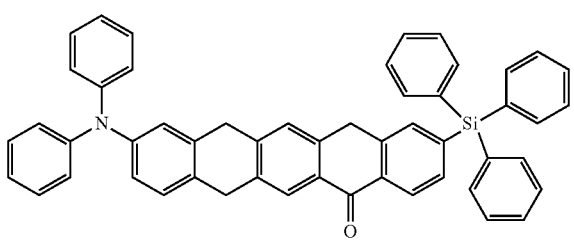
D-9
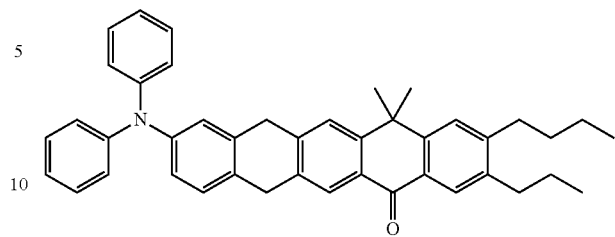
D-10
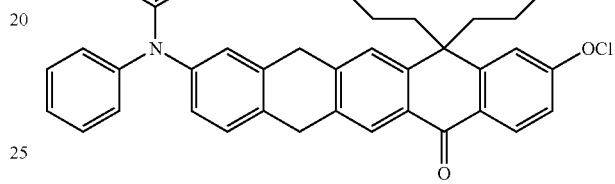
D-11
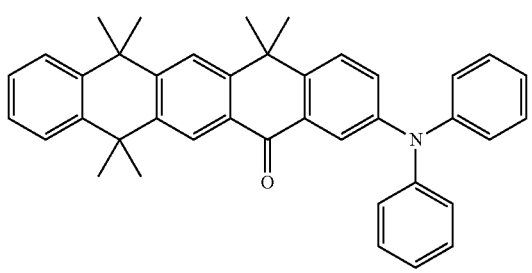
D-12
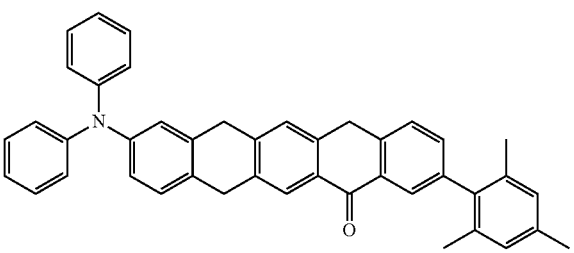
D-13
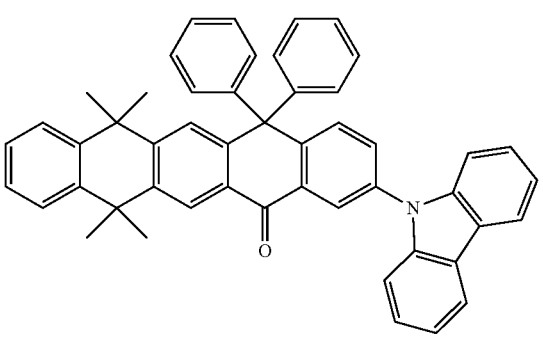

-continued
D-14
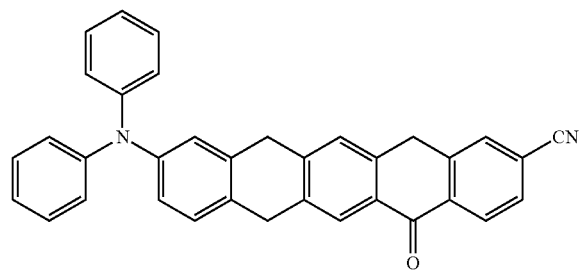
D-15
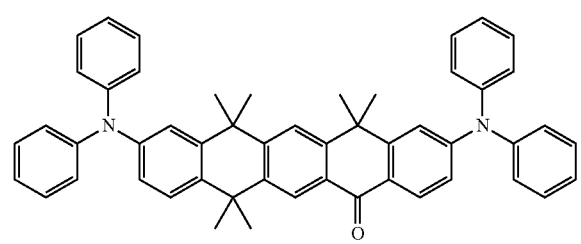
D-16
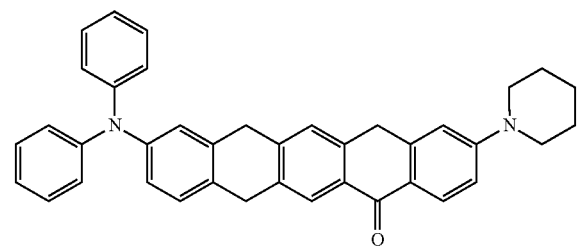
D-17
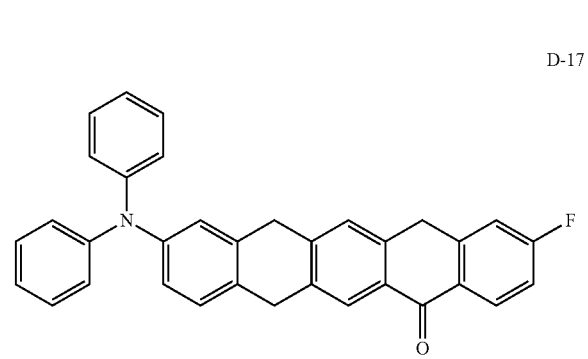
D-18
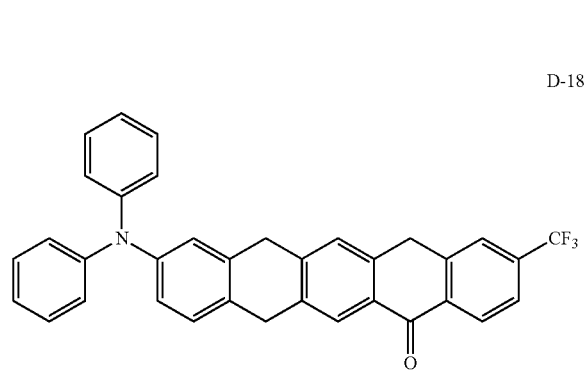
-continued
D-19
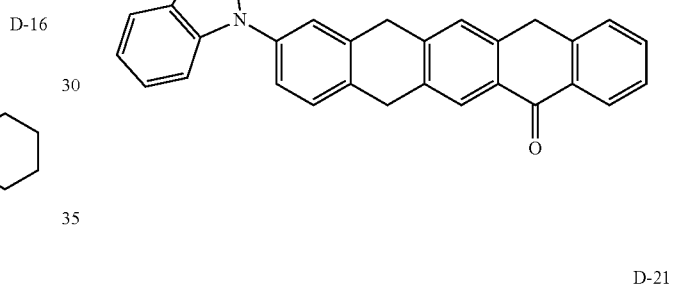
D-20
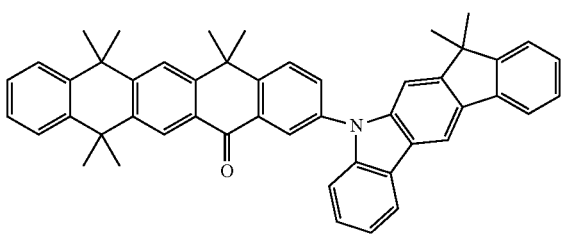
D-21
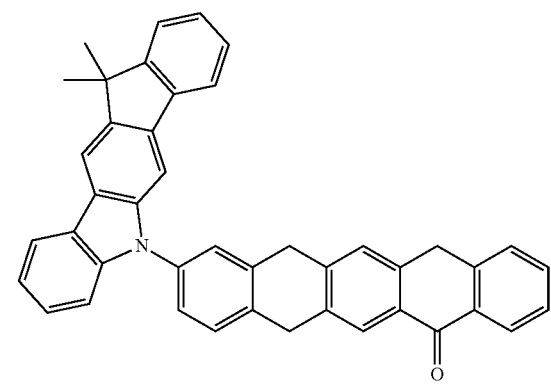
D-22

D-23
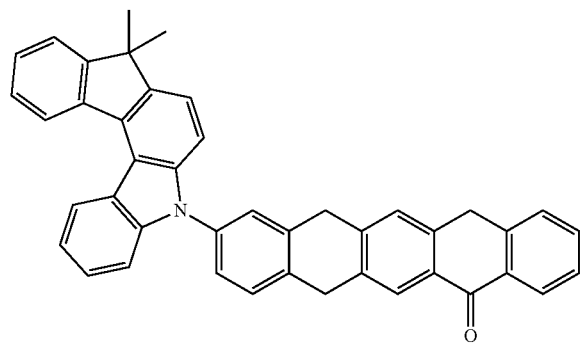
D-24
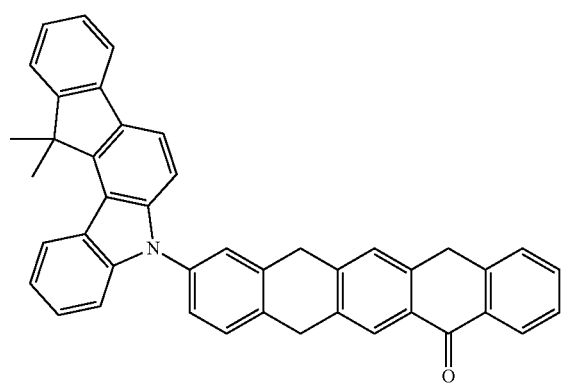
D-25
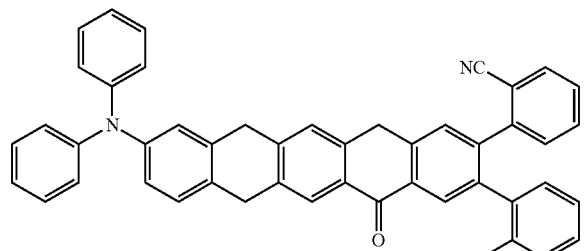
D-26
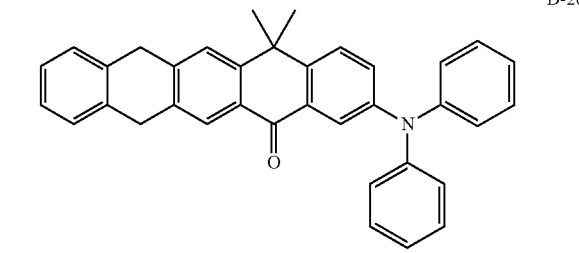
D-27
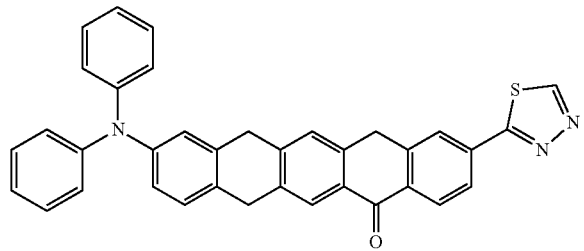
D-28
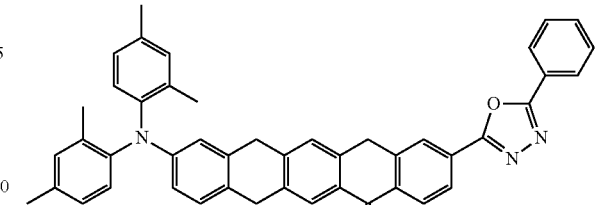
E-1
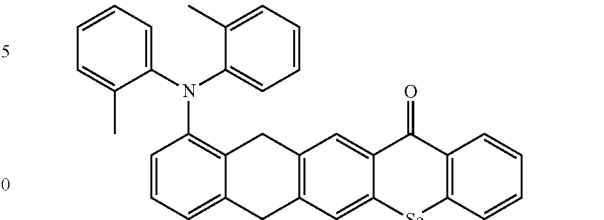
E-2
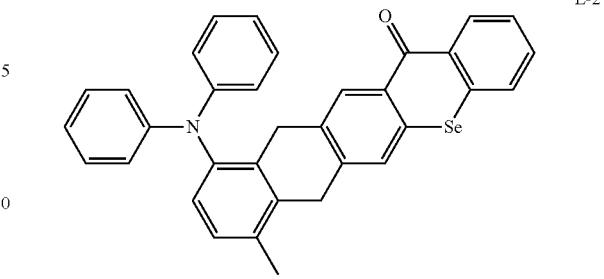
E-3
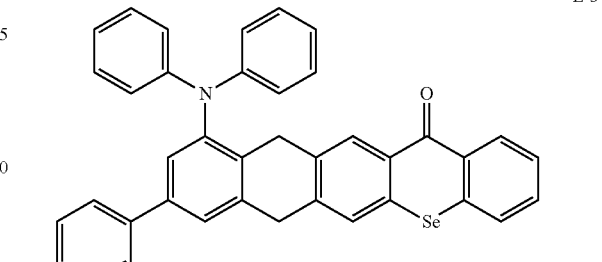
E-4
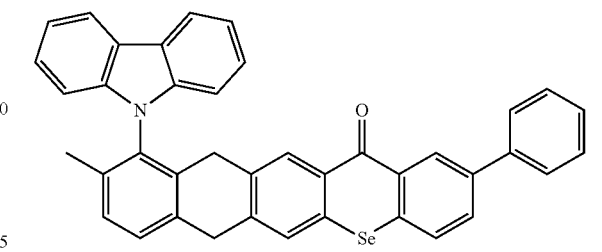
E-5
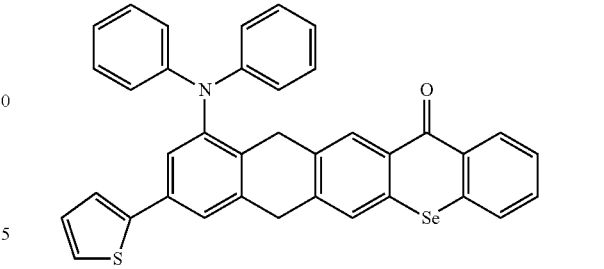

-continued
E-6
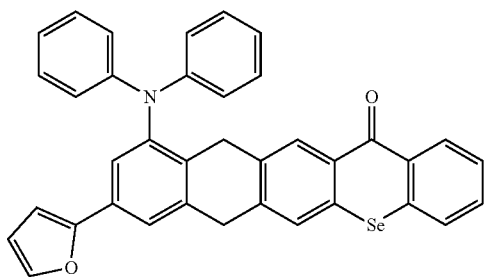
E-7
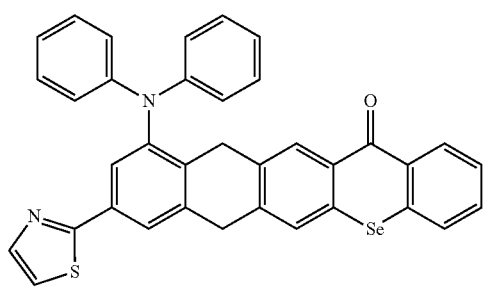
E-8
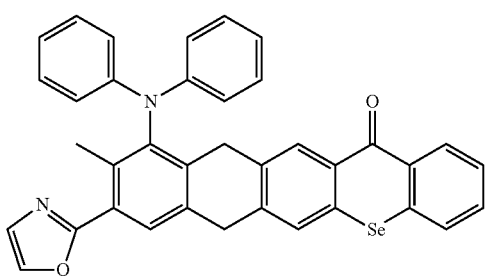
E-9
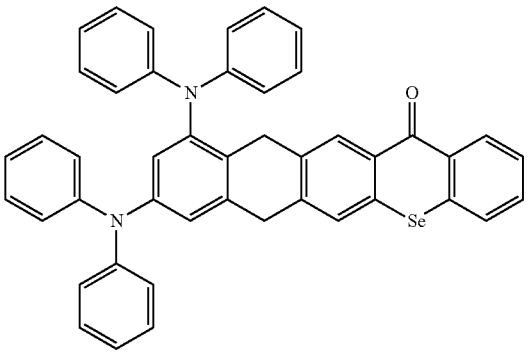
E-10
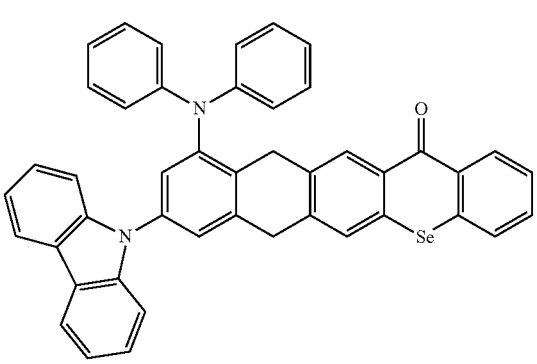
-continued
E-11
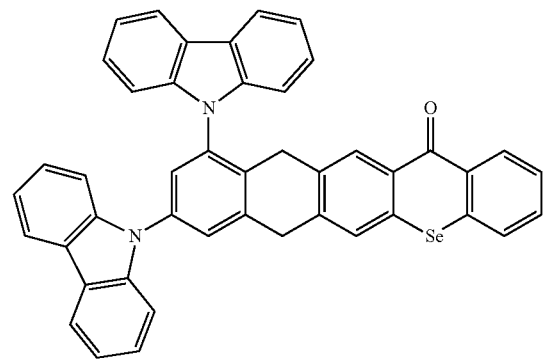
E-12
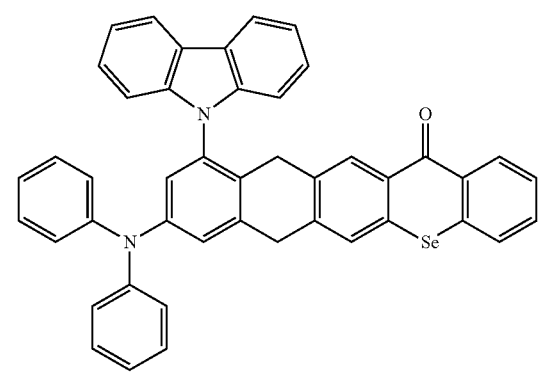
E-13
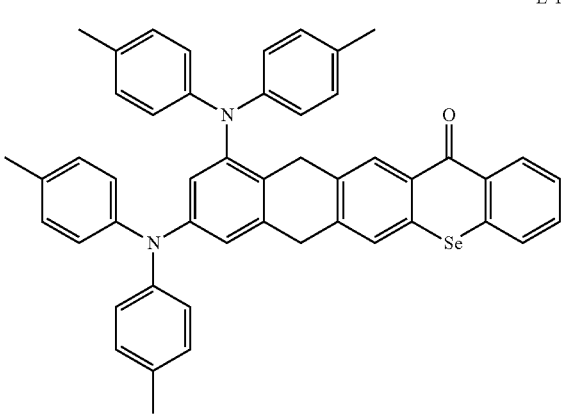
E-14
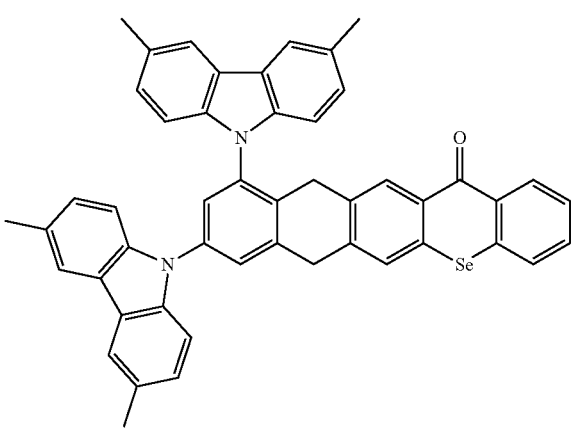

-continued
E-15
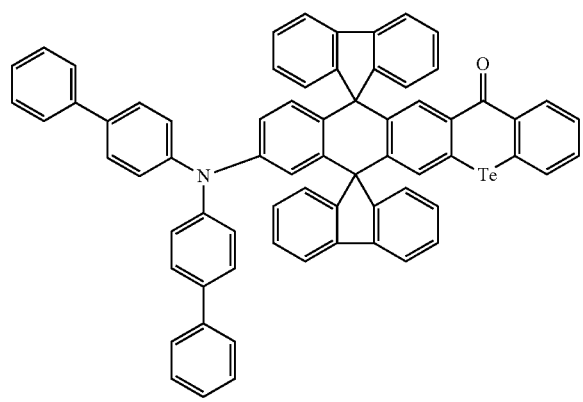
E-16
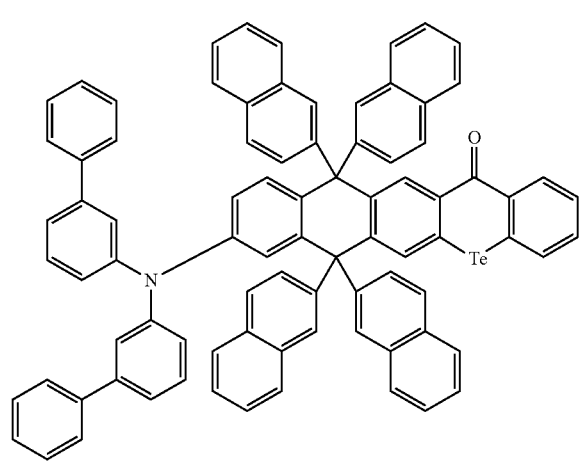
E-17
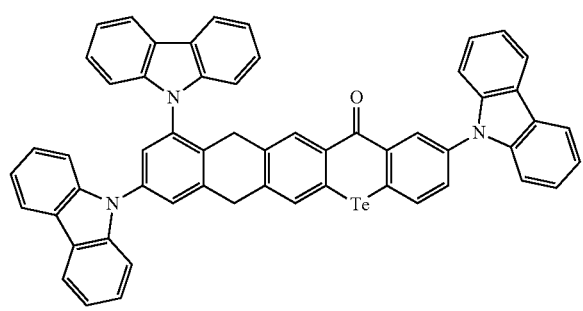
E-18
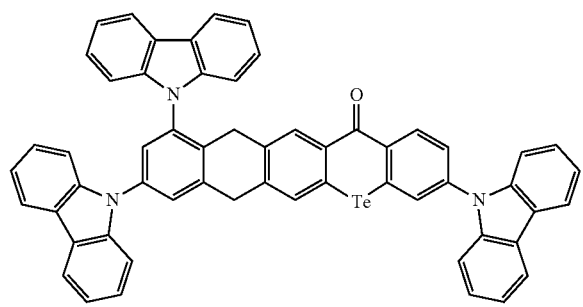
-continued
E-19
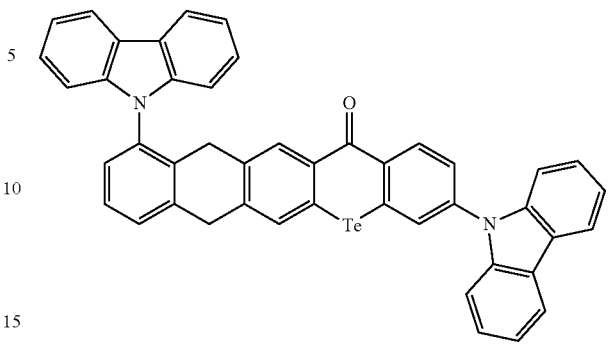
E-20
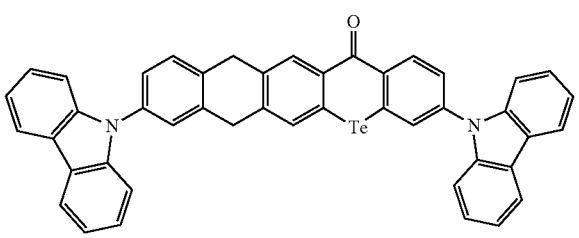
E-21
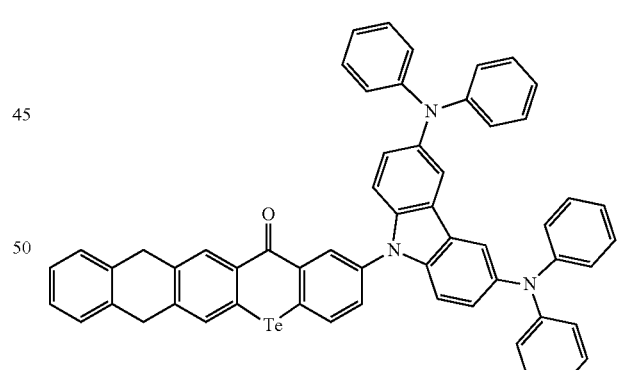
E-22
E-23
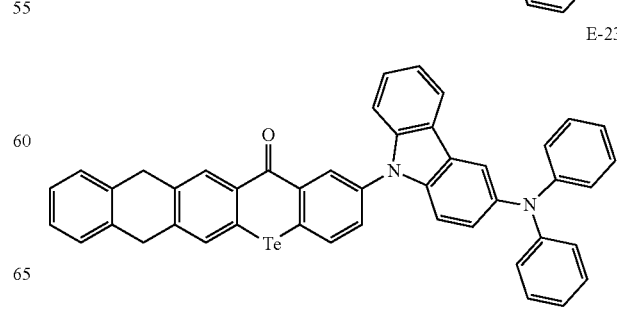

E-24
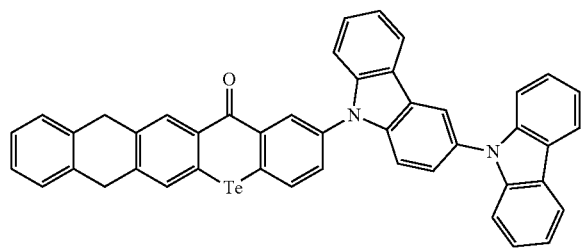

E-28
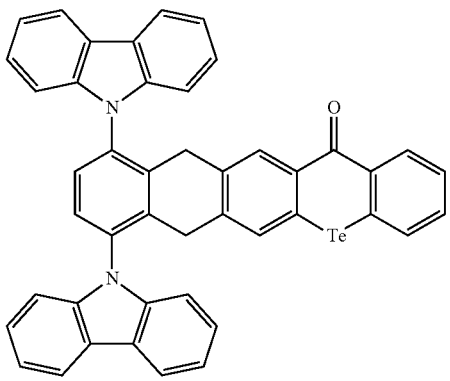

E-25
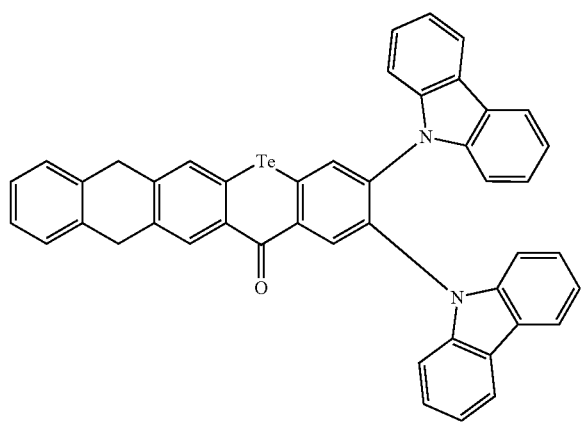

E-26
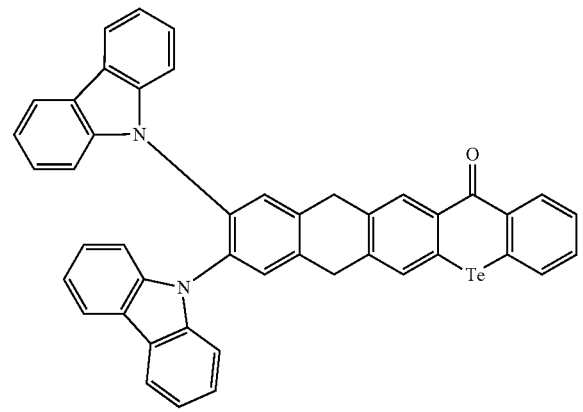

E-27
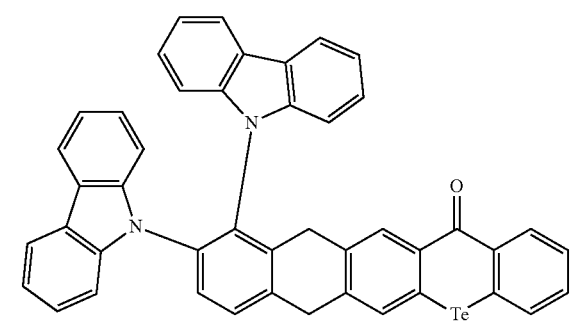

Compounds belonging to group B are each a compound in which X is oxygen. Since X is oxygen, the fused polycyclic structure, which is an electron-withdrawing moiety, is less likely to be subjected to a chemical reaction, such as oxidation, thus providing a chemically stable compound.

Compounds belonging to group C are each a compound in which X is sulfur. Since X is sulfur, the fused polycyclic structure, which is an electron-withdrawing moiety, is a structure having lone pairs abundantly, thus allowing a compound to have superior carrier transport ability.

Compounds belonging to group D are each a compound in which X is $CR_{15}R_{16}$. Since X is $CR_{15}R_{16}$, the compounds are effective in reducing molecular association. Thus, the compounds are less likely to undergo concentration quenching.

Compounds belonging to group E are each a compound in which X is selenium or tellurium. Each of selenium and tellurium is an element having a d-orbital and metallic properties. Thus, the compounds belonging to group E have high carrier mobility. Organic Light-Emitting Device The organic light-emitting device according to the embodiment will be described below.

The organic light-emitting device according to the embodiment at least includes an anode and a cathode, which are a pair of electrodes, and an organic compound layer disposed between these electrodes. In the organic light-emitting device according to the embodiment, the organic compound layer may be formed of a single layer or a multilayer stack including multiple layers, as long as it includes a light-emitting layer. When the organic compound layer is formed of a multilayer stack including multiple layers, the organic compound layer may include, in addition to the light-emitting layer, a hole injection layer, a hole transport layer, an electron-blocking layer, a hole/exciton-blocking layer, an electron transport layer, and an electron injection layer, for example. The light-emitting layer may be formed of a single layer or a multilayer stack including multiple layers.

In the organic light-emitting device according to the embodiment, at least one organic compound layer contains the organic compound according to the embodiment. Specifically, the organic compound according to the embodiment is contained in any of the light-emitting layer, the hole injection layer, the hole transport layer, the electron-blocking layer, the hole/exciton-blocking layer, the electron transport layer, the electron injection layer, and so forth described above. The organic compound according to the embodiment can be contained in the light-emitting layer. The light-emitting layer can emit green light or red light. The emission color is not limited thereto.

In the organic light-emitting device according to the embodiment, in the case where the organic compound according to the embodiment is contained in the light-emitting layer, the light-emitting layer may consist of only the organic compound according to the embodiment or may be composed of the organic compound according to the embodiment and another compound. In the case where the light-emitting layer is composed of the organic compound according to the embodiment and another compound, the organic compound according to the embodiment may be used as a host or a guest in the light-emitting layer. The organic compound may be used as an assist material that can be contained in the light-emitting layer. The term "host" used here refers to a compound having the highest proportion by mass in compounds constituting the light-emitting layer. The term "guest" refers to a compound that has a lower proportion by mass than the host in the compounds constituting the light-emitting layer and that is responsible for main light emission. The term "assist material" refers to a compound that has a lower proportion by mass than the host in the compounds constituting the light-emitting layer and that assists the light emission of the guest.

In the case where the organic compound according to the embodiment is used as a guest in the light-emitting layer, the concentration of the guest is preferably 0.01% or more by mass and 20% or less by mass, more preferably 1% or more by mass and 15% or less by mass, based on the entire light-emitting layer. In the case where the organic compound according to the embodiment is used as an assist material in the light-emitting layer, the concentration of the assist material is preferably 0.1% or more by mass and 45% or less by mass, more preferably 1% or more by mass and 30% or less by mass, based on the entire light-emitting layer.

In the case where the organic compound according to the embodiment is used as a guest in the light-emitting layer, a material having a higher LUMO level than the organic compound according to the embodiment (a material having a LUMO level closer to the vacuum level) can be used as a host. The reason for this is as follows: The organic compound according to the embodiment has a low LUMO level. Thus, when a material having a higher LUMO level than the organic compound according to the embodiment is used as a host, the organic compound according to the embodiment can receive more electrons supplied to the host of the light-emitting layer.

In the case where the organic compound according to the embodiment is used as an assist material in the light-emitting layer, a material having a higher LUMO level than the organic compound according to the embodiment (a material having a LUMO level closer to the vacuum level) can be used as a guest. The reason for this is as follows: The organic compound according to the embodiment has a low LUMO level. Thus, when a material having a higher LUMO level than the organic compound according to the embodiment is used as a guest serving as a light-emitting material, the organic compound according to the embodiment receives more electrons supplied to the host of the light-emitting layer, and the assist material is responsible for exciton recombination. This enables efficient energy transfer to the guest serving as a light-emitting material.

The inventors have conducted various studies and have found that when the organic compound according to the embodiment is used as a host, guest, or assist material of a light-emitting layer, especially as a guest of a light-emitting layer, a device that emits light with high efficiency and high luminance, and is extremely durable can be provided. The inventors have further found that when the organic compound according to the embodiment is used as an assist material in the light-emitting layer, a device that emits light with high efficiency and high luminance, and is extremely durable can be provided. The light-emitting layer may be formed of a single layer or multiple layers, and can contain multiple light-emitting materials. The term "multiple layers" may include a state in which the light-emitting layer and another light-emitting layer are stacked, or a state in which an intermediate layer is stacked between multiple light-emitting layers. Tandem devices or stacked devices are also acceptable. In these cases, the emission color of the organic light-emitting device is not limited to a single color. More specifically, the emission color may be white or an intermediate color. A film-forming method is vapor deposition or coating. Details will be described in examples below.

The organic compound according to the embodiment can be used as a constituent material of an organic compound layer other than the light-emitting layer included in the organic light-emitting device according to the embodiment. Specifically, the organic compound may be used as a constituent material of the electron transport layer, the electron injection layer, the hole transport layer, the hole injection layer, the hole-blocking layer, and so forth.

For example, a hole injection compound, a hole transport compound, a compound to be used as a host, a light-emitting compound, an electron injection compound, or an electron transport compound, which is known and has a low or high molecular weight, can be used together with the organic compound according to the embodiment, as needed. Examples of these compounds will be described below.

As a hole injection-transport material, a material having a high hole mobility can be used so as to facilitate the injection of holes from the anode and to transport the injected holes to the light-emitting layer. To reduce a deterioration in film quality, such as crystallization, in the organic light-emitting device, a material having a high glass transition temperature can be used. Examples of a low- or high-molecular-weight material having the ability to inject and transport holes include triarylamine derivatives, aryl carbazole derivatives, phenylenediamine derivatives, stilbene derivatives, phthalocyanine derivatives, porphyrin derivatives, poly(vinyl carbazole), polythiophene, and other conductive polymers. Moreover, the hole injection-transport material can be used for the electron-blocking layer. Non-limiting specific examples of a compound used as the hole injection-transport material will be illustrated below.

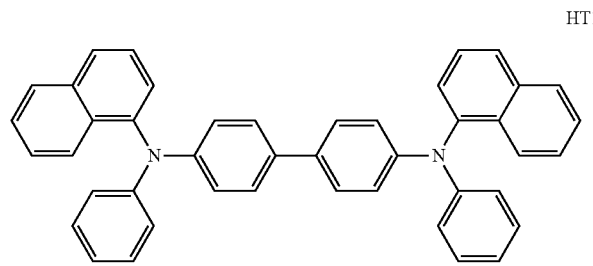 HT1
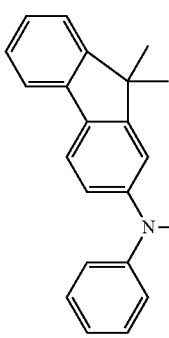 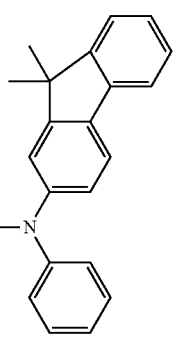 HT2
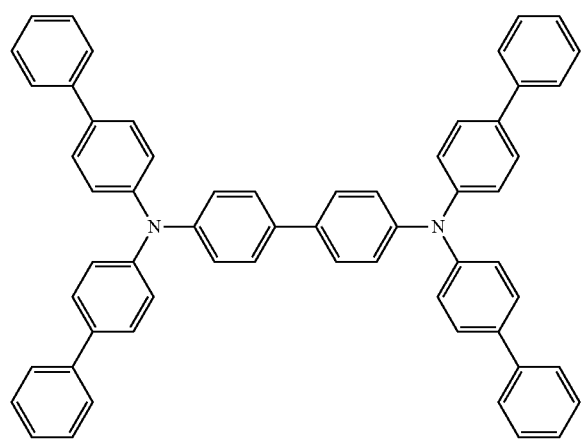 HT3
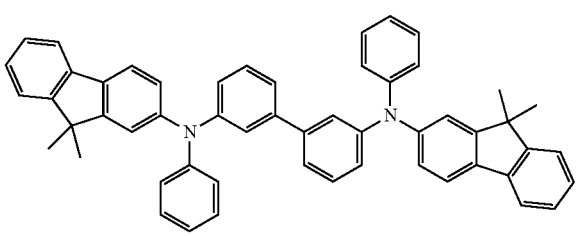 HT4
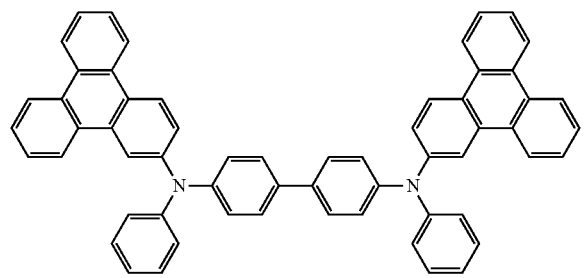 HT5
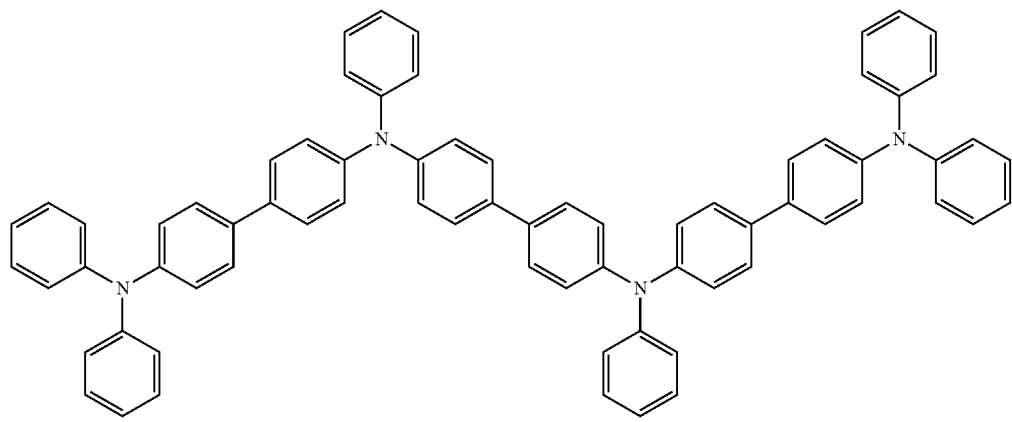 HT6

-continued
HT7
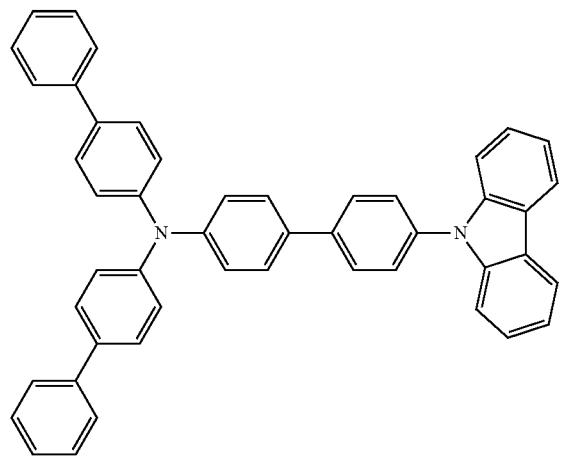
HT8
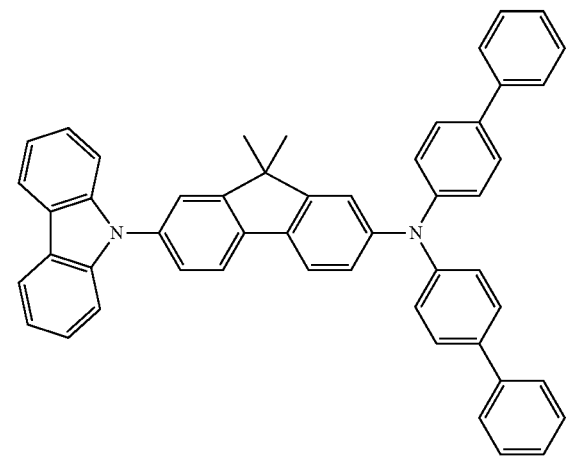
HT9
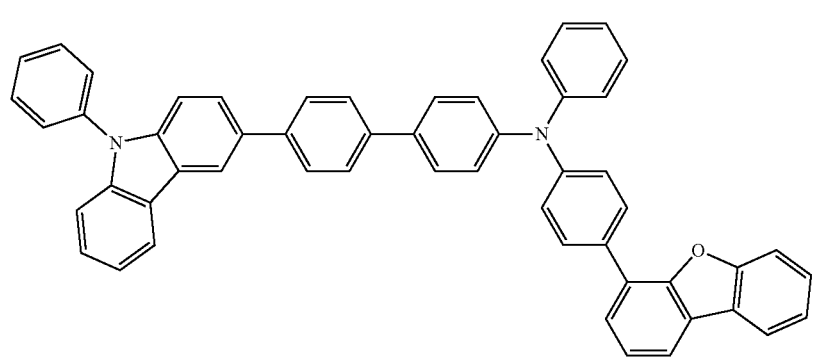
HT10
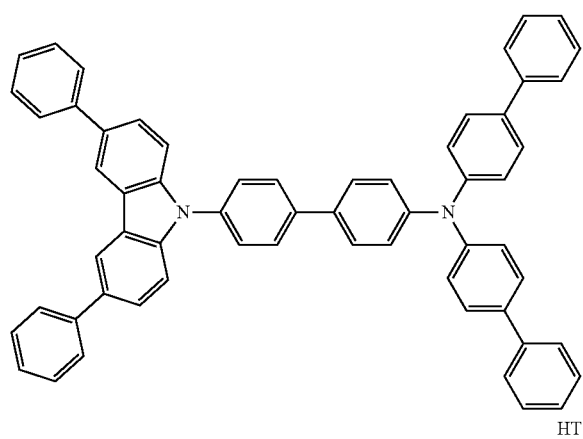
HT11
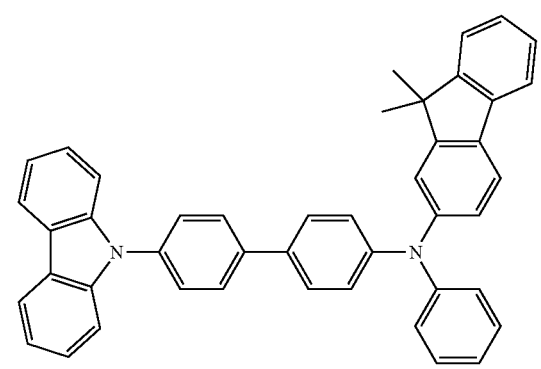
HT12
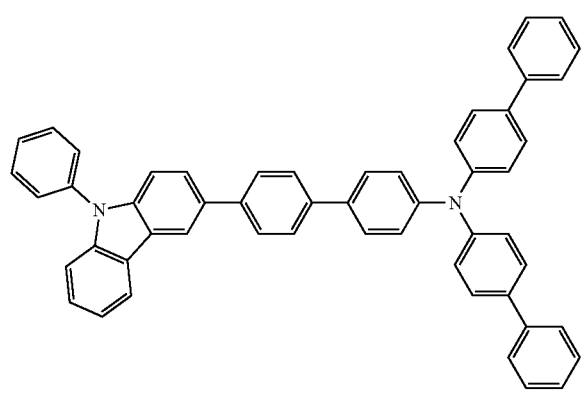
HT13
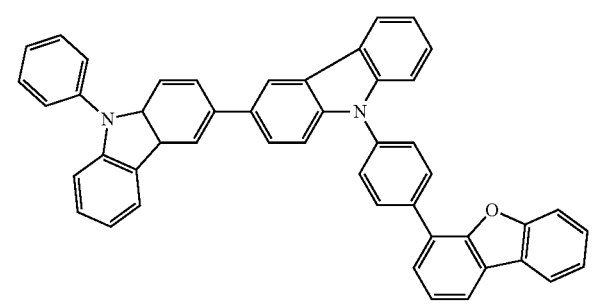

-continued

HT14
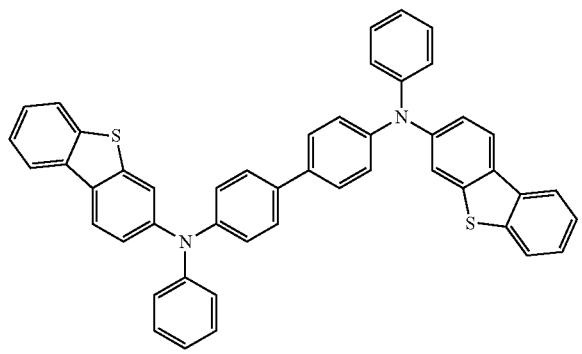

HT15
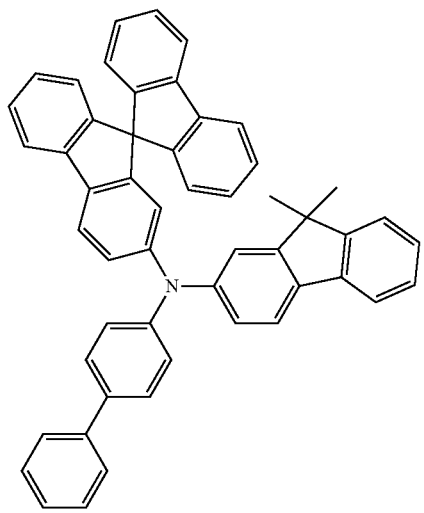

HT16
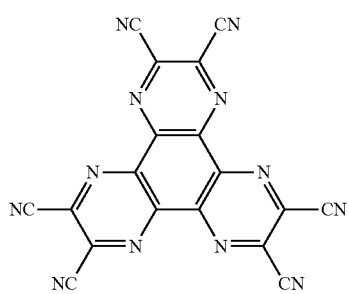

HT17
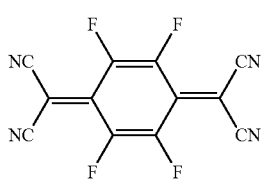

HT18
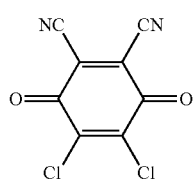

HT19
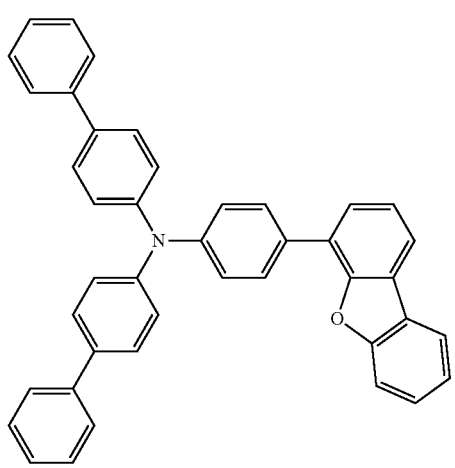

Among the hole transport materials illustrated above, HT16 to HT18 can be used in the layer in contact with the anode to reduce the driving voltage. HT16 is widely used in organic light-emitting devices. HT2, HT3, HT4, HT5, HT6, HT10, and HT12 may be used in an organic compound layer adjacent to HT16. Multiple materials may be used in a single organic compound layer.

Examples of a light-emitting material mainly associated with a light-emitting function include, in addition to the organic compounds represented by formula [1], fused-ring compounds, such as fluorene derivatives, naphthalene derivatives, pyrene derivatives, perylene derivatives, tetracene derivatives, anthracene compounds, and rubrene, quinacridone derivatives, coumarin derivatives, stilbene derivatives, organoaluminum complexes, such as tris(8-quinolinolato)aluminum, iridium complexes, platinum complexes, rhenium complexes, copper complexes, europium complexes, ruthenium complexes, and polymer derivatives, such as poly(phenylene vinylene) derivatives, polyfluorene derivatives, and polyphenylene derivatives. Non-limiting specific examples of a compound used as a light-emitting material are illustrated below.

BD1
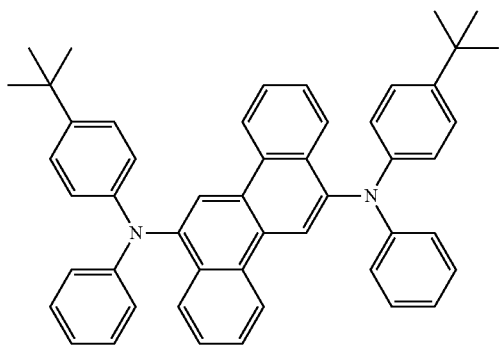
BD5
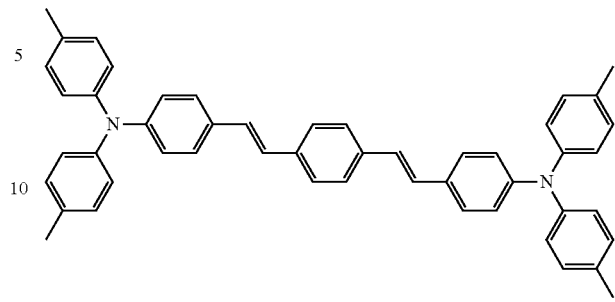
BD2
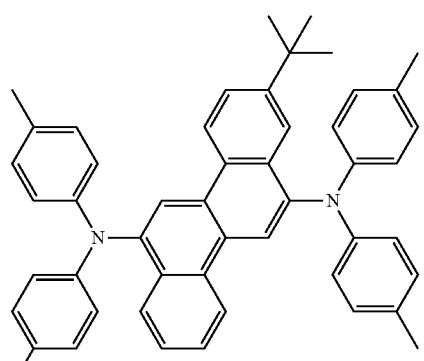
BD6
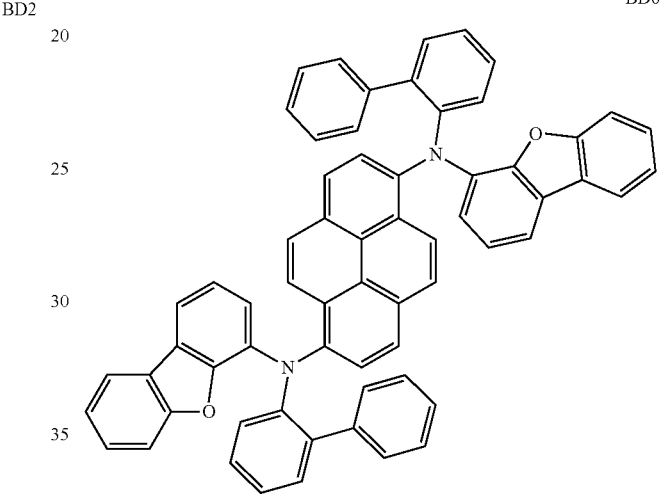
BD3
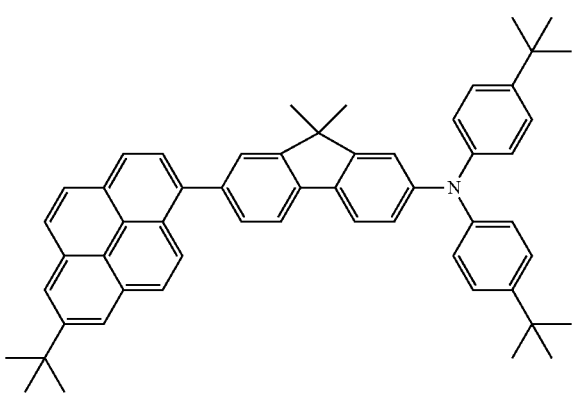
BD7
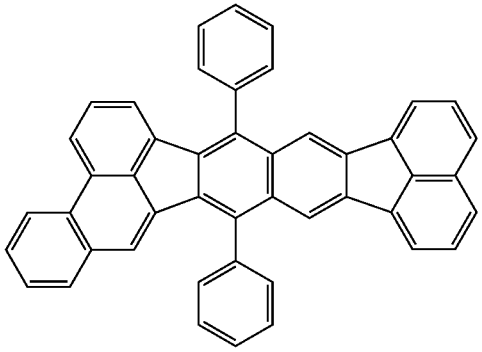
BD4
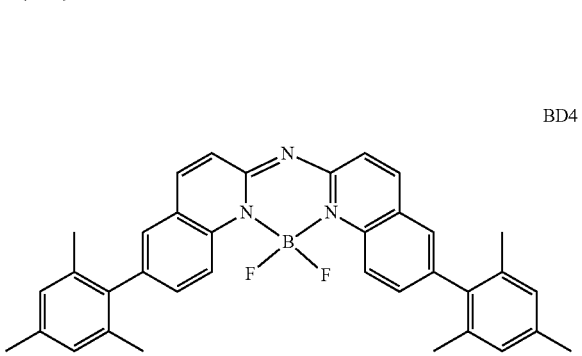
BD8
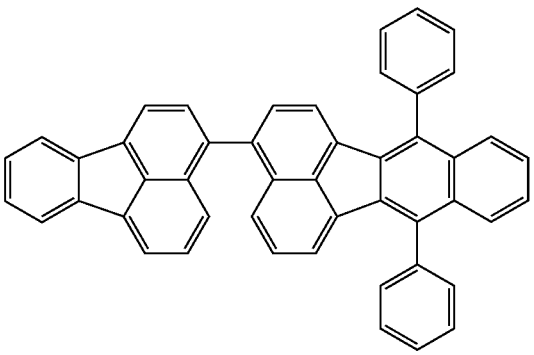

BD9
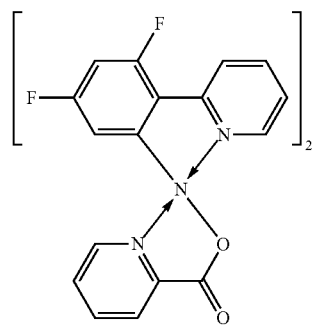
GD3
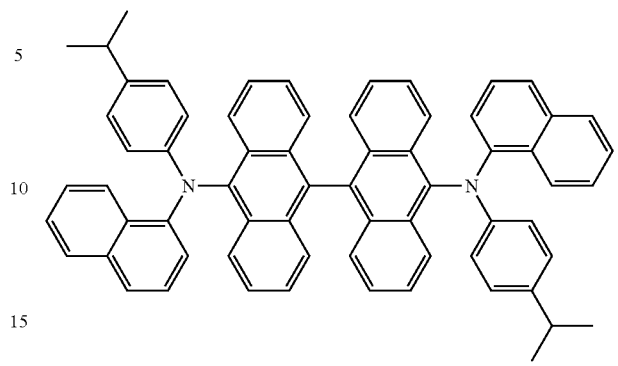
BD10
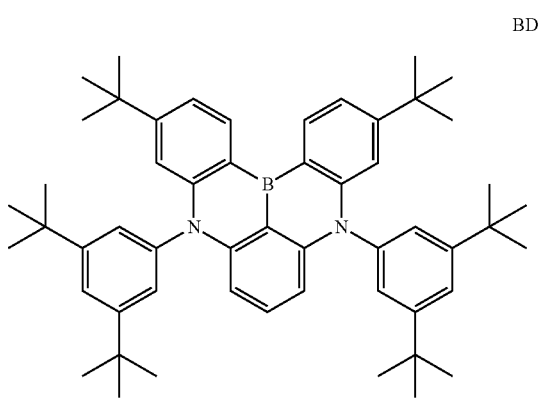
GD4
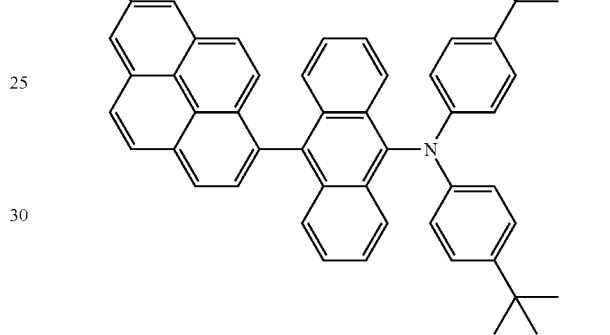
GD1
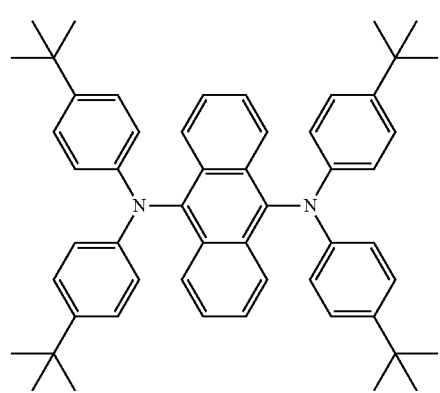
GD5
GD6
GD2
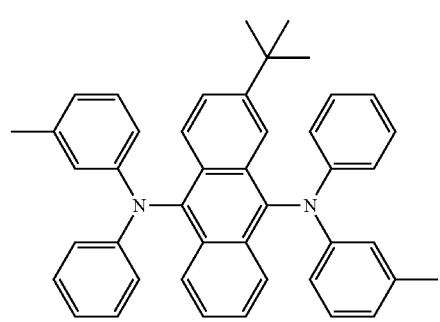

-continued
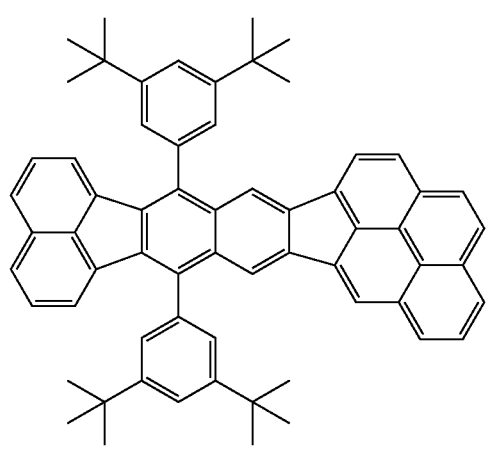
GD7
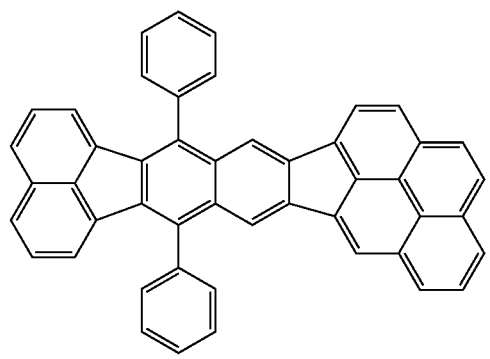
GD8
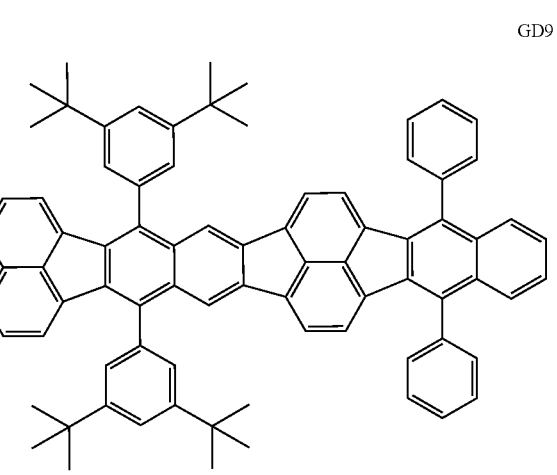
GD9
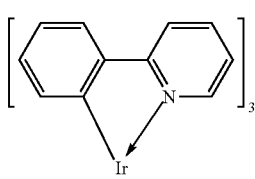
GD10
-continued
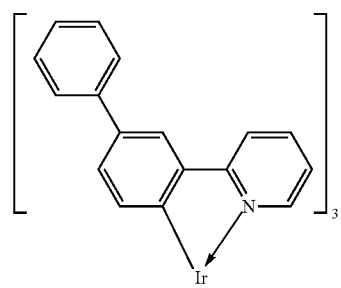
GD11
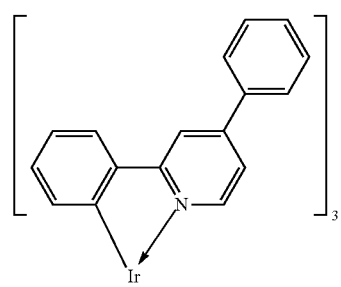
GD12
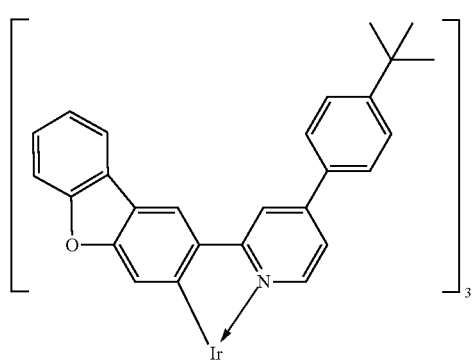
GD13
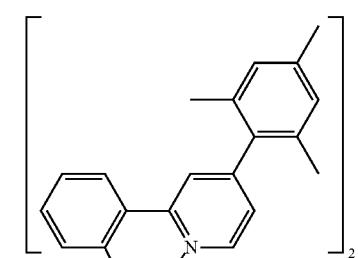
GD14
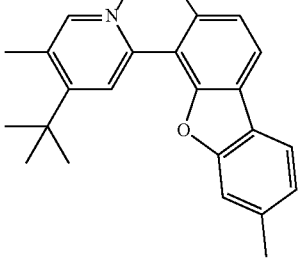

-continued
GD15
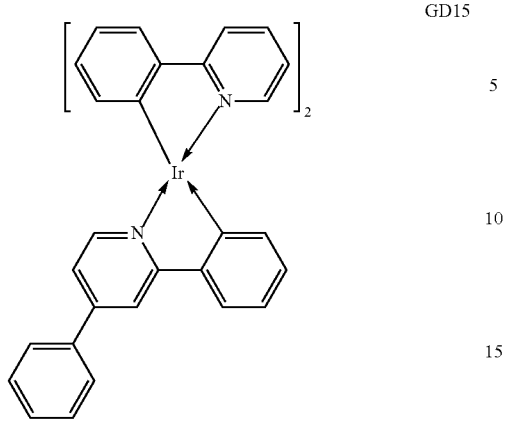
RD1
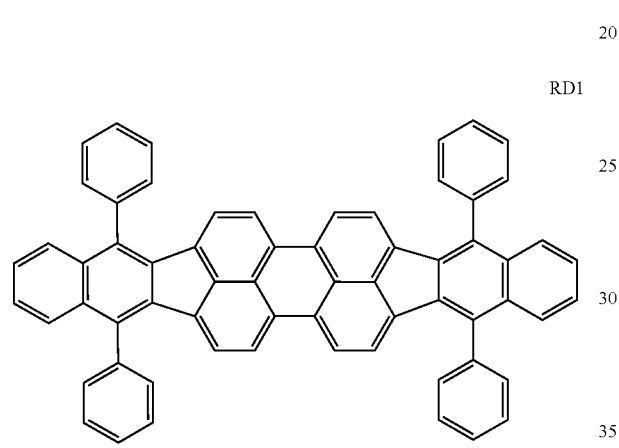
RD2
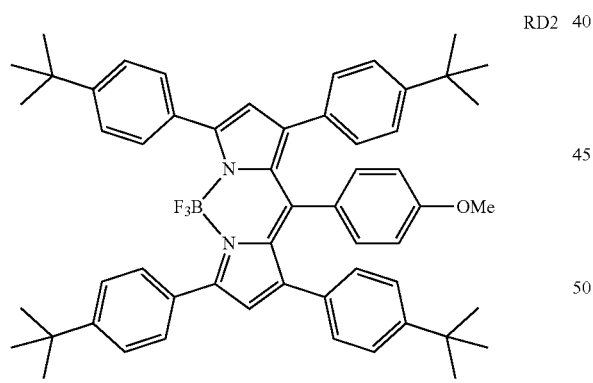
RD3
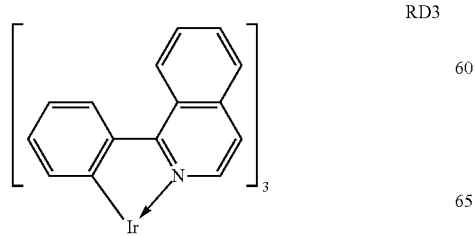
-continued
RD4
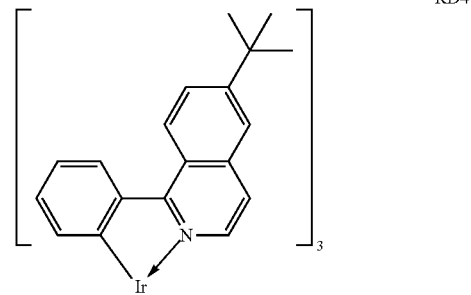
RD5
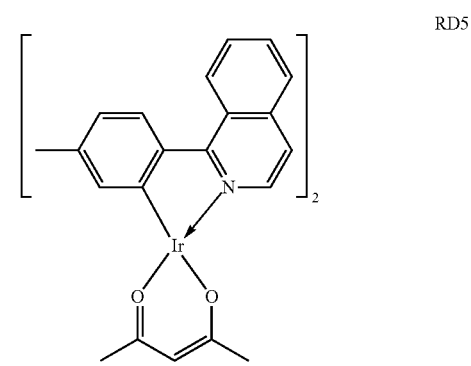
RD6
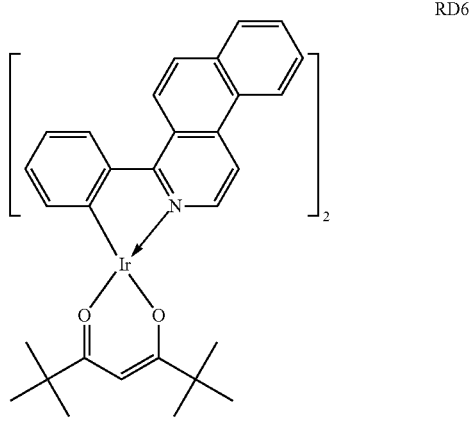
RD7
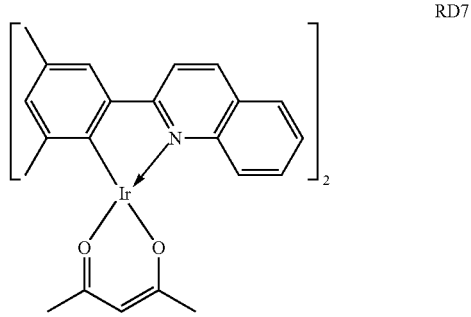

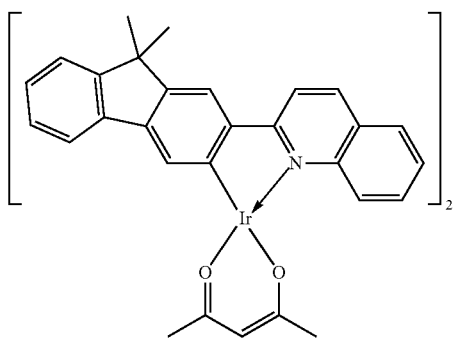

RD8

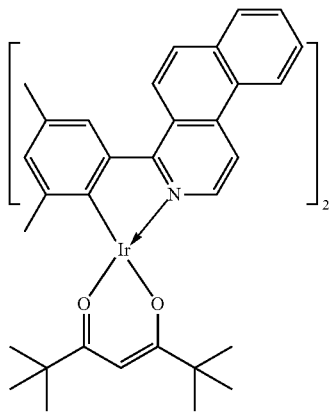

RD10

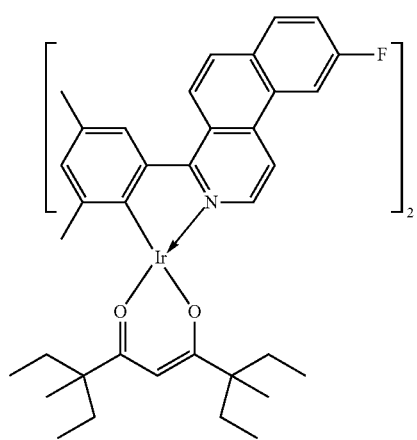

RD9

When the light-emitting material is a hydrocarbon compound, the material can prevent a deterioration in luminous efficiency due to exciplex formation and a deterioration in color purity due to changes in the emission spectrum of the light-emitting material. The term "hydrocarbon compound" refers to a compound consisting of only carbon and hydrogen, and BD7, BD8, GD5 to GD9, and RD1 are hydrocarbon compounds. When the light-emitting material is a five-membered ring-containing fused polycyclic compound, the material has a high ionization potential and high resistance to oxidation. This can provide a highly durable device with a long lifetime. BD7, BD8, GD5 to GD9, and RD1 are five-membered ring-containing fused polycyclic compounds.

Examples of a host or an assist material in the light-emitting layer include aromatic hydrocarbon compounds and derivatives thereof, carbazole derivatives, dibenzofuran derivatives, dibenzothiophene derivatives, organoaluminum complexes, such as tris(8-quinolinolato)aluminum, and organoberyllium complexes. Non-limiting specific examples of a compound used as a host or an assist material in the light-emitting layer will be illustrated below.

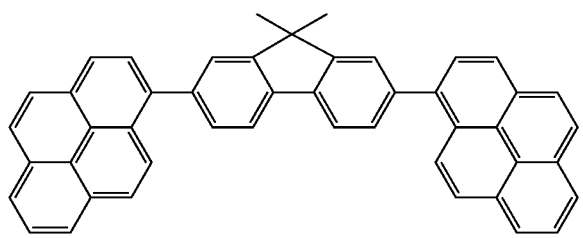

EM1

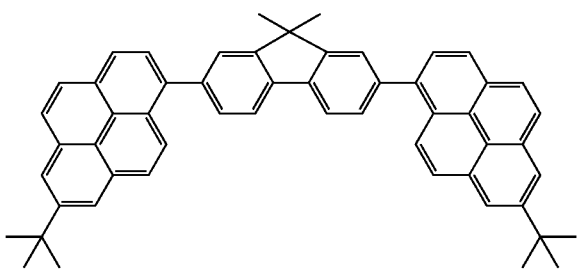

EM2

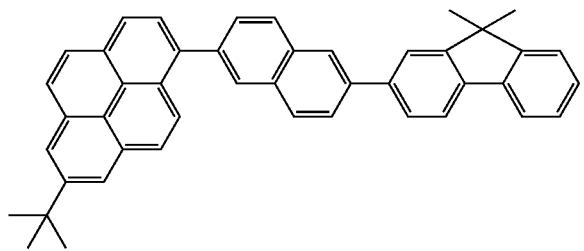

EM3

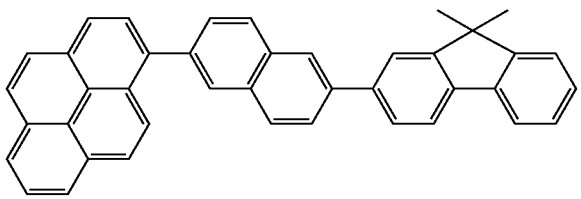

EM4

-continued
EM5
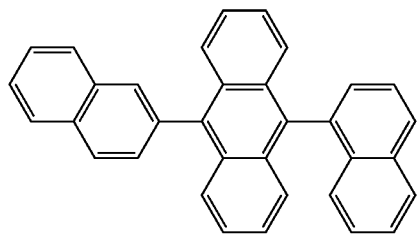
EM6
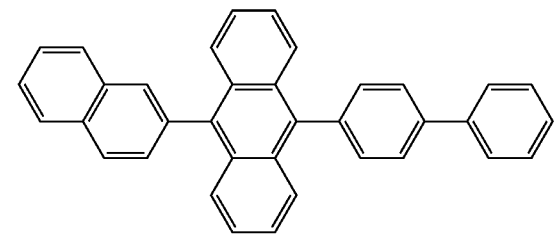
EM7
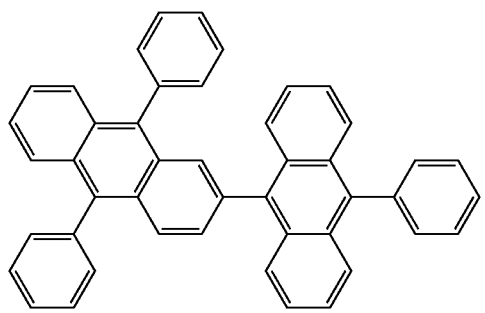
EM8
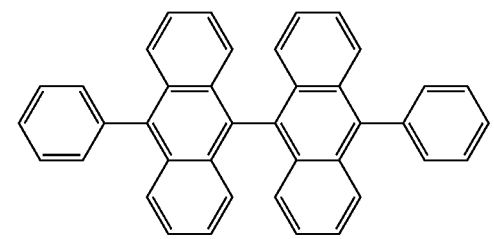
EM9
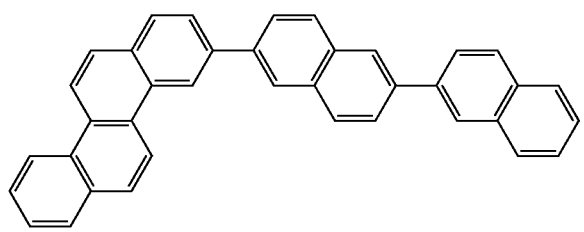
EM10
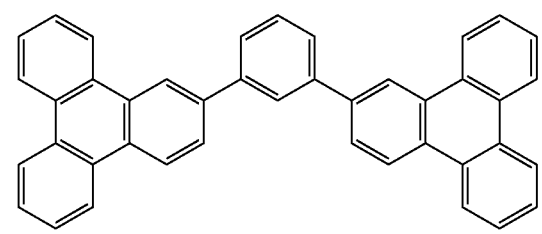
EM11
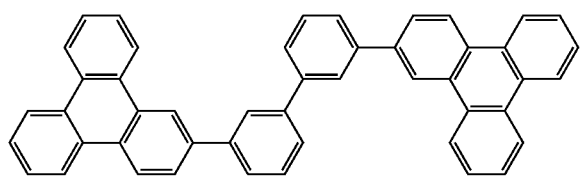
EM12
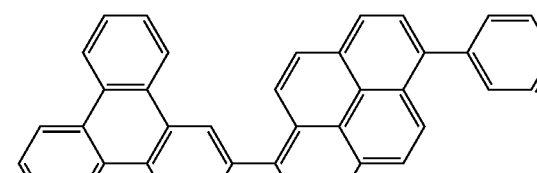
EM13
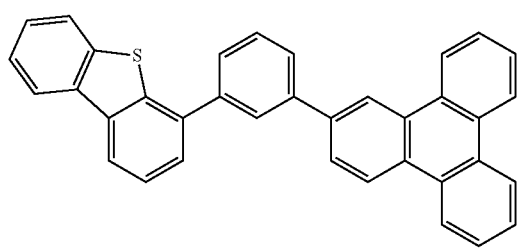
EM14
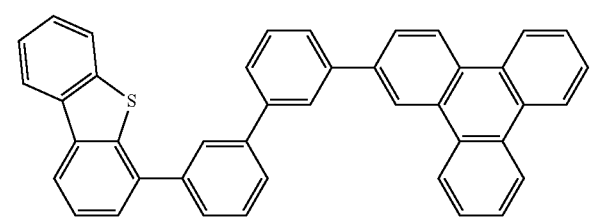
EM15
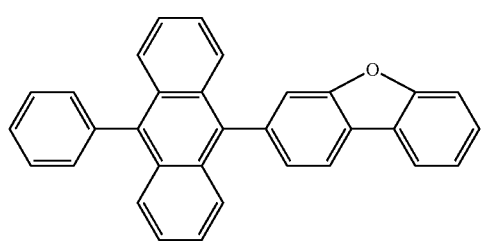

-continued
EM16
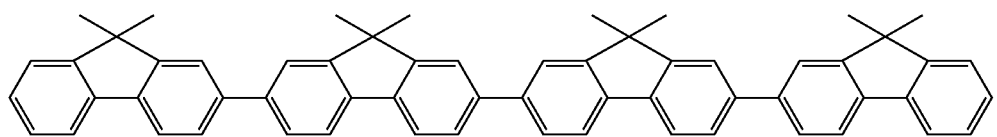
EM17
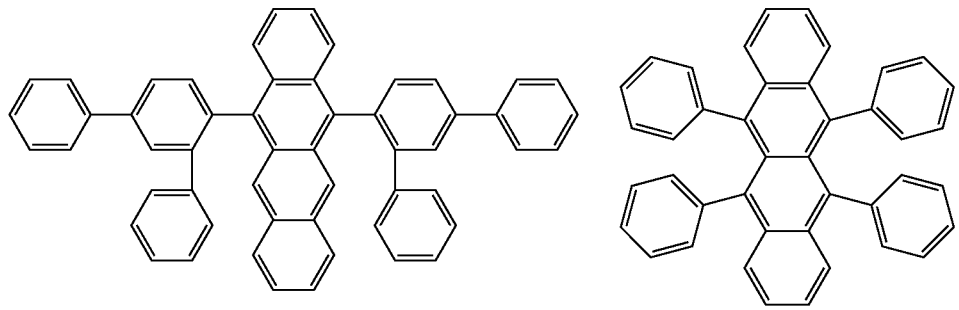
EM18
EM19
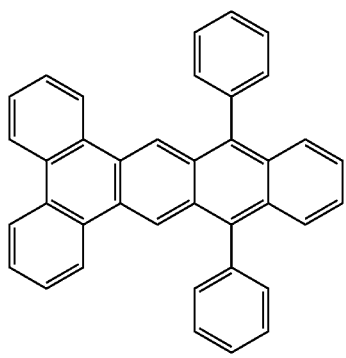
EM20
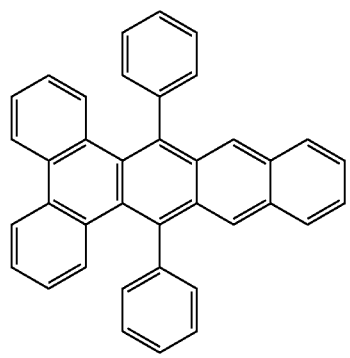
EM21
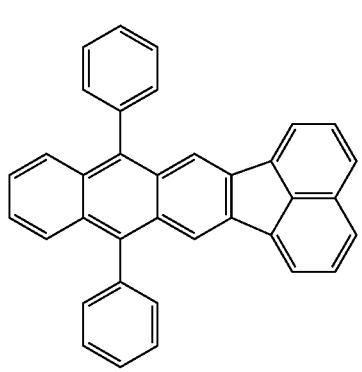
EM22
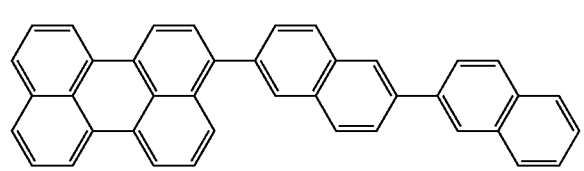
EM23
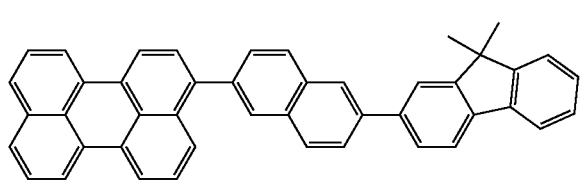
EM24
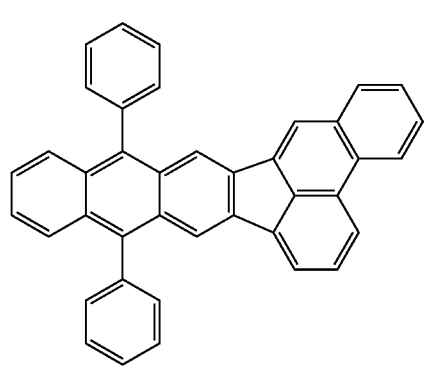

-continued
EM25
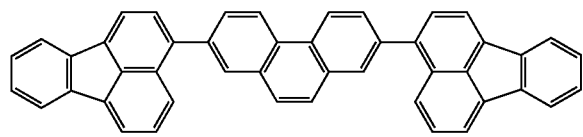
EM26
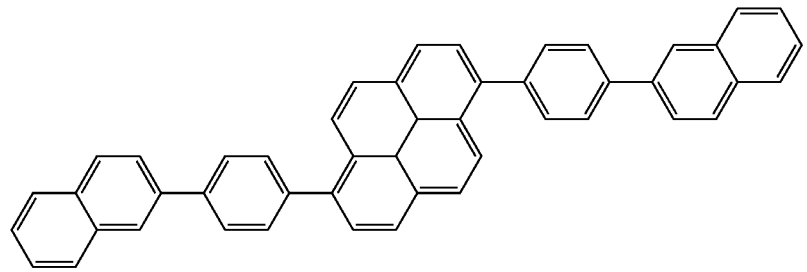
EM27
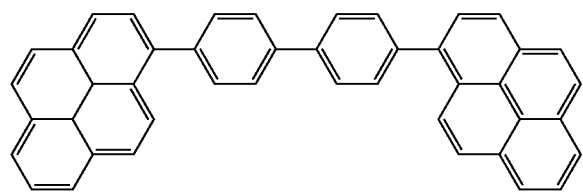
EM28
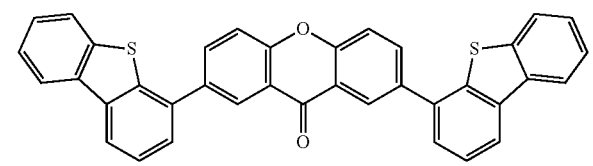
EM29
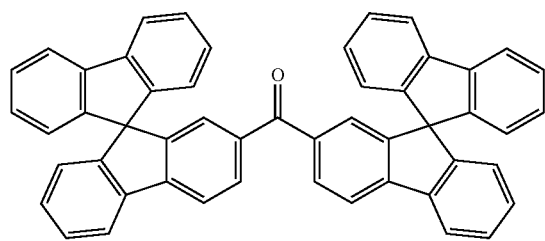
EM30
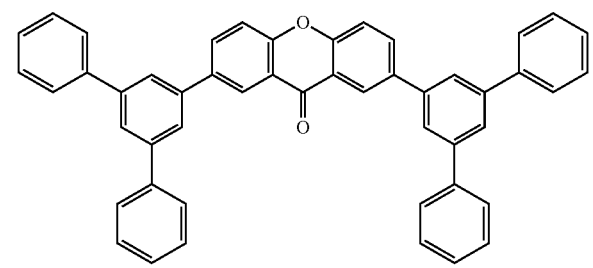
EM31
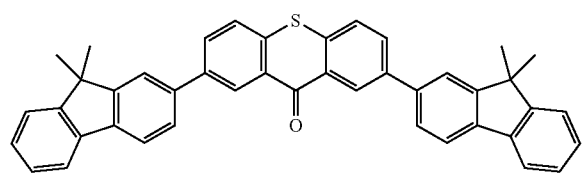
EM32
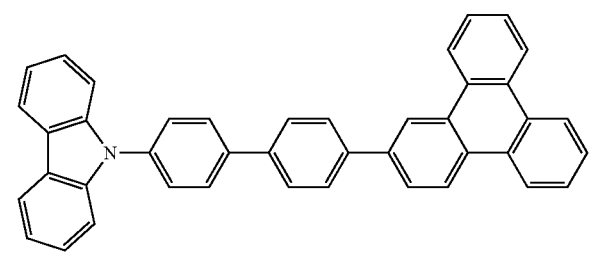
EM33
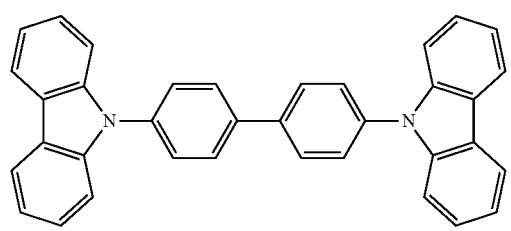
EM34
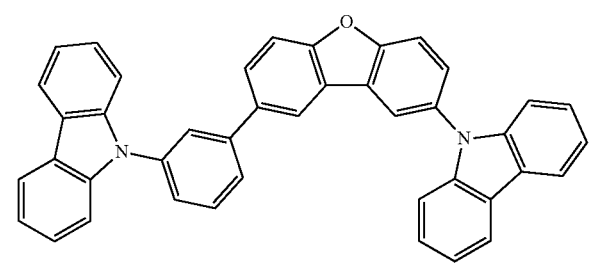

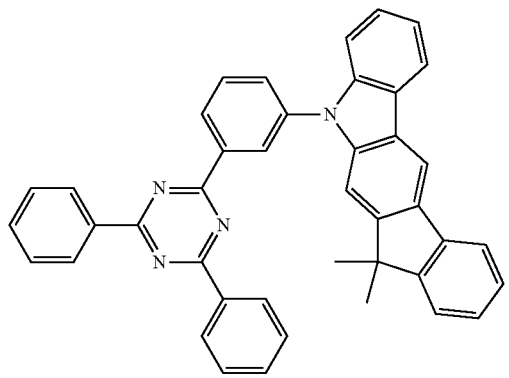

EM35

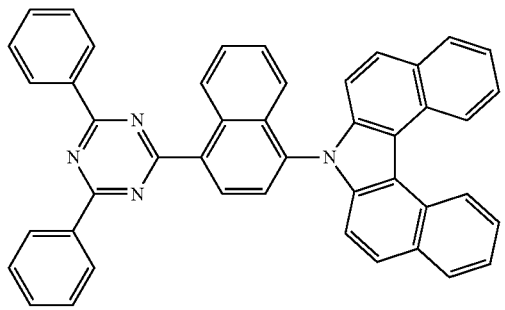

EM36

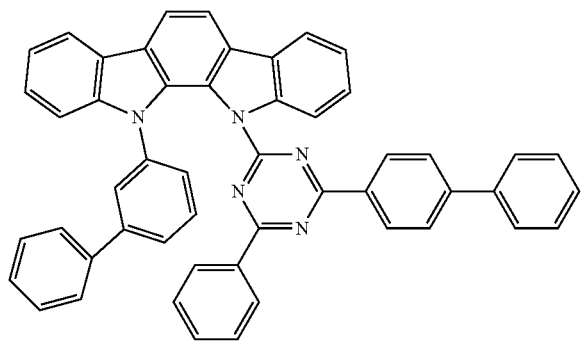

EM37

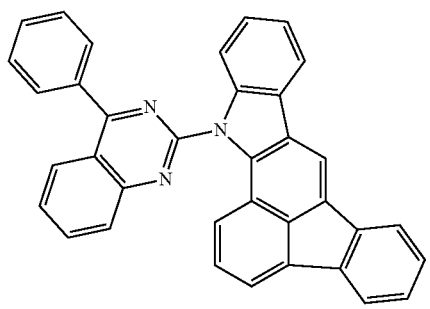

EM38

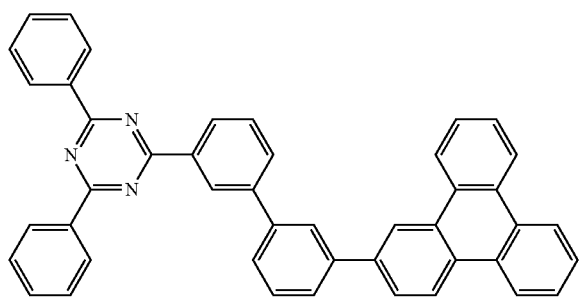

EM39

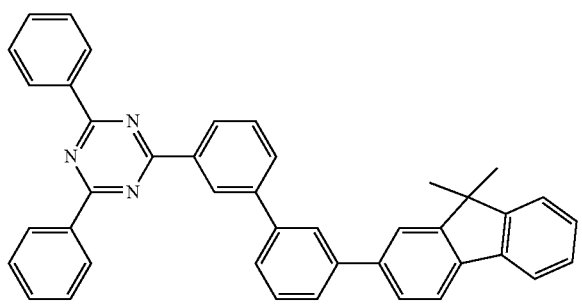

EM40

When the host material is a hydrocarbon compound, the compound according to the embodiment can easily trap electrons and holes to contribute to higher efficiency. The term "hydrocarbon compound" refers to a compound consisting of only carbon and hydrogen, and EM1 to EM12 and EM16 to EM27 are hydrocarbon compounds.

The electron transport material can be freely-selected from materials capable of transporting electrons injected from the cathode to the light-emitting layer and is selected in consideration of, for example, the balance with the hole mobility of the hole transport material. Examples of a material having the ability to transport electrons include oxadiazole derivatives, oxazole derivatives, pyrazine derivatives, triazole derivatives, triazine derivatives, quinoline derivatives, quinoxaline derivatives, phenanthroline derivatives, organoaluminum complexes, and condensed-ring compounds, such as fluorene derivatives, naphthalene derivatives, chrysene derivatives, and anthracene derivatives. The electron transport materials can be used for the hole-blocking layer. Non-limiting specific examples of a compound used as the electron transport material will be illustrated below.

ET1 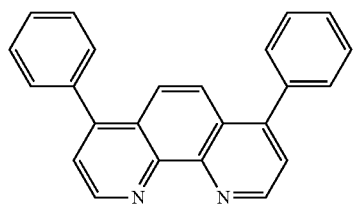
ET2 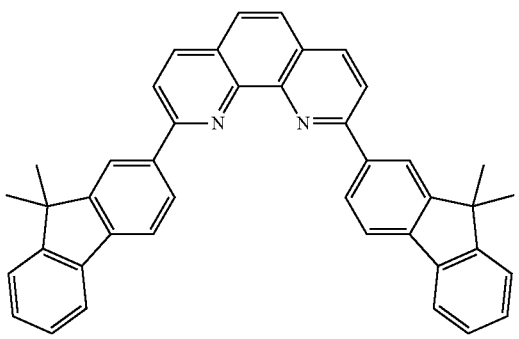
ET3 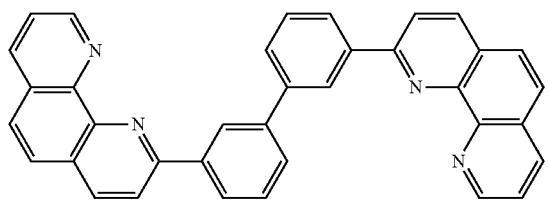
ET4 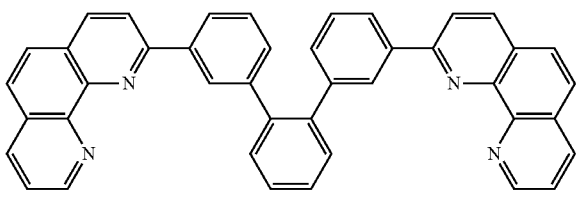
ET5 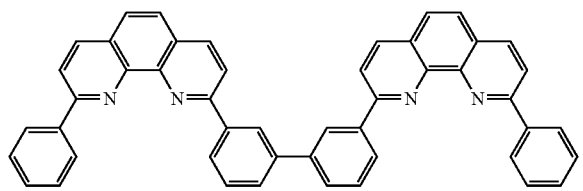
ET6 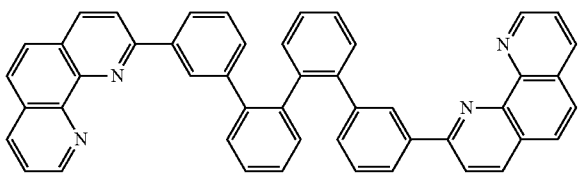
ET7 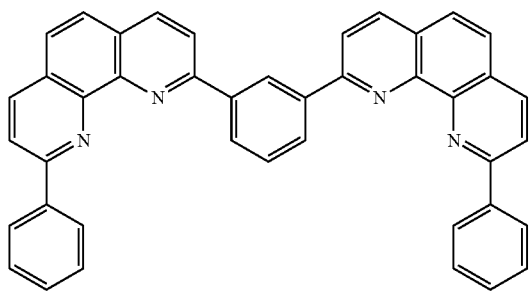
ET8 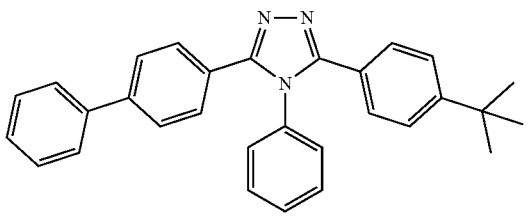
ET9 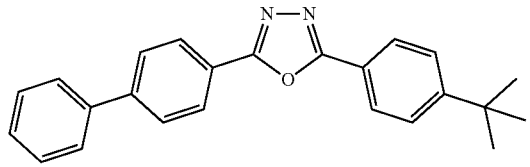
ET10 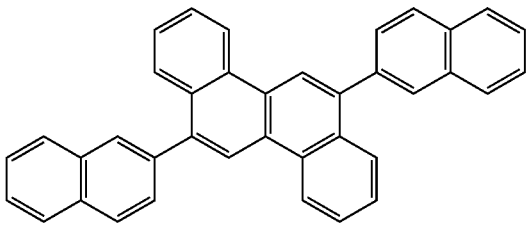
ET11 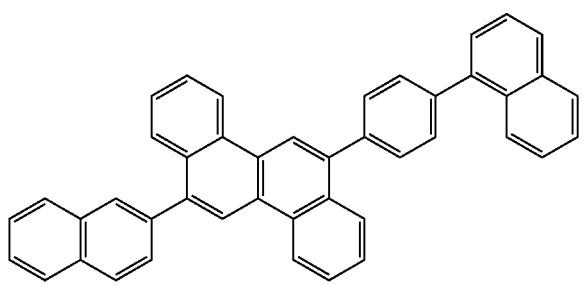
ET12 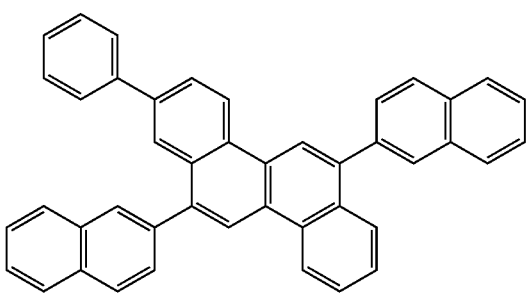

-continued
ET13
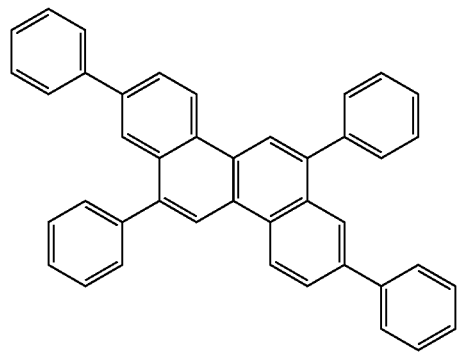
ET14
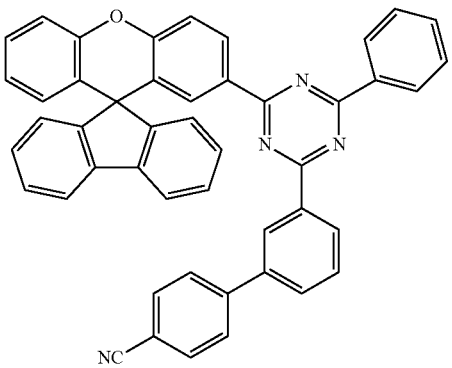
ET15
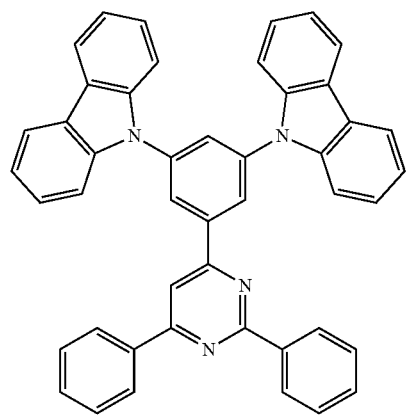
ET16
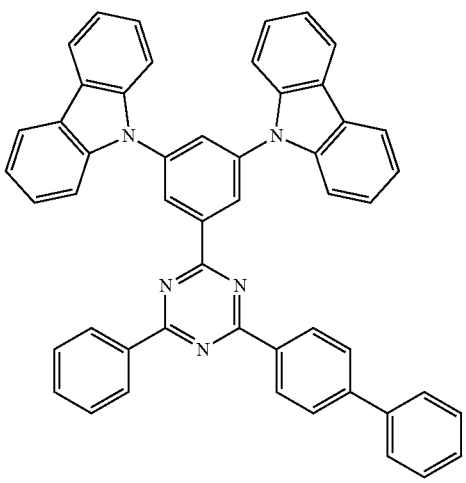
ET17
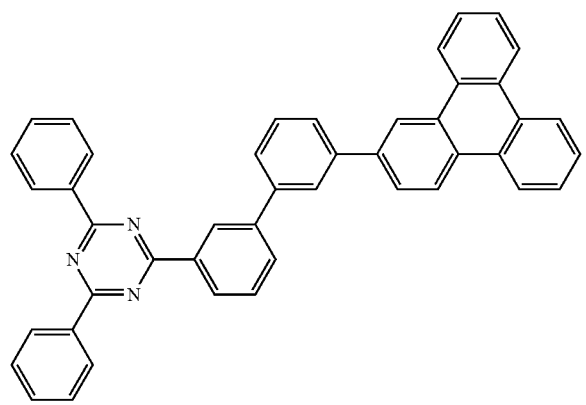
ET18
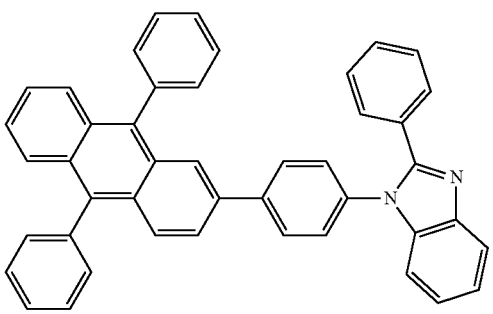
ET19
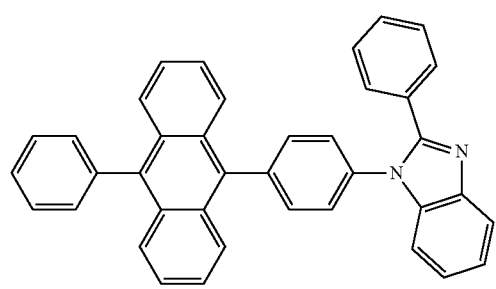
ET20
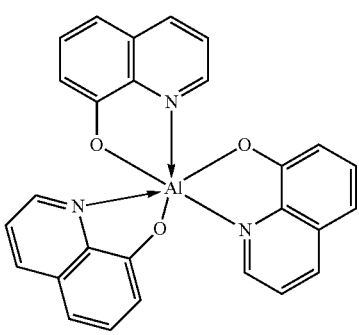

-continued
ET21
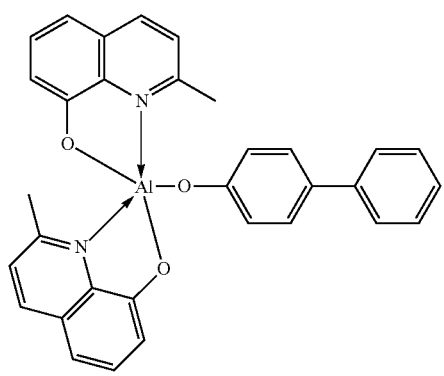
ET22
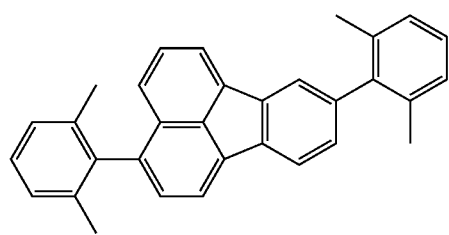
ET23
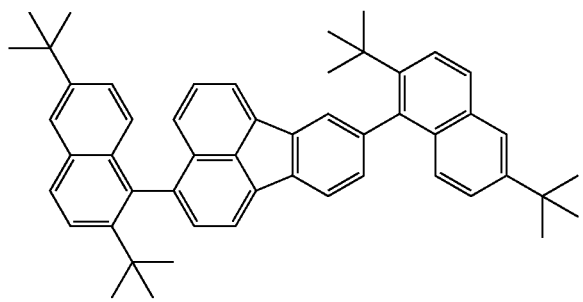
ET24
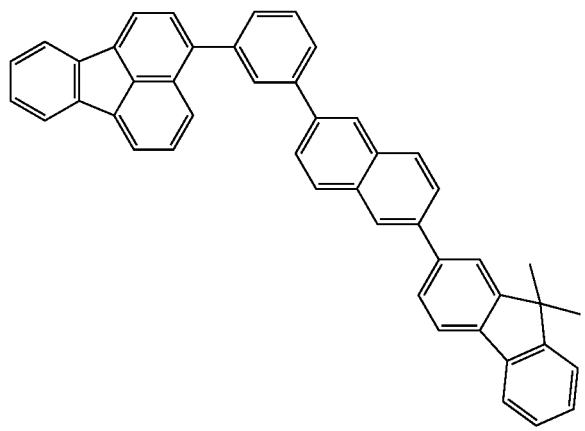
ET25
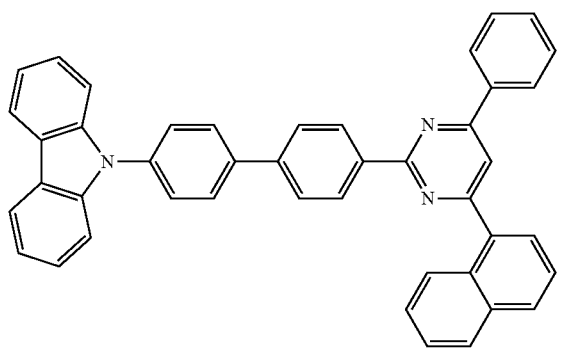
ET26
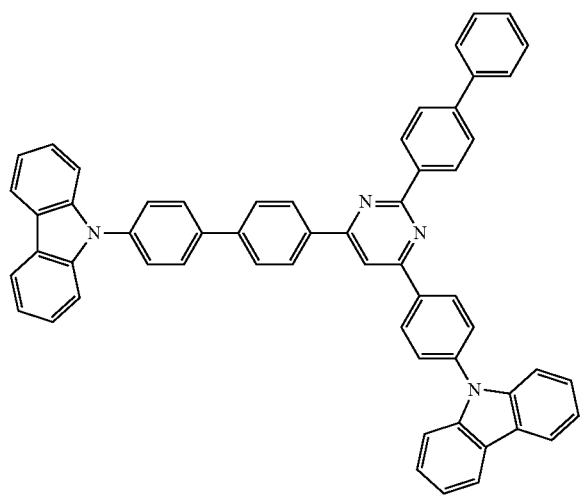

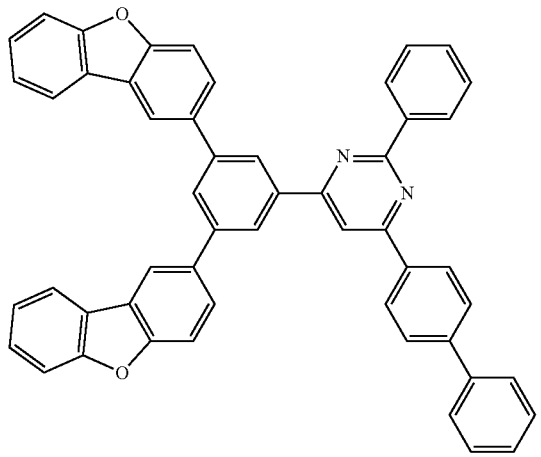

ET27

An electron injection material can be freely-selected from materials capable of easily injecting electrons from the cathode and is selected in consideration of, for example, the balance with the hole-injecting properties. As the organic compound, n-type dopants and reducing dopants are also included. Examples thereof include alkali metal-containing compounds, such as lithium fluoride, lithium complexes, such as lithium quinolinolate, benzimidazolidene derivatives, imidazolidene derivatives, fulvalene derivatives, and acridine derivatives.

Configuration of Organic Light-Emitting Device

The organic light-emitting device includes an insulating layer, a first electrode, an organic compound layer, and a second electrode over a substrate. A protective layer, a color filter, and a microlens may be disposed over the second electrode. In the case of disposing the color filter, a planarization layer may be disposed between the protective layer and the color filter. The planarization layer can be composed of, for example, an acrylic resin. The same applies when a planarization layer is provided between the color filter and the microlens.

Substrate

Examples of the substrate include silicon wafers, quartz substrates, glass substrates, resin substrates, and metal substrates. The substrate may include a switching element, such as transistor, a line, and an insulating layer thereon. Any material can be used for the insulating layer as long as a contact hole can be formed in such a manner that a line can be coupled to the first electrode and as long as insulation with a non-connected line can be ensured. Examples of the material that can be used include resins, such as polyimide, silicon oxide, and silicon nitride.

Electrode

A pair of electrodes can be used. The pair of electrodes may be an anode and a cathode.

In the case where an electric field is applied in the direction in which the organic light-emitting device emits light, an electrode having a higher potential is the anode, and the other is the cathode. It can also be said that the electrode that supplies holes to the light-emitting layer is the anode and that the electrode that supplies electrons is the cathode.

As the constituent material of the anode, a material having a work function as high as possible can be used. Examples of the material that can be used include elemental metals, such as gold, platinum, silver, copper, nickel, palladium, cobalt, selenium, vanadium, and tungsten, mixtures thereof, alloys of combinations thereof, and metal oxides, such as tin oxide, zinc oxide, indium oxide, indium-tin oxide (ITO), and indium-zinc oxide. Additionally, conductive polymers, such as polyaniline, polypyrrole, and polythiophene, may be used.

These electrode materials may be used alone or in combination of two or more. The anode may be formed of a single layer or multiple layers.

In the case where the anode is used as a reflective electrode, for example, chromium, aluminum, silver, titanium, tungsten, molybdenum, an alloy thereof, or a stack thereof may be used. It is also possible to use the above materials to function as a reflective film that does not have a role as an electrode. In the case where the anode is used as a transparent electrode, a transparent conductive oxide layer composed of, for example, indium-tin oxide (ITO) or indium-zinc oxide may be used; however, the anode is not limited thereto.

The electrodes may be formed by photolithography.

As the constituent material of the cathode, a material having a lower work function can be used. Examples thereof include elemental metals such as alkali metals, e.g., lithium, alkaline-earth metals, e.g., calcium, aluminum, titanium, manganese, silver, lead, and chromium, and mixtures thereof. Alloys of combinations of these elemental metals may also be used. For example, magnesium-silver, aluminum-lithium, aluminum-magnesium, silver-copper, and zinc-silver may be used. Metal oxides such as indium-tin oxide (ITO) may also be used. These electrode materials may be used alone or in combination of two or more. The cathode may have a single-layer structure or a multilayer structure. In particular, silver can be used. To reduce the aggregation of silver, a silver alloy can be used. Any alloy ratio may be used as long as the aggregation of silver can be reduced. The ratio of silver to another metal may be, for example, 1:1 or 3:1.

A top emission device may be provided using the cathode formed of a conductive oxide layer composed of, for example, ITO. A bottom emission device may be provided using the cathode formed of a reflective electrode composed of, for example, aluminum (Al). The cathode is not particularly limited. Any method for forming the cathode may be used. For example, a direct-current or alternating-current sputtering technique can be employed because good film coverage is obtained and thus the resistance is easily reduced.

Organic Compound Layer

The organic compound layer may be formed of a single layer or multiple layers. When multiple layers are present, they may be referred to as a hole injection layer, a hole transport layer, an electron-blocking layer, a light-emitting layer, a hole-blocking layer, an electron transport layer, or an electron injection layer in accordance with their functions. The organic compound layer is mainly composed of an organic compound, and may contain inorganic atoms and an inorganic compound. For example, the organic compound layer may contain, for example, copper, lithium, magnesium, aluminum, iridium, platinum, molybdenum, or zinc. The organic compound layer may be disposed between the first electrode and the second electrode, and may be arranged in contact with the first electrode and the second electrode.

The organic compound layer, such as the hole injection layer, the hole transport layer, the electron-blocking layer, the light-emitting layer, the hole-blocking layer, the electron transport layer, or the electron injection layer, included in the organic light-emitting device according to an embodiment of the present disclosure is formed by a method described below.

For the organic compound layer included in the organic light-emitting device according to an embodiment of the present disclosure, a dry process, such as a vacuum evaporation method, an ionized evaporation method, sputtering, or plasma, may be employed. Alternatively, instead of the dry process, it is also possible to employ a wet process in which a material is dissolved in an appropriate solvent and then a film is formed by a known coating method, such as spin coating, dipping, a casting method, a Langmuir-Blodgett (LB) technique, or an ink jet method.

In the case where the layer is formed by, for example, the vacuum evaporation method or the solution coating method, crystallization and so forth are less likely to occur, and good stability with time is obtained. In the case of forming a film by the coating method, the film may be formed in combination with an appropriate binder resin.

Non-limiting examples of the binder resin include poly (vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

These binder resins may be used alone as a homopolymer or copolymer or in combination as a mixture of two or more. Furthermore, additives, such as a known plasticizer, antioxidant, and ultraviolet absorber, may be used, as needed.

Protective Layer

A protective layer may be disposed on the second electrode. For example, a glass member provided with a moisture absorbent can be bonded to the second electrode to reduce the entry of, for example, water into the organic compound layer, thereby reducing the occurrence of display defects. In another embodiment, a passivation film composed of, for example, silicon nitride may be disposed on the second electrode to reduce the entry of, for example, water into the organic compound layer. For example, after the formation of the second electrode, the substrate may be transported to another chamber without breaking the vacuum, and a silicon nitride film having a thickness of 2 µm may be formed by a chemical vapor deposition (CVD) method to provide a protective layer. After the film deposition by the CVD method, a protective layer may be formed by an atomic layer deposition (ALD) method. Non-limiting examples of the material of the film formed by the ALD method may include silicon nitride, silicon oxide, and aluminum oxide. Silicon nitride may be deposited by the CVD method on the film formed by the ALD method. The film formed by the ALD method may have a smaller thickness than the film formed by the CVD method. Specifically, the thickness may be 50% or less, even 10% or less.

Color Filter

A color filter may be disposed on the protective layer. For example, a color filter may be disposed on another substrate in consideration of the size of the organic light-emitting device and bonded to the substrate provided with the organic light-emitting device. A color filter may be formed by patterning on the protective layer using photolithography. The color filter may be composed of a polymer.

Planarization Layer

A planarization layer may be disposed between the color filter and the protective layer. The planarization layer is provided for the purpose of reducing the unevenness of the layer underneath. The planarization layer may be referred to as a "material resin layer" without limiting its purpose. The planarization layer may be composed of an organic compound. A low- or high-molecular-weight organic compound may be used. A high-molecular-weight organic compound can be used.

The planarization layers may be disposed above and below (or on) the color filter and may be composed of the same or different materials. Specific examples thereof include poly(vinyl carbazole) resins, polycarbonate resins, polyester resins, acrylonitrile butadiene styrene (ABS) resins, acrylic resins, polyimide resins, phenolic resins, epoxy resins, silicone resins, and urea resins.

Microlens

The organic light-emitting device or an organic light-emitting apparatus may include an optical component, such as a microlens, on the outgoing light side. The microlens can be composed of, for example, an acrylic resin or an epoxy resin. The microlens may be used to increase the amount of light emitted from the organic light-emitting device or the organic light-emitting apparatus and to control the direction of the light emitted. The microlens may have a hemispherical shape. In the case of a hemispherical shape, among tangents to the hemisphere, there is a tangent parallel to the insulating layer. The point of contact of the tangent with the hemisphere is the vertex of the microlens. The vertex of the microlens can be determined in the same way for any cross-sectional view. That is, among the tangents to the semicircle of the microlens in the cross-sectional view, there is a tangent parallel to the insulating layer, and the point of contact of the tangent with the semicircle is the vertex of the microlens.

The midpoint of the microlens can be defined. In the cross section of the microlens, when a segment is hypothetically drawn from the point where an arc shape ends to the point where another arc shape ends, the midpoint of the segment can be referred to as the midpoint of the microlens. The cross section to determine the vertex and midpoint may be a cross section perpendicular to the insulating layer.

Opposite Substrate

An opposite substrate may be disposed on the planarization layer. The opposite substrate is disposed at a position corresponding to the substrate described above and thus is called an opposite substrate. The opposite substrate may be composed of the same material as the substrate described above. When the above-described substrate is referred to as a first substrate, the opposing substrate may be referred to as a second substrate.

Pixel Circuit

An organic light-emitting apparatus including organic light-emitting devices may include pixel circuits coupled to the organic light-emitting devices. Each of the pixel circuits may be of an active matrix type, which independently controls the emission of first and second light-emitting devices. The active matrix type circuit may be voltage programming or current programming. A driving circuit includes the pixel circuit for each pixel. The pixel circuit may include a transistor to control the luminance of the light-emitting device, a transistor to control the timing of the light emission, a capacitor to retain the gate voltage of the transistor to control the luminance, and a transistor to connect to GND without using the light-emitting device.

The intensity of the drive current may be determined in accordance with the size of the light-emitting region. Specifically, when the first and second light-emitting devices emit light with the same luminance, the current flowing through the first light-emitting device may be lower than the current flowing through the second light-emitting device. The reason for this is that the current required may be low because the light-emitting region is small.

Pixel

An organic light-emitting apparatus including an organic light-emitting device may include multiple pixels. Each pixel includes subpixels configured to emit colors different from each other. The subpixels may have respective red, green, and blue (RGB) emission colors.

Light emerges from a region of the pixel, also called a pixel aperture. This region is the same as a first region. The pixel aperture may be 15 μm or less, and may be 5 μm or more. More specifically, the pixel aperture may be, for example, 11 μm, 9.5 μm, 7.4 μm, or 6.4 μm. The distance between subpixels may be 10 μm. Specifically, the distance may be 8 μm, 7.4 μm, or 6.4 μm.

The pixels may be arranged in a known pattern in plan view. For example, a stripe pattern, a delta pattern, a Pen Tile matrix pattern, or the Bayer pattern may be used. The shape of each subpixel in plan view may be any known shape. Examples of the shape of the subpixel include quadrilaterals, such as rectangles and rhombi, and hexagons. Of course, if the shape is close to a rectangle, rather than an exact shape, it is included in the rectangle. The shape of the subpixel and the pixel arrangement can be used in combination.

Application of Organic Light-Emitting Device According to Embodiment of the Present Disclosure The organic light-emitting device according to an embodiment can be used as a component member of a display apparatus or lighting apparatus. Other applications include exposure light sources for electrophotographic image-forming apparatuses, backlights for liquid crystal displays, and light-emitting devices including white-light sources and color filters.

The display apparatus may be an image information-processing unit having an image input unit that receives image information from an area or linear CCD sensor, a memory card, or any other source, an information-processing unit that processes the input information, and a display unit that displays the input image. The display apparatus includes multiple pixels, and at least one of the multiple pixels may include the organic light-emitting device according to the embodiment and a transistor coupled to the organic light-emitting device.

The display unit of an image pickup apparatus or an inkjet printer may have a touch panel function. The driving mode of the touch panel function may be, but is not particularly limited to, an infrared mode, an electrostatic capacitance mode, a resistive film mode, or an electromagnetic inductive mode. The display apparatus may also be used for a display unit of a multifunction printer.

Figure 4A:
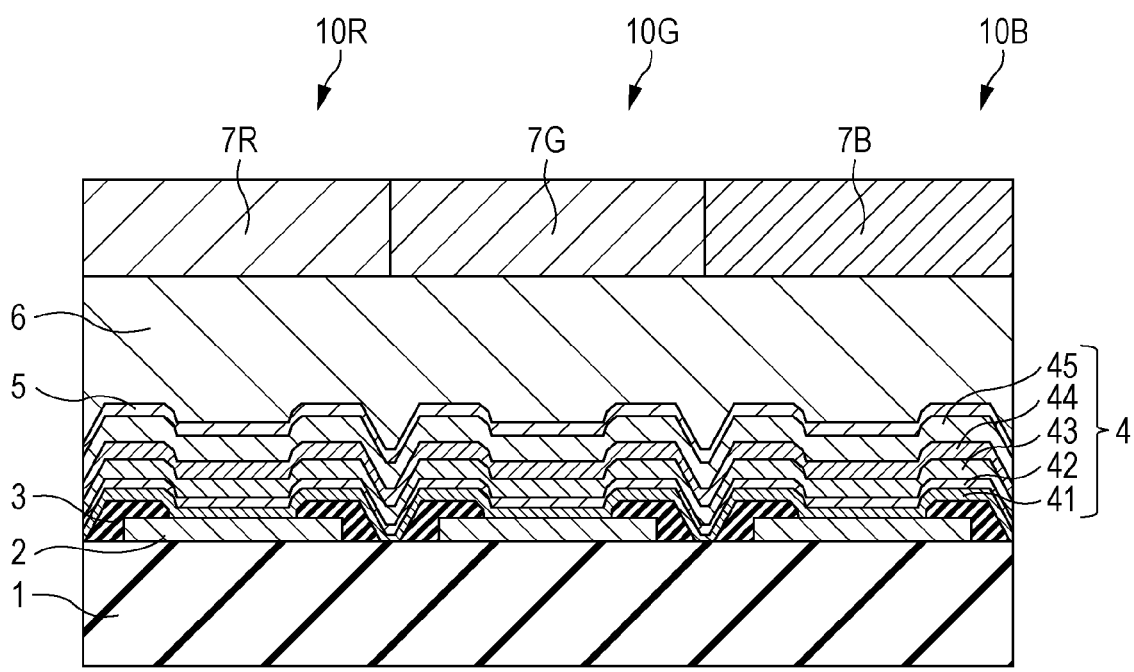
FIG. 4A is a schematic cross-sectional view of an example of pixels of a display apparatus according to an embodiment of the present disclosure.
Figure 4B:
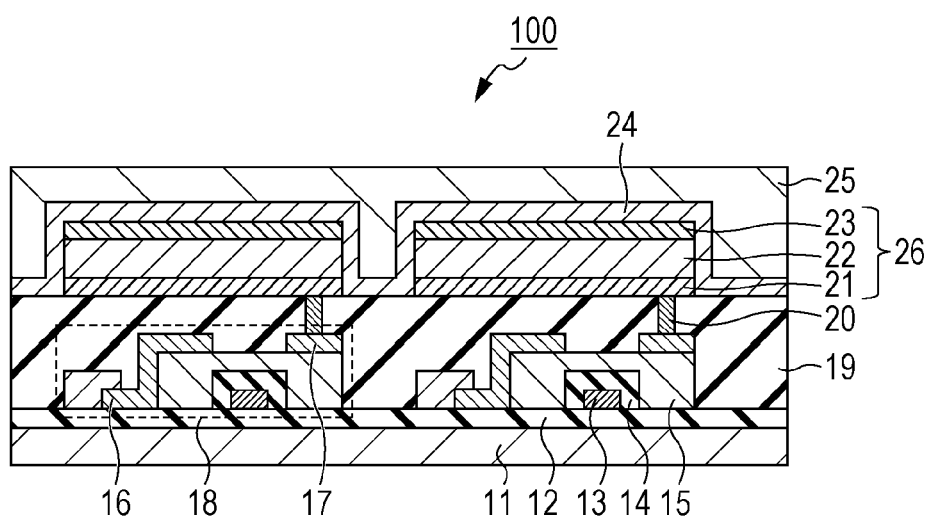
FIG. 4B is a schematic cross-sectional view of an example of a display apparatus including organic light-emitting devices according to an embodiment of the present disclosure.

The following describes a display apparatus according to the embodiment with reference to the attached drawings. FIGS. 4A and 4B are each a schematic cross-sectional view of an example of a display apparatus including organic light-emitting devices and transistors coupled to the respective organic light-emitting devices. Each of the transistors is an example of an active element. The transistors may be thin-film transistors (TFTs).

FIG. 4A is an example of pixels that are components of the display apparatus according to the embodiment. Each of the pixels includes subpixels 10. The subpixels are separated into 10R, 10G, and 10B according to their light emission. The emission color may be distinguished based on the wavelength of light emitted from the light-emitting layer. Alternatively, light emitted from the subpixels may be selectively transmitted or color-converted with, for example, a color filter. Each subpixels 10 includes a reflective electrode serving as a first electrode 2, an insulating layer 3 covering the edge of the first electrode 2, an organic compound layer 4 covering the first electrode 2 and the insulating layer 3, a transparent electrode serving as a second electrode 5, a protective layer 6, and a color filter 7 over an interlayer insulating layer 1.

The transistors and capacitive elements may be disposed under or in the interlayer insulating layer 1.

Each transistor may be electrically coupled to a corresponding one of the first electrodes 2 through a contact hole (not illustrated).

The insulating layer 3 is also called a bank or pixel separation film. The insulating layer 3 covers the edge of each first electrode 2 and surrounds the first electrode 2. Portions that are not covered with the insulating layer 3 are in contact with the organic compound layer 4 and serve as light-emitting regions.

The organic compound layer 4 includes a hole injection layer 41, a hole transport layer 42, a first light-emitting layer 43, a second light-emitting layer 44, and an electron transport layer 45.

The second electrode 5 may be a transparent electrode, a reflective electrode, or a semi-transparent electrode.

The protective layer 6 reduces the penetration of moisture into the organic compound layer 4. Although the protective layer 6 is illustrated as a single layer, the protective layer 6 may include multiple layers, and each layer may be an inorganic compound layer or an organic compound layer.

The color filter 7 is separated into 7R, 7G, and 7B according to its color. The color filter 7 may be disposed on a planarization film (not illustrated). A resin protective layer (not illustrated) may be disposed on the color filter 7. The color filter 7 may be disposed on the protective layer 6. Alternatively, the color filter 7 may be disposed on an opposite substrate, such as a glass substrate, and then bonded.

A display apparatus 100 illustrated in FIG. 4B includes organic light-emitting devices 26 and TFTs 18 as an example of transistors. A substrate 11 composed of a material, such as glass or silicon is provided, and an insulating layer 12 is disposed thereon. Active elements, such as the TFTs 18, are disposed on the insulating layer 12. The gate electrode 13, the gate insulating film 14, and the semiconductor layer 15 of each of the active elements are disposed thereon. Each TFT 18 further includes a drain electrode 16 and a source electrode 17. The TFTs 18 are overlaid with an insulating film 19. Anode 21 included in the organic light-emitting devices 26 is coupled to the source electrodes 17 through contact holes 20 provided in the insulating film 19.

The mode of electrical connection between the electrodes (anode 21 and cathode 23) included in each organic light-emitting device 26 and the electrodes (source electrode 17 and drain electrode 16) included in a corresponding one of the TFTs 18 is not limited to the mode illustrated in FIG. 4B. That is, it is sufficient that any one of the anode 21 and the cathode 23 is electrically coupled to any one of the source electrode 17 and the drain electrode 16 of the TFT 18. The term "TFT" refers to a thin-film transistor.

In the display apparatus 100 illustrated in FIG. 4B, although each organic compound layer 22 is illustrated as a single layer, the organic compound layer 22 may include multiple layers. To reduce the deterioration of the organic light-emitting devices 26, a first protective layer 24 and a second protective layer 25 are disposed on the cathodes 23.

In the display apparatus 100 illustrated in FIG. 4B, although the transistors are used as switching devices, other switching devices may be used instead.

The transistors used in the display apparatus 100 illustrated in FIG. 4B are not limited to transistors using a single-crystal silicon wafer, but may also be thin-film transistors including active layers on the insulating surface of a substrate. Examples of the material of the active layers include single-crystal silicon, non-single-crystal silicon, such as amorphous silicon and microcrystalline silicon; and non-single-crystal oxide semiconductors, such as indium zinc oxide and indium gallium zinc oxide. Thin-film transistors are also called TFT elements.

The transistors in the display apparatus 100 illustrated in FIG. 4B may be formed in the substrate, such as a Si substrate. The expression "formed in the substrate" indicates that the transistors are produced by processing the substrate, such as a Si substrate. In the case where the transistors are formed in the substrate, the substrate and the transistors can be deemed to be integrally formed.

In the organic light-emitting device according to the embodiment, the luminance is controlled by the TFT devices, which are an example of switching devices; thus, an image can be displayed at respective luminance levels by arranging multiple organic light-emitting devices in the plane. The switching devices according to the embodiment are not limited to the TFT devices and may be low-temperature polysilicon transistors or active-matrix drivers formed on a substrate such as a Si substrate. The expression "on a substrate" can also be said to be "in the substrate". Whether transistors are formed in the substrate or TFT devices are used is selected in accordance with the size of a display unit. For example, in the case where the display unit has a size of about 0.5 inches, organic light-emitting devices can be disposed on a Si substrate.

Figure 5:
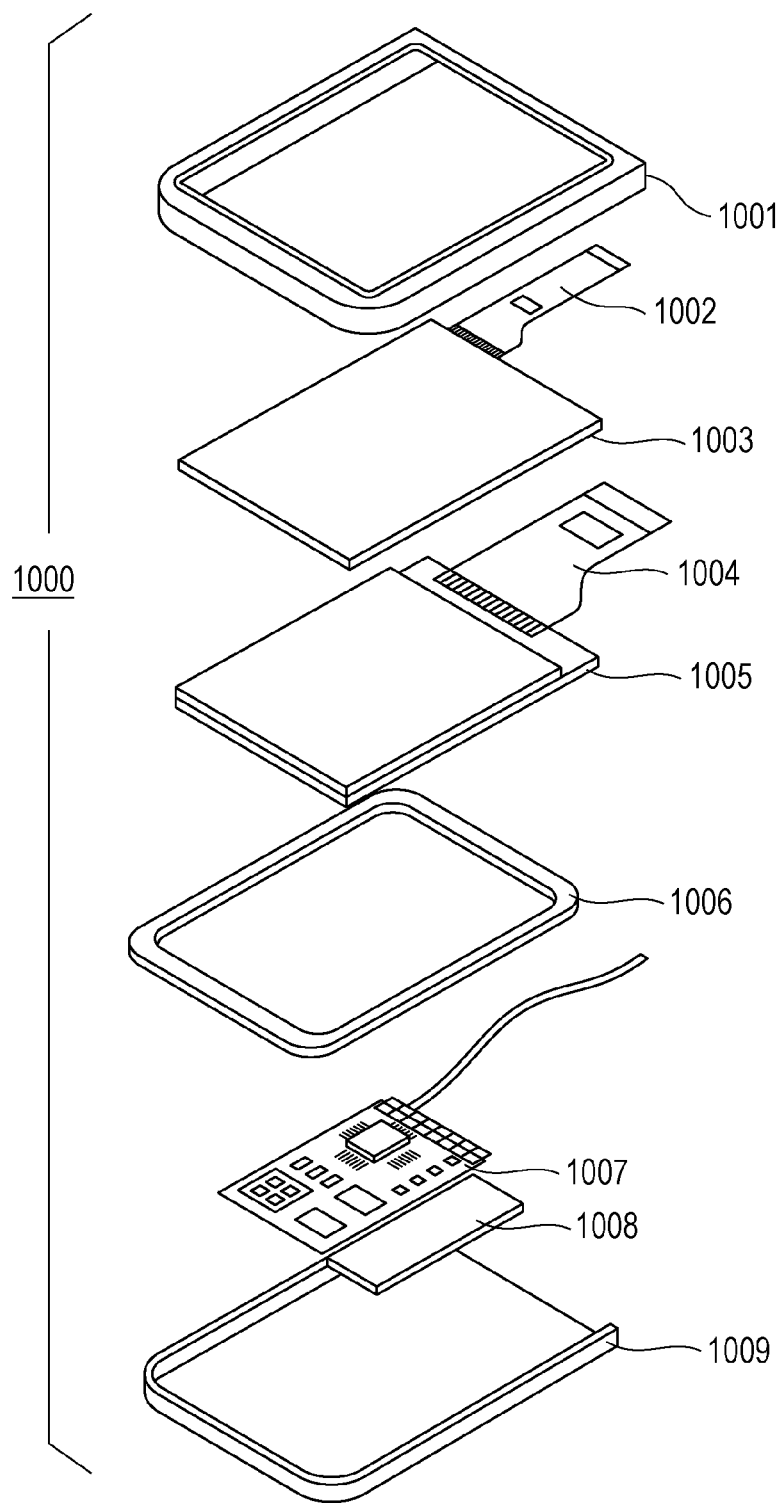
FIG. 5 is a schematic view of an example of a display apparatus according to an embodiment of the present disclosure.

FIG. 5 is a schematic view illustrating an example of a display apparatus according to the embodiment. A display apparatus 1000 may include a touch panel 1003, a display panel 1005, a frame 1006, a circuit substrate 1007, and a battery 1008 disposed between an upper cover 1001 and a lower cover 1009. The touch panel 1003 and the display panel 1005 are coupled to flexible printed circuits FPCs 1002 and 1004, respectively. The circuit substrate 1007 includes printed transistors. The battery 1008 need not be provided unless the display apparatus is a portable apparatus. The battery 1008 may be disposed at a different position even if the display apparatus is a portable apparatus.

The display apparatus according to the embodiment may include a color filter having red, green, and blue portions. In the color filter, the red, green, and blue portions may be arranged in a delta arrangement.

The display apparatus according to the embodiment may be used for the display unit of a portable terminal. In that case, the display apparatus may have both a display function and an operation function. Examples of the portable terminal include mobile phones such as smartphones, tablets, and head-mounted displays.

The display apparatus according to the embodiment may be used for a display unit of an image pickup apparatus including an optical unit including multiple lenses and an image pickup device that receives light passing through the optical unit. The image pickup apparatus may include a display unit that displays information acquired by the image pickup device. The display unit may be a display unit exposed to the outside of the image pickup apparatus or a display unit disposed in a finder. The image pickup apparatus may be a digital camera or a digital camcorder.

Figure 6A:
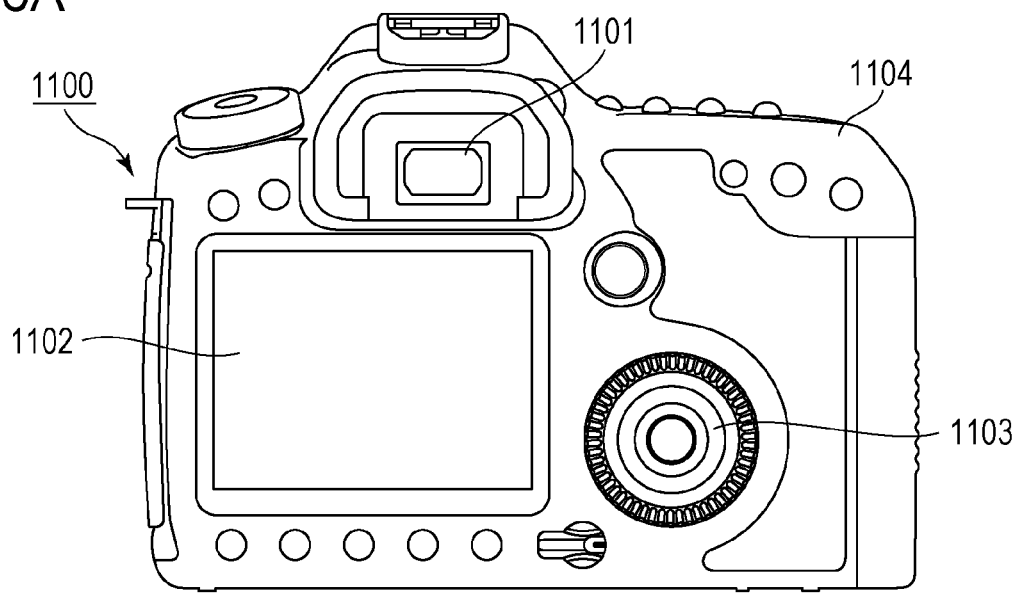
FIG. 6A is a schematic view of an example of an image pickup apparatus according to an embodiment of the present disclosure.

FIG. 6A is a schematic view illustrating an example of an image pickup apparatus according to the embodiment. An image pickup apparatus 1100 may include a viewfinder 1101, a rear display 1102, an operation unit 1103, and a housing 1104. The viewfinder 1101 may include the display apparatus according to the embodiment. In this case, the display apparatus may display environmental information, imaging instructions, and so forth in addition to an image to be captured. The environmental information may include, for example, the intensity of external light, the direction of external light, the moving speed of a subject, and the possibility that a subject is shielded by a shielding material.

The timing suitable for imaging is only for a short time; thus, the information may be displayed as soon as possible. The display apparatus including the organic light-emitting device can be used more suitably than liquid crystal displays because the organic light-emitting device has a fast response time. The display apparatus including the organic light-emitting device can be used more suitably than liquid crystal displays for such apparatuses required to have a high display speed.

The image pickup apparatus 1100 includes an optical unit (not illustrated). The optical unit includes multiple lenses and is configured to form an image on an image pickup device in the housing 1104. The relative positions of the multiple lenses can be adjusted to adjust the focal point. This operation can also be performed automatically. The image pickup apparatus may translate to a photoelectric conversion apparatus. Examples of an image capturing method employed in the photoelectric conversion apparatus may include a method for detecting a difference from the previous image and a method of cutting out an image from images always recorded, instead of sequentially capturing images.

Figure 6B:
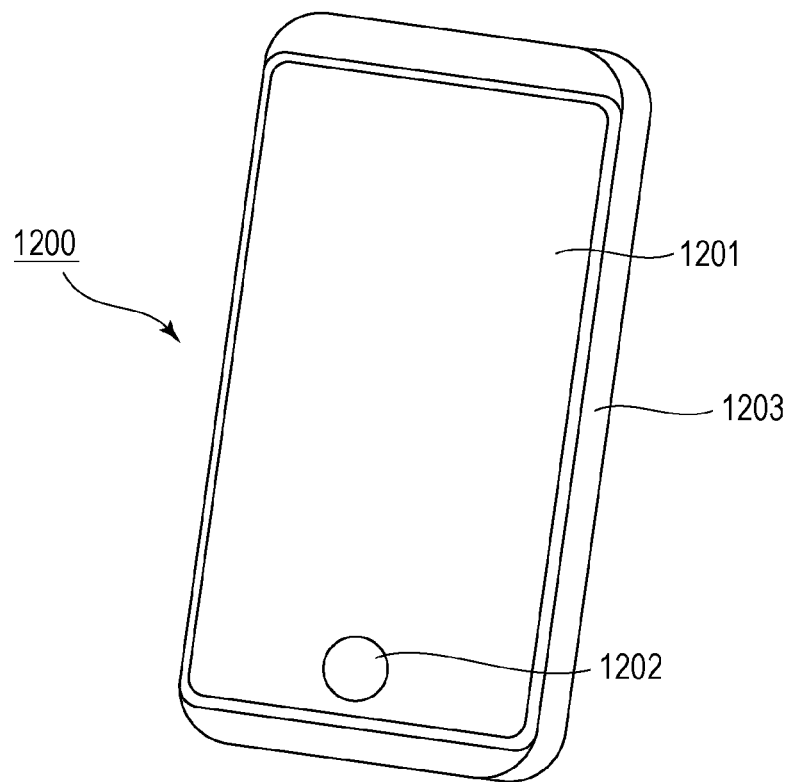
FIG. 6B is a schematic view of an example of an electronic apparatus according to an embodiment of the present disclosure.

FIG. 6B is a schematic view illustrating an example of an electronic apparatus according to the embodiment. An electronic apparatus 1200 includes a display unit 1201, an operation unit 1202, and a housing 1203. The housing 1203 may accommodate a circuit, a printed circuit board including the circuit, a battery, and a communication unit. The operation unit 1202 may be a button or a touch-screen-type reactive unit. The operation unit 1202 may be a biometric recognition unit that recognizes a fingerprint to release the lock or the like. An electronic apparatus having a communication unit can also be referred to as a communication apparatus. The electronic apparatus 1200 may further have a camera function by being equipped with a lens and an image pickup device. An image captured by the camera function is displayed on the display unit 1201. Examples of the electronic apparatus 1200 include smartphones and notebook computers.

Figure 7A:
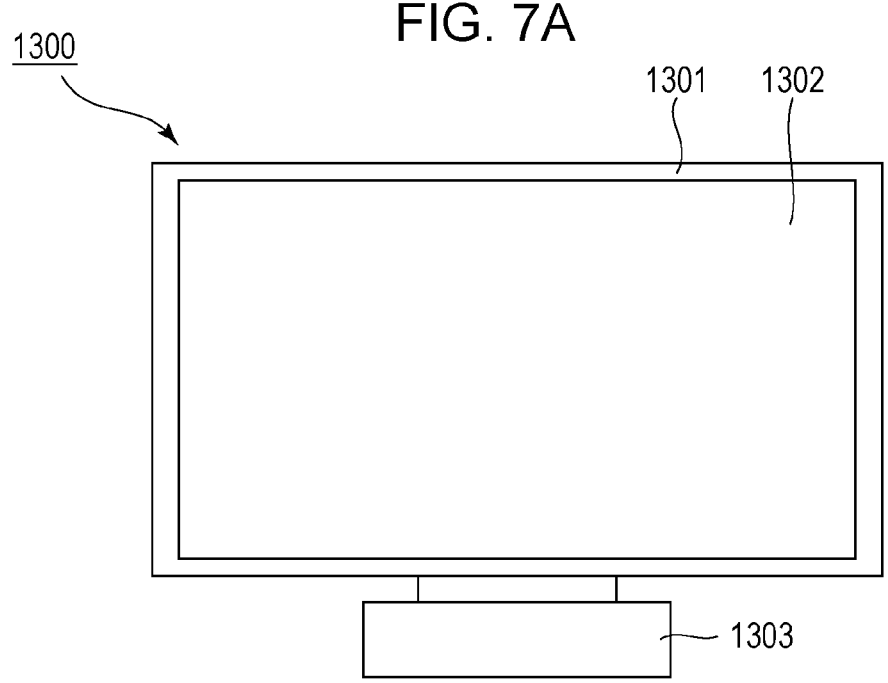
FIG. 7A is a schematic view of an example of a display apparatus according to an embodiment of the present disclosure.

FIG. 7A is a schematic view illustrating an example of the display apparatus according to the embodiment. FIG. 7A illustrates a display apparatus, such as a television monitor or a PC monitor. A display apparatus 1300 includes a frame 1301 and a display unit 1302. The light-emitting device according to the embodiment may be used for the display unit 1302. The display apparatus 1300 includes a base 1303 that supports the frame 1301 and the display unit 1302. The base 1303 is not limited to the structure illustrated in FIG. 7A. The lower side of the frame 1301 may also serve as a base. The frame 1301 and the display unit 1302 may be curved. These may have a radius of curvature of 5,000 mm or more and 6,000 mm or less.

Figure 7B:
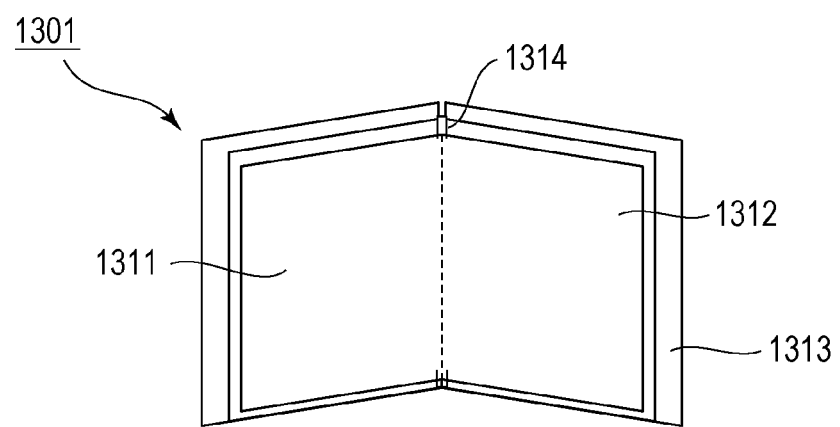
FIG. 7B is a schematic view of an example of a foldable display apparatus.

FIG. 7B is a schematic view illustrating another example of a display apparatus according to the embodiment. A display apparatus 1310 illustrated in FIG. 7B can be folded and is what is called a foldable display apparatus. The display apparatus 1310 includes a first display portion 1311, a second display portion 1312, a housing 1313, and an inflection point 1314. The first display portion 1311 and the second display portion 1312 may include the light-emitting device according to the embodiment. The first display portion 1311 and the second display portion 1312 may be a single, seamless display apparatus. The first display portion 1311 and the second display portion 1312 can be divided from each other at the inflection point. The first display portion 1311 and the second display portion 1312 may display different images. Alternatively, a single image may be displayed in the first and second display portions.

Figure 8A:
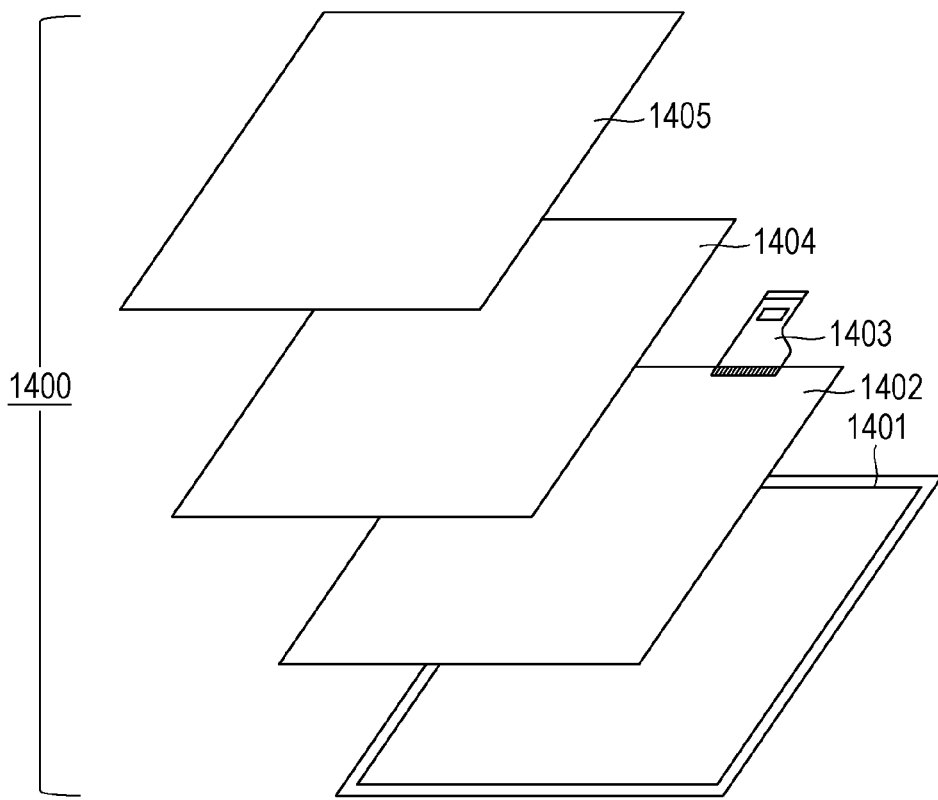
FIG. 8A is a schematic view of an example of a lighting apparatus according to an embodiment of the present disclosure.

FIG. 8A is a schematic view illustrating an example of a lighting apparatus according to the embodiment. A lighting apparatus 1400 may include a housing 1401, a light source 1402, a circuit board 1403, an optical filter 1404 that transmits light emitted from the light source 1402, and a light diffusion unit 1405. The light source 1402 may include an organic light-emitting device according to the embodiment. The optical filter 1404 may be a filter that improves the color rendering properties of the light source. The light diffusion unit 1405 can effectively diffuse light from the light source to deliver the light to a wide range when used for illumination and so forth. The optical filter 1404 and the light diffusion unit 1405 may be disposed at the light emission side of the lighting apparatus. A cover may be disposed at the outermost portion, as needed.

The lighting apparatus is, for example, an apparatus that lights a room. The lighting apparatus may emit light of white, neutral white, or any color from blue to red. A light control circuit that controls the light may be provided.

The lighting apparatus may include the organic light-emitting device according to the embodiment and a power supply circuit coupled thereto. The power supply circuit is a circuit that converts an AC voltage into a DC voltage. The color temperature of white is 4,200 K, and the color temperature of neutral white is 5,000 K. The lighting apparatus may include a color filter.

The lighting apparatus according to the embodiment may include a heat dissipation unit. The heat dissipation unit is configured to release heat in the device to the outside of the device and is composed of, for example, a metal having a high specific heat and liquid silicone.

Figure 8B:
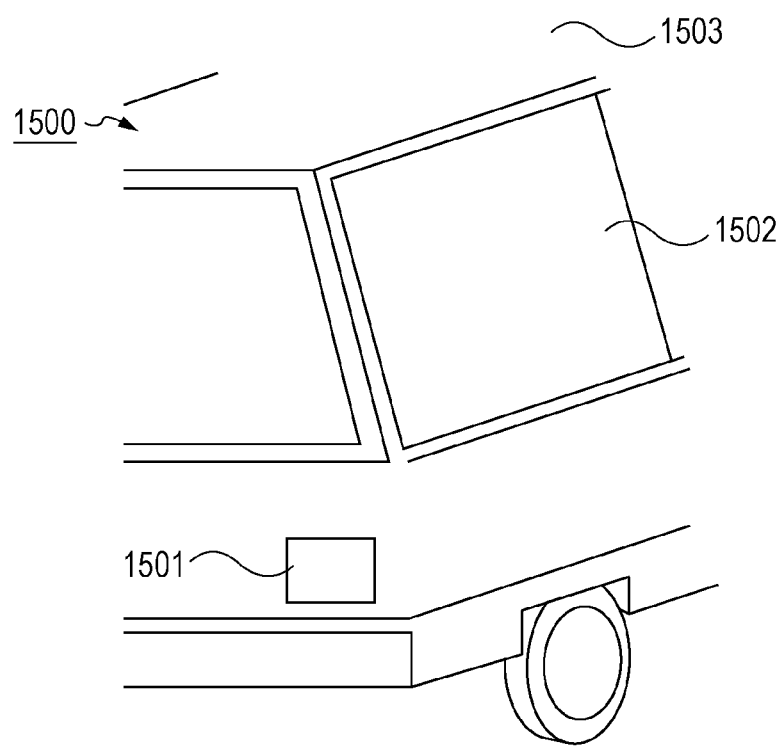
FIG. 8B is a schematic view of an example of an automobile including an automotive lighting unit according to an embodiment of the present disclosure.

FIG. 8B is a schematic view illustrating an automobile as an example of a moving object. The automobile includes a tail lamp, which is an example of lighting units. An automobile 1500 includes a tail lamp 1501 and may be configured to light the tail lamp when a brake operation or the like is performed.

The tail lamp 1501 may include an organic light-emitting device according to the embodiment. The tail lamp 1501 may include a protective member that protects the organic light-emitting device. The protective member may be composed of any transparent material having high strength to some extent and can be composed of, for example, polycarbonate. The polycarbonate may be mixed with, for example, a furandicarboxylic acid derivative or an acrylonitrile derivative.

The automobile 1500 may include an automobile body 1503 and windows 1502 attached thereto. The windows 1502 may be transparent displays if the windows are not used to check the front and back of the automobile. The transparent displays may include an organic light-emitting device according to the embodiment.

In this case, the components, such as the electrodes, of the organic light-emitting device are formed of transparent members.

The moving object according to the embodiment may be, for example, a ship, an aircraft, or a drone. The moving object may include a body and a lighting unit attached to the body. The lighting unit may emit light to indicate the position of the body. The lighting unit includes the organic light-emitting device according to the embodiment.

Examples of applications of the display apparatuses of the above embodiments will be described with reference to FIGS. 9A and 9B. The display apparatuses can be used for systems that can be worn as wearable devices, such as smart glasses, head-mounted displays (HMDs), and smart contacts. An image pickup and display apparatus used in such an example of the applications has an image pickup apparatus that can photoelectrically convert visible light and a display apparatus that can emit visible light.

Figure 9A:
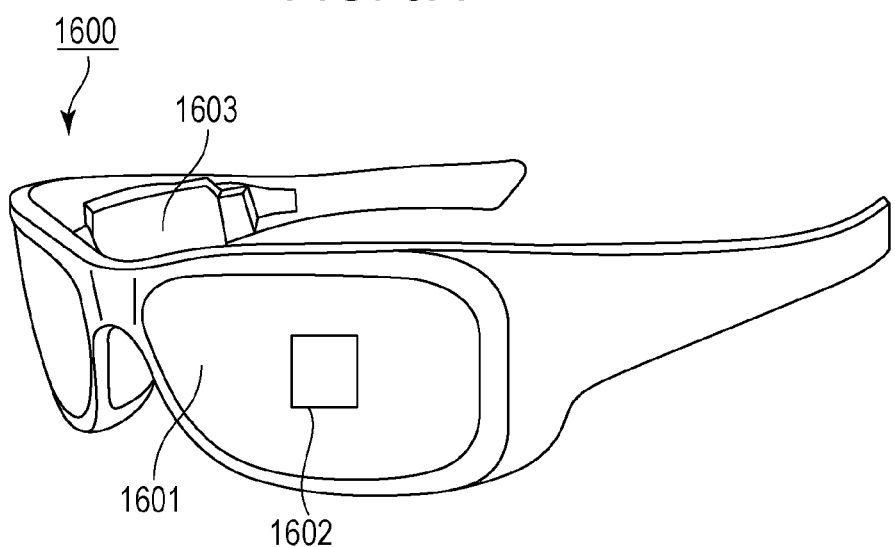
FIG. 9A is a schematic view of an example of a wearable device according to an embodiment of the present disclosure.

FIG. 9A is a schematic view illustrating an example of a wearable device according to an embodiment of the present disclosure. Glasses 1600 (smart glasses) according to an example of applications will be described with reference to FIG. 9A. An image pickup apparatus 1602, such as a complementary metal-oxide semiconductor (CMOS) sensor or a single-photon avalanche diode (SPAD), is provided on a front side of a lens 1601 of the glasses 1600. The display apparatus according to any of the above-mentioned embodiments is provided on the back side of the lens 1601.

The glasses 1600 further include a control unit 1603. The control unit 1603 functions as a power source that supplies electric power to the image pickup apparatus 1602 and the display apparatus. The control unit 1603 controls the operation of the image pickup apparatus 1602 and the display apparatus. The lens 1601 has an optical system for focusing light on the image pickup apparatus 1602.

Figure 9B:
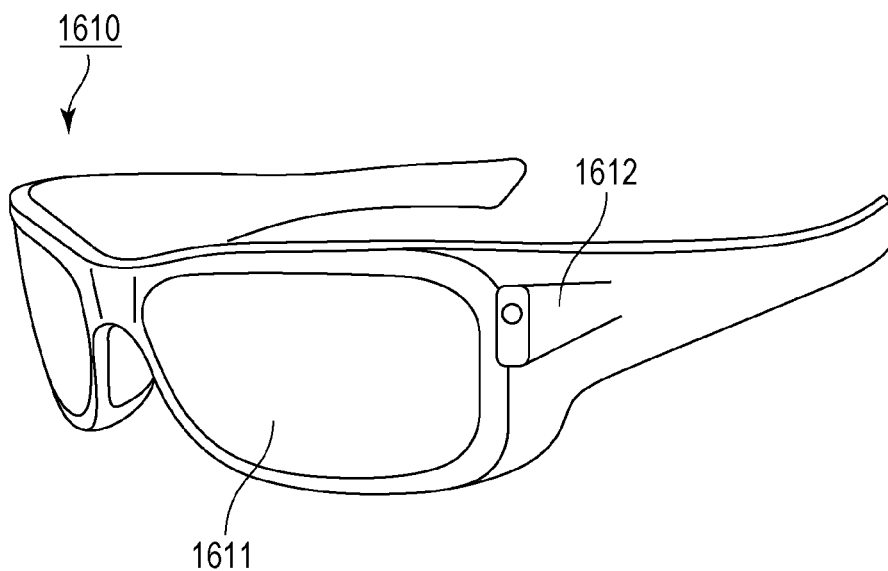
FIG. 9B is a schematic view of another example of a wearable device according to an embodiment of the present disclosure.

FIG. 9B is a schematic view illustrating another example of a wearable device according to an embodiment of the present disclosure. Glasses 1610 (smart glasses) according to an example of applications will be described with reference to FIG. 9B. The glasses 1610 include a control unit 1612. The control unit 1612 includes an image pickup apparatus corresponding to the image pickup apparatus 1602 illustrated in FIG. 9A and a display apparatus. A lens 1611 is provided with the image pickup apparatus in the control unit 1612 and an optical system that projects light emitted from the display apparatus. An image is projected onto the lens 1611. The control unit 1612 functions as a power source that supplies electric power to the image pickup apparatus and the display apparatus and controls the operation of the image pickup apparatus and the display apparatus.

The control unit 1612 may include a gaze detection unit that detects the gaze of a wearer. Infrared light may be used for gaze detection. An infrared light-emitting unit emits infrared light to an eyeball of a user who is gazing at a displayed image. An image of the eyeball is captured by detecting the reflected infrared light from the eyeball with an image pickup unit having light-receiving elements. The deterioration of image quality is reduced by providing a reduction unit that reduces light from the infrared light-emitting unit to the display unit when viewed in plan. The user's gaze at the displayed image is detected from the image of the eyeball captured with the infrared light. Any known method can be employed to the gaze detection using the captured image of the eyeball. As an example, a gaze detection method based on a Purkinje image of the reflection of irradiation light on a cornea can be employed. More specifically, the gaze detection process is based on a pupil-corneal reflection method. Using the pupil-corneal reflection method, the user's gaze is detected by calculating a gaze vector representing the direction (rotation angle) of the eyeball based on the image of the pupil and the Purkinje image contained in the captured image of the eyeball.

A display apparatus according to an embodiment of the present disclosure may include an image pickup apparatus including light-receiving elements, and may control an image displayed on the display apparatus based on the gaze information of the user from the image pickup apparatus. Specifically, in the display apparatus, a first field of view at which the user gazes and a second field of view other than the first field of view are determined on the basis of the gaze information. The first field of view and the second field of view may be determined by the control unit of the display apparatus or may be determined by receiving those determined by an external control unit. In the display area of the display apparatus, the display resolution of the first field of view may be controlled to be higher than the display resolution of the second field of view. That is, the resolution of the second field of view may be lower than that of the first field of view.

The display area includes a first display area and a second display area different from the first display area. Based on the gaze information, an area of higher priority is determined from the first display area and the second display area. The first display area and the second display area may be determined by the control unit of the display apparatus or may be determined by receiving those determined by an external control unit. The resolution of an area of higher priority may be controlled to be higher than the resolution of an area other than the area of higher priority. In other words, the resolution of an area of a relatively low priority may be low.

Artificial intelligence (AI) may be used to determine the first field of view or the high-priority area. The AI may be a model configured to estimate the angle of gaze from the image of the eyeball and the distance to a target object located in the gaze direction, using the image of the eyeball and the actual direction of gaze of the eyeball in the image as teaching data. The AI program may be stored in the display apparatus, the image pickup apparatus, or an external apparatus. When the AI program is stored in the external apparatus, the AI program is transmitted to the display apparatus via communications.

In the case of controlling the display based on visual detection, smart glasses that further include an image pickup apparatus that captures an external image can be used. The smart glasses can display the captured external information in real time.

Figure 10A:
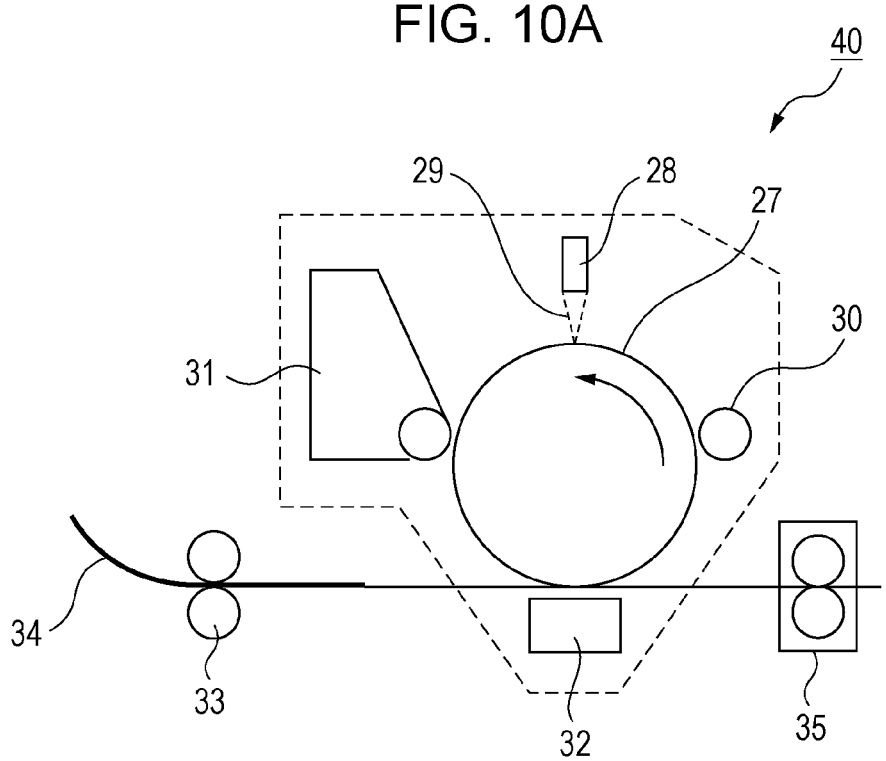
FIG. 10A is a schematic view of an example of an image-forming apparatus according to an embodiment of the present disclosure.

FIG. 10A is a schematic view of an example of an image-forming apparatus according to an embodiment of the present disclosure.

An image-forming apparatus 40 is an electrophotographic image-forming apparatus and includes a photoconductor 27, an exposure light source 28, a charging unit 30, a developing unit 31, a transfer unit 32, a transport roller 33, and a fusing unit 35. The irradiation of light 29 is performed from the exposure light source 28 to form an electrostatic latent image on the surface of the photoconductor 27. The exposure light source 28 includes the organic light-emitting device according to the embodiment. The developing unit 31 contains, for example, a toner. The charging unit 30 charges the photoconductor 27. The transfer unit 32 transfers the developed image to a recording medium 34.

The transport roller 33 transports the recording medium 34. The recording medium 34 is paper, for example. The fusing unit 35 fixes the image formed on the recording medium 34.

Figure 10B:
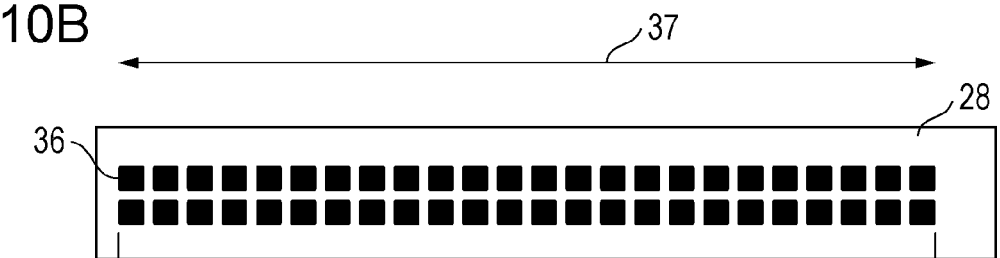
FIG. 10B is a schematic view of an example of an exposure light source of an image-forming apparatus according to an embodiment of the present disclosure.
Figure 10C:
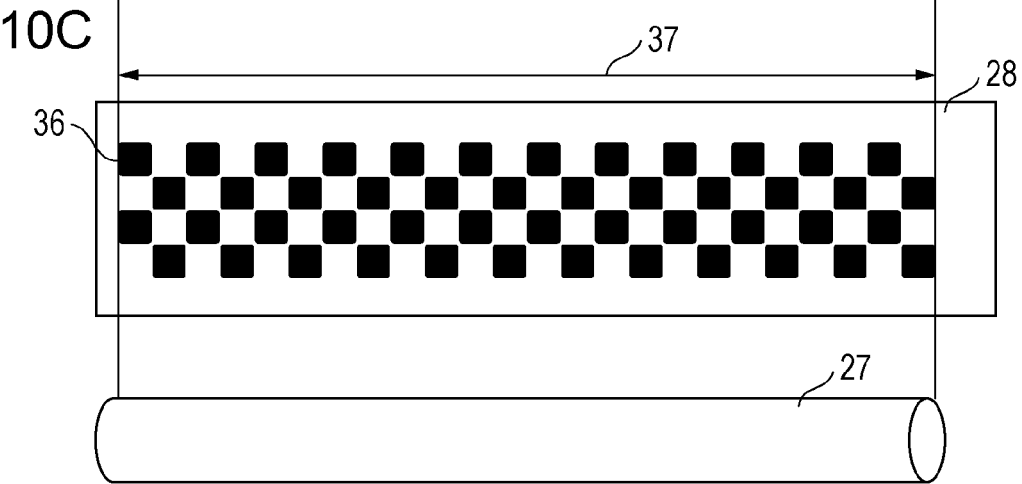
FIG. 10C is a schematic view of a modification example of an exposure light source of an image-forming apparatus according to an embodiment of the present disclosure.

FIGS. 10B and 10C each illustrate the exposure light source 28 and are each a schematic view illustrating multiple light-emitting portions 36 arranged on a long substrate. Arrows 37 are parallel to the axis of the photoconductor and are each represent the row direction in which the organic light-emitting devices are arranged. The row direction is the same as the direction of the axis on which the photoconductor 27 rotates. This direction can also be referred to as the long-axis direction of the photoconductor 27. FIG. 10B illustrates a configuration in which the light-emitting portions 36 are arranged in the long-axis direction of the photoconductor 27. FIG. 10C is different from FIG. 10B in that the light-emitting portions 36 are arranged alternately in the row direction in a first row and a second row. The first row and the second row are located at different positions in the column direction. In the first row, the multiple light-emitting portions 36 are spaced apart. The second row has the light-emitting portions 36 at positions corresponding to the positions between the light-emitting portions 36 in the first row. In other words, the multiple light-emitting portions 36 are also spaced apart in the column direction. The arrangement in FIG. 10C can be rephrased as, for example, a lattice arrangement, a staggered arrangement, or a checkered pattern.

As described above, the use of an apparatus including the organic light-emitting device according to the embodiment enables a stable display with good image quality even for a long time.

EXAMPLES

While the present disclosure will be described below by examples, the present disclosure is not limited to these examples.

Example 1: Synthesis of Exemplified Compound B-1

Exemplified compound B-1 was synthesized according to the following scheme.

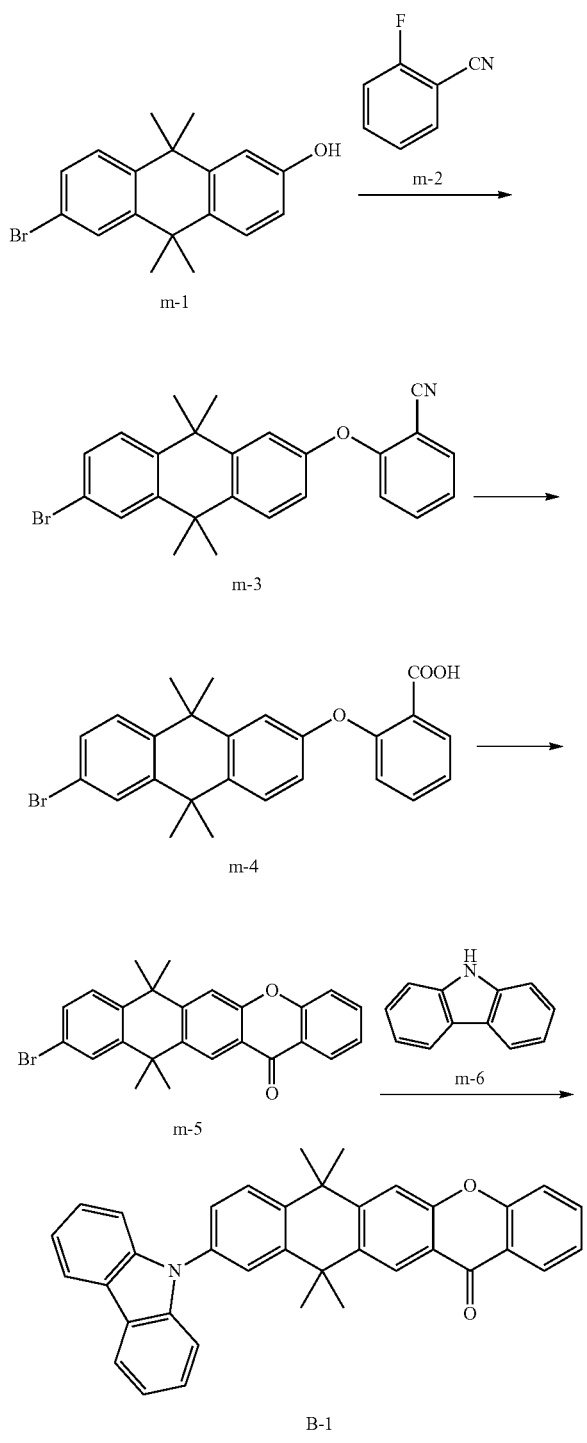

(1) Synthesis of Compound m-3

The following reagents and solvent were placed in a 100-mL recovery flask.
  Compound m-1: 1.8 g (5.4 mmol)
  Compound m-2: 0.7 g (5.7 mmol)
  Potassium carbonate: 1.1 g (8.2 mmol)
  DMF: 20 mL The reaction solution was heated and stirred at 100° C. for 7 hours under a stream of nitrogen. After the completion of the reaction, 100 mL of water was added thereto, and filtration was performed. The resulting solid was purified by silica gel column chromatography (toluene-ethyl acetate mixture) to give 1.9 g of m-3 (yield: 79%).

(2) Synthesis of Compound m-4

The following reagents and solvent were placed in a 300-mL recovery flask.
  Compound m-3: 1.8 g (4.2 mmol)
  6 M Aqueous solution of sodium hydroxide: 90 mL
  Ethanol: 90 mL The reaction solution was heated to reflux with stirring for 7 hours under a stream of nitrogen. After the completion of the reaction, concentrated hydrochloric acid was slowly added dropwise thereto at 0° C. under a stream of nitrogen to acidify the mixture. The precipitated solid was filtered. The resulting solid was dispersed and washed with 100 mL of water for 1 hour. The mixture was filtered to give 1.7 g of m-4 (yield: 93%).

(3) Synthesis of Compound m-5

The following reagent and solvent were placed in a 100-mL recovery flask.
  Compound m-4: 1.7 g (3.8 mmol)
  Sulfuric acid: 20 mL The reaction solution was stirred at 80° C. for 7 hours under a stream of nitrogen. The mixture was cooled at room temperature. The reaction mixture was poured into ice water and filtered. The resulting solid was dispersed and washed with 100 mL of water for 1 hour, and then the mixture was filtered to obtain a solid. The resulting solid was purified by silica gel column chromatography (chlorobenzene-ethyl acetate mixture) to give 1.3 g of m-5 (yield: 83%).

(4) Synthesis of Compound B-1

The following reagents and solvent were placed in a 200-mL recovery flask.
  Compound m-5: 1.3 g (3.0 mmol)
  Compound m-6: 0.6 g (3.6 mmol)
  Sodium tert-butoxide: 0.86 g (9.0 mmol)
  Pd(dba)2: 170 mg
  Xphos: 430 mg
  o-Xylene: 65 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.9 g of B-1 (yield: 58%).

Exemplified compound B-1 was subjected to mass spectrometry with MALDI-TOF-MS (Bruker Autoflex LRF).

MALDI-TOF-MS

Measured value: m/z=519

Calculated value: $C_{37}H_{29}NO_2$=519

Examples 2 to 6: Synthesis of Exemplified Compounds

As presented in Table 2, exemplified compounds of Examples 2 to 6 were synthesized as in Example 1, except that raw material m-1 of Example 1 was changed to raw material 1, raw material m-2 to raw material 2, and raw material m-6 to raw material 3. The resulting exemplified compounds were subjected to mass spectrometry as in Example 1. The measured values (m/z) are presented.

TABLE 2
| Example | Exemplified compound | Raw material 1 | Raw material 2 | Raw material 3 | m/z |
|---|---|---|---|---|---|
| 2 | B-18 | | | | 519 |
| 3 | B-2 | | | | 519 |
| 4 | B-6 | | | | 521 |
| 5 | B-17 | | | | 687 |
| 6 | B-15 | | | | 561 |
Example 7: Synthesis of Exemplified Compound D-7
Exemplified compound D-7 was synthesized according to the following scheme.
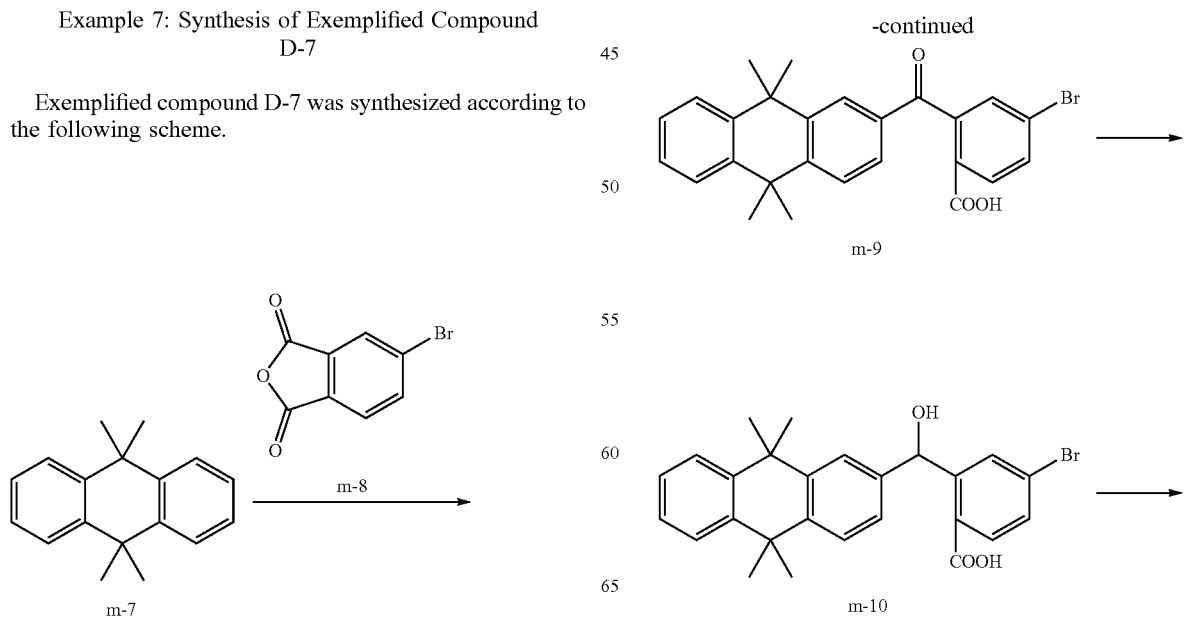

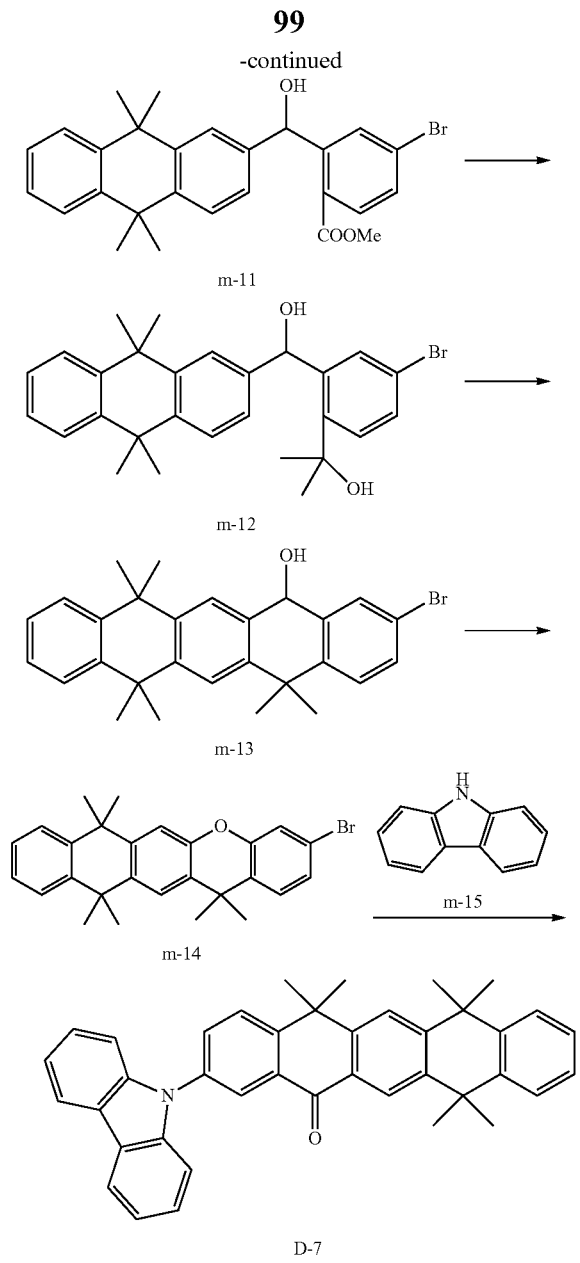

(1) Synthesis of Compound m-9

The following reagents and solvent were placed in a 2,000-mL recovery flask.

Compound m-7: 20.0 g (84.6 mmol)

Compound m-8: 21.1 g (93.1 mmol)

Methylene chloride: 1,000 mL

The reaction solution was stirred at 0° C. for 1 hour under a stream of nitrogen. Then 16.9 g of (126.9 mmol) of aluminum chloride was slowly added thereto. After that, the mixture was slowly brought to room temperature and stirred at room temperature for 8 hours. After the completion of the reaction, the reaction mixture was slowly poured into ice water, and then an extraction operation was performed. The organic layer was concentrated to dryness. The resulting solid was purified by silica gel column chromatography (toluene-ethyl acetate mixture) to give 17.6 g of compound m-9 (yield: 45%).

(2) Synthesis of Compound m-10

The following reagent and solvent were placed in a 500-mL recovery flask.

Compound m-9: 16.0 g (34.5 mmol)

Ethanol: 320 mL

The reaction solution was stirred at 0° C. for 1 hour under a stream of nitrogen, and then 1.5 g of sodium borohydride was slowly added thereto. After that, the mixture was slowly brought to room temperature and stirred at room temperature for 8 hours. After the completion of the reaction, dilute hydrochloric acid was added thereto at 0° C. to neutralize the mixture. An extraction operation was performed with methylene chloride, and then the organic layer was concentrated to dryness. The resulting solid was purified by silica gel column chromatography (toluene-ethyl acetate mixture) to give 12.9 g of m-10 (yield: 80%).

(3) Synthesis of Compound m-11

The following reagents and solvent were placed in a 200-mL recovery flask.

Compound m-10: 12.0 g (25.8 mmol)

Methanol: 360 mL

Sulfuric acid: 3.6 mL

The reaction solution was heated and stirred at 70° C. for 5 hours under a stream of nitrogen. After the completion of the reaction, the reaction mixture was slowly poured into ice water. Methylene chloride was added thereto to perform an extraction operation. The organic layer was concentrated to dryness. The resulting solid was purified by silica gel column chromatography (toluene-ethyl acetate mixture) to give 8.4 g of m-11 (yield: 68%).

(4) Synthesis of Compound m-12

The following reagent and solvent were placed in a 1,000-mL recovery flask.

Compound m-11: 8.0 g (16.7 mmol)

Tetrahydrofuran: 160 mL

The reaction solution was stirred at −10° C. for 1 hour under a stream of nitrogen, and then 27.8 mL of methylmagnesium chloride (3.0 M tetrahydrofuran solution) was slowly added thereto. The mixture was stirred for 1 hour. After that, the mixture was slowly brought to room temperature and stirred at room temperature for 3 hours. After the completion of the reaction, a saturated aqueous ammonium chloride solution was added thereto at 0° C. Methylene chloride was added thereto, and then an extraction operation was performed. The organic layer was concentrated to dryness. The resulting solid was purified by silica gel column chromatography (toluene-ethyl acetate mixture) to give 6.8 g of m-12 (yield: 85%).

(5) Synthesis of Compound m-13

The following reagent and solvent were placed in a 200-mL recovery flask.

Compound m-12: 6.0 g (12.5 mmol)

Methylene chloride: 60 mL

The reaction solution was stirred at −10° C. for 1 hour under a stream of nitrogen, and then 4.7 g of a solution containing boron tribromide and 30 mL of methylene chloride was slowly added thereto. The mixture was stirred for 1 hour. After that, the mixture was slowly brought to room temperature and stirred at room temperature for 3 hours. After the completion of the reaction, distilled water was added thereto at 0° C. Methylene chloride was added thereto, and then an extraction operation was performed. The organic layer was concentrated to dryness. The resulting solid was purified by silica gel column chromatography (toluene-ethyl acetate mixture) to give 3.9 g of m-13 (yield: 67%).

(6) Synthesis of Compound m-14

The following reagents and solvent were placed in a 200-mL recovery flask.

Compound m-13: 3.5 g (7.6 mmol)
Methylene chloride: 35 mL
Trifluoroacetic acid: 90 mL
Manganese dioxide: 730 mg The reaction solution was heated and stirred at 40° C. for 5 hours under a stream of nitrogen. After the completion of the reaction, the mixture was filtered and washed with methylene chloride. Distilled water was added to the resulting filtrate, and then an extraction operation was performed. The organic layer was concentrated to dryness. The resulting solid was purified by silica gel column chromatography (toluene-ethyl acetate mixture) to give 2.6 g of m-14 (yield: 76%).

(7) Synthesis of Compound D-7

The following reagents and solvent were placed in a 200-mL recovery flask.

Compound m-14: 1.5 g (3.0 mmol)
Compound m-15: 0.6 g (3.9 mmol)
Sodium tert-butoxide: 0.94 g (9.8 mmol)
Pd (dba) 2: 190 mg
Xphos: 470 mg
o-Xylene: 75 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 0.9 g of D-7 as a yellow solid (yield: 48%).

Exemplified compound D-7 was subjected to mass spectrometry as in Example 1.

MALDI-TOF-MS
Measured value: m/z=545
Calculated value: $C_{40}H_{36}NO=545$

Examples 8 to 11: Synthesis of Exemplified Compounds

As presented in Table 3, exemplified compounds of Examples 8 to 11 were synthesized as in Example 7, except that raw material m-7 of Example 7 was changed to raw material 1, raw material m-8 to raw material 2, and raw material m-15 to raw material 3. In the step (4) of Example 11, phenylmagnesium bromide was used as the Grignard reagent in place of methylmagnesium chloride. The resulting exemplified compounds were subjected to mass spectrometry as in Example 7. The measured values (m/z) are presented.

TABLE 3

| Example | Exemplified compound | Raw material 1 | Raw material 2 | Raw material 3 | m/z |
|---|---|---|---|---|---|
| 8 | D-11 | [structure] | [structure] | [structure] | 547 |
| 9 | D-1 | [structure] | [structure] | [structure] | 545 |
| 10 | D-21 | [structure] | [structure] | [structure] | 661 |
| 11 | D-13 | [structure] | [structure] | [structure] | 669 |

Example 12: Synthesis of Exemplified Compound C-17

Exemplified compound C-17 was synthesized according to the following scheme.

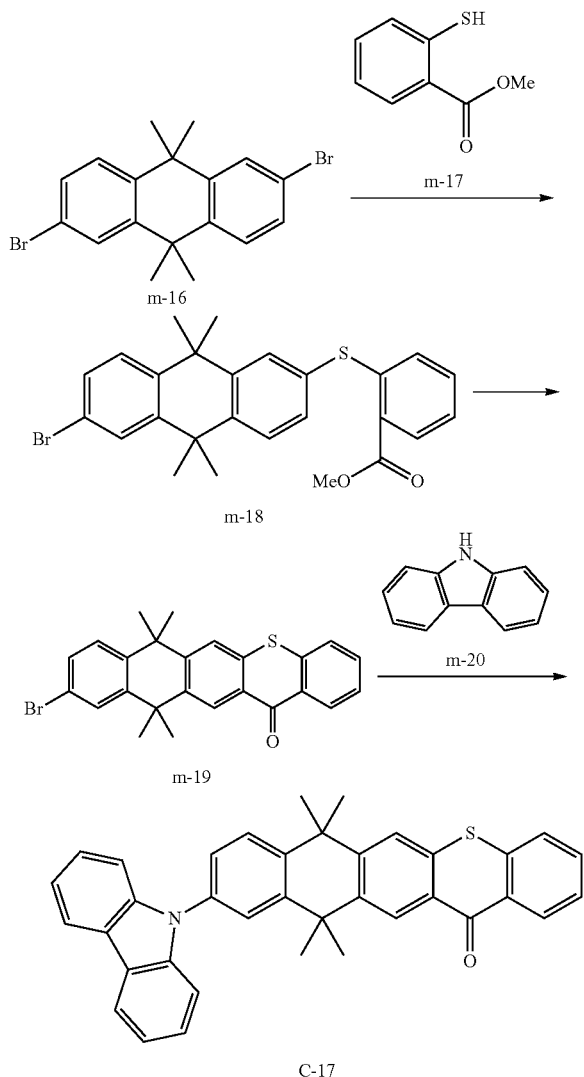

(1) Synthesis of Compound m-18

The following reagents and solvent were placed in a 500-mL recovery flask.
Compound m-16: 5.0 g (12.7 mmol)
Cesium carbonate: 5.0 g (10.1 mmol)
DMF: 150 mL The reaction solution was stirred at 70° C. for 1 hour under a stream of nitrogen. To this reaction solution, a mixture of 1.7 g of m-17 in 150 mL of DMF was slowly added dropwise. The mixture was stirred for another 1 hour. The mixture was cooled to room temperature. Ethyl acetate and distilled water were added thereto, and then an extraction operation was performed. The resulting organic layer was concentrated to dryness. The resulting solid was purified by silica gel column chromatography (toluene-heptane mixture) to give 3.2 g of m-18 (yield: 52%).

(2) Synthesis of Compound m-19

The following reagent and solvent were placed in a 100-mL recovery flask.
Compound m-18: 3.0 g (6.2 mmol)
Sulfuric acid: 30 mL The reaction solution was stirred at 80° C. for 7 hours under a stream of nitrogen. Then the mixture was cooled at room temperature. The reaction mixture was poured into ice water and filtered. The resulting solid was dispersed and washed with 100 mL of water for 1 hour. The mixture was filtered to obtain a solid. The resulting solid was purified by silica gel column chromatography (chlorobenzene-ethyl acetate mixture) to give 1.9 g of m-19 (yield: 70%).

(3) Synthesis of Compound C-17

The following reagents and solvent were placed in a 200-mL recovery flask.
Compound m-19: 1.5 g (3.0 mmol)
Compound m-20: 0.7 g (3.6 mmol)
Sodium tert-butoxide: 0.96 g (9.0 mmol)
Pd(dba)$_2$: 190 mg
Xphos: 480 mg
o-Xylene: 75 mL The reaction solution was heated and stirred at 140° C. for 5 hours under a stream of nitrogen. After the completion of the reaction, filtration was performed through Celite, and then the filtrate was concentrated to dryness. The resulting solid was purified by silica gel column chromatography (toluene-ethyl acetate mixture) to give 1.1 g of C-17 (yield: 62%).

Exemplified compound C-17 was subjected to mass spectrometry as in Example 1.
MALDI-TOF-MS
Measured value: m/z=535
Calculated value: $C_{37}H_{29}NOS$=535

Examples 13 and 14: Synthesis of Exemplified Compounds

As presented in Table 4, exemplified compounds of Examples 13 and 14 were synthesized as in Example 12, except that raw material m-16 of Example 12 was changed to raw material 1, raw material m-17 to raw material 2, and raw material m-20 to raw material 3. The resulting exemplified compounds were subjected to mass spectrometry as in Example 12. The measured values (m/z) are presented.

TABLE 4

| Example | Exemplified compound | Raw material 1 | Raw material 2 | Raw material 3 | m/z |
|---|---|---|---|---|---|
| 13 | C-4 | | | | 577 |

TABLE 4-continued

| Example | Exemplified compound | Raw material 1 | Raw material 2 | Raw material 3 | m/z |
|---|---|---|---|---|---|
| 14 | C-9 | (dibromo dimethyl dihydroanthracene structure) | 2-mercapto methyl benzoate (SH, OMe, O) | N-phenyl indolocarbazole structure | 700 |

Example 15

In this Example, an organic light-emitting device having a bottom-emission structure was produced in which an anode, a hole injection layer, a hole transport layer, an electron-blocking layer, a light-emitting layer, a hole-blocking layer, an electron transport layer, an electron injection layer, and a cathode were sequentially formed on a substrate.

An ITO film was formed on a glass substrate and subjected to desired patterning to form an ITO electrode (anode). The ITO electrode had a thickness of 100 nm. The substrate on which the ITO electrode had been formed in this way was used as an ITO substrate in the following steps. Next, vacuum evaporation was performed by resistance heating in a vacuum chamber to continuously form organic compound layers and an electrode layer presented in Table 5 on the ITO substrate. Here, the opposing electrode (metal electrode layer, cathode) had an electrode area of 3 mm². The "percentage (%)" in Table 5 is percentage by mass.

The characteristics of the resulting device were measured and evaluated. As the initial characteristics associated with the light emission, green light emission with a maximum external quantum efficiency (E.Q.E.) of 5.6% was obtained. With regard to measurement instruments, specifically, the current-voltage characteristics were measured with a Hewlett-Packard 4140B microammeter, and the luminance was measured with a Topcon BM7. The device was subjected to a continuous operation test at a current density of 50 mA/cm². The time when the percentage of luminance degradation reached 5% (LT95) was measured to be 110 hours.

Examples 16 to 20

Organic light-emitting devices were produced in the same manner as in Example 15, except that the compounds used in Example 15 were changed to compounds listed in Table 6 as appropriate. The characteristics of the resulting device were measured and evaluated as in Example 15. Table 6 presents the measurement results.

TABLE 6

|  | HTL | EBL | EML Host | EML Light-emitting material | HBL | ETL | E.Q.E [%] | LT95 [h] | Emission color |
|---|---|---|---|---|---|---|---|---|---|
| Example 16 | HT3 | HT12 | EM11 | B-2 | ET12 | ET2 | 5.2 | 100 | green |
| Example 17 | HT3 | HT11 | EM10 | B-6 | ET12 | ET2 | 5.6 | 89 | green |
| Example 18 | HT3 | HT12 | EM11 | C-4 | ET12 | ET2 | 5.5 | 105 | green |
| Example 19 | HT2 | HT11 | EM14 | D-1 | ET12 | ET2 | 5.6 | 95 | green |
| Example 20 | HT2 | HT10 | EM32 | D-7 | ET12 | ET5 | 5.6 | 75 | green |

TABLE 5

|  |  | Material | Thickness (nm) |
|---|---|---|---|
| Cathode |  | Al | 100 |
| Electron injection layer (EIL) |  | LiF | 1 |
| Electron transport layer (ETL) |  | ET2 | 15 |
| Hole-blocking layer (HBL) |  | ET11 | 15 |
| Light-emitting layer (EML) | host | light-emitting material | 20 |
|  | EM11 | B-1 |  |
| Light-emitting layer, percentage (%) | 88 | 12 |  |
| Electron-blocking layer (EBL) |  | HT12 | 15 |
| Hole transport layer (HTL) |  | HT2 | 30 |
| Hole injection layer (HIL) |  | HT16 | 5 |

Example 21

An organic light-emitting device was produced in the same manner as in Example 15, except that the organic compound layers and the electrode layer listed in Table 7 were continuously deposited. The "percentage (%)" in Table 7 is percentage by mass.

TABLE 7

|  | Material | Thickness (nm) |
|---|---|---|
| Cathode | Al | 100 |
| Electron injection layer (EIL) | LiF | 1 |
| Electron transport layer (ETL) | ET2 | 15 |
| Hole-blocking layer (HBL) | ET11 | 15 |

TABLE 7-continued

|  | Material | | | Thickness (nm) |
| --- | --- | --- | --- | --- |
| Light-emitting layer (EML) | host | assist material | light-emitting material | 20 |
|  | EM11 | B-1 | GD5 |  |
| Light-emitting layer, percentage (%) | 82 | 15 | 3 |  |
| Electron-blocking layer (EBL) | HT7 | | | 15 |
| Hole transport layer (HTL) | HT3 | | | 30 |
| Hole injection layer (HIL) | HT16 | | | 5 |

The characteristics of the resulting device were measured and evaluated as in Example 15. As the initial characteristics associated with the light emission, green light emission with a maximum external quantum efficiency (E.Q.E.) of 6.4% was obtained. The device was subjected to a continuous operation test at a current density of 50 mA/cm$^2$. The time when the percentage of luminance degradation reached 5% (LT95) was measured to be 143 hours.

Examples 22 to 39 and Comparative Examples 1 and 2

Organic light-emitting devices were produced in the same manner as in Example 21, except that the compounds used in Example 21 were changed to compounds listed in Table 8 as appropriate. The characteristics of the resulting devices were measured and evaluated as in Example 21. Table 8 presents the measurement results. Comparative compound 1 is comparative compound 1 described in FIG. 1. Comparative example 2 is comparative compound 2 described in Table 1 and FIG. 2.

Table 8 indicates that the maximum external quantum efficiency (E.Q.E.) in Comparative example 1 was as low as 4.0 or less. The reason for this is that the large difference between $S_1$ and $T_1$ of comparative compound 1 results in the absence of an emission component based on delayed fluorescence. In contrast, the devices of Examples 22 to 39 exhibited high luminous efficiency. This is due to the fact that each of the compounds according to the embodiment had a structure in which an electron-withdrawing carbonyl group was bonded while incorporated into a ring structure and an electron-donating amino group was contained, and thus was able to use delayed fluorescence owing to the small difference between $S_1$ and $T_1$. The 5% degradation lifetime (LT95) in Comparative example 2 was 50 hours, indicating poor durability characteristics. This is presumably due to the shallow HOMO energy level (close to the vacuum level) and low oxidation stability of comparative compound 2. In contrast, the 5% degradation lifetime of each of the devices in Examples 22 to 39 was more than 100 hours, indicating good durability characteristics. This is presumably due to the deep HOMO energy level (far from the vacuum level) and high oxidation stability of each of the compounds according to the embodiment, which resulted in good durability characteristics.

The organic compounds according to embodiments of the present disclosure have superior chemical stability and light emission characteristics. Thus, when the organic compounds according to embodiments of the present disclosure are used in organic light-emitting devices, it is possible to provide the organic light-emitting devices having superior luminous efficiency and driving durability characteristics.

While the present disclosure has been described with reference to exemplary embodiments, it is to be understood

TABLE 8

|  | | | | EML | | | | | | |
| --- | --- | --- | --- | --- | --- | --- | --- | --- | --- | --- |
|  | HTL | EBL | Host | Assist | Light-emitting material | HBL | ETL | E.Q.E [%] | L195 [h] | Emission color |
| Example 22 | HT3 | HT12 | EM11 | B-15 | GD5 | ET12 | ET2 | 6.4 | 154 | green |
| Example 23 | HT3 | HT11 | EM11 | B-17 | GD5 | ET12 | ET2 | 6.4 | 150 | green |
| Example 24 | HT3 | HT12 | EM11 | C-11 | GD6 | ET12 | ET2 | 6.5 | 152 | green |
| Example 25 | HT2 | HT11 | EM14 | C-5 | GD6 | ET12 | ET2 | 6.5 | 157 | green |
| Example 26 | HT2 | HT10 | EM14 | C-17 | GD6 | ET12 | ET5 | 6.6 | 156 | green |
| Example 27 | HT3 | HT11 | EM14 | B-2 | GD5 | ET12 | ET2 | 6.0 | 130 | green |
| Example 28 | HT3 | HT12 | EM14 | D-11 | GD5 | ET11 | ET2 | 6.3 | 110 | green |
| Example 29 | HT3 | HT11 | EM14 | D-1 | GD1 | ET12 | ET2 | 6.4 | 101 | green |
| Example 30 | HT3 | HT12 | EM33 | C-20 | GD7 | ET11 | ET2 | 6.2 | 95 | green |
| Example 31 | HT2 | HT12 | EM13 | C-9 | GD9 | ET12 | ET2 | 5.8 | 153 | green |
| Example 32 | HT2 | HT12 | EM9 | B-18 | RD1 | ET12 | ET2 | 6.2 | 171 | red |
| Example 33 | HT3 | HT10 | EM9 | C-11 | RD1 | ET12 | ET2 | 6.1 | 174 | red |
| Example 34 | HT2 | HT12 | EM9 | B-10 | RD1 | ET11 | ET5 | 5.9 | 142 | red |
| Example 35 | HT3 | HT10 | EM9 | D-26 | RD1 | ET12 | ET2 | 5.2 | 125 | red |
| Example 36 | HT2 | HT12 | EM9 | B-5 | RD1 | ET11 | ET5 | 5.2 | 135 | red |
| Example 37 | HT3 | HT11 | EM11 | C-7 | RD2 | ET11 | ET2 | 5.9 | 159 | red |
| Example 38 | HT3 | HT12 | EM11 | D-21 | RD2 | ET12 | ET2 | 6.5 | 130 | red |
| Example 39 | HT3 | HT11 | EM32 | B-3 | RD2 | ET12 | ET2 | 6.3 | 105 | red |
| Comparative example 1 | HT3 | HT11 | EM14 | comparative compound 1 | GD5 | ET12 | ET2 | 3.5 | 80 | green |
| Comparative example 2 | HT3 | HT12 | EM14 | comparative compound 2 | RD1 | ET12 | ET2 | 4.5 | 50 | red | that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-018706 filed Feb. 9, 2021, which is hereby incorporated by reference herein in its entirety.

What is claimed is:

1. An organic compound represented by formula [1]:

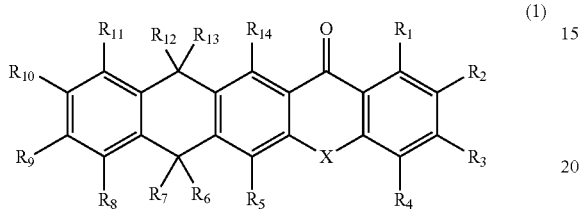

where in formula [1], $R_1$ to $R_{14}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group, $R_6$ and $R_7$ are optionally taken together to form a ring structure, $R_{12}$ and $R_{13}$ are optionally taken together to form a ring structure, wherein at least one of $R_1$ to $R_4$ and $R_8$ to $R_{11}$ is a substituted or unsubstituted amino group or a group containing a substituted or unsubstituted amino group, and groups bonded to a nitrogen atom of a substituted or unsubstituted amino group are optionally taken together to form a ring structure, and X is oxygen, sulfur, selenium, tellurium, or a $CR_{15}R_{16}$ group, wherein $R_{15}$ and $R_{16}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted heteroaryloxy group, a silyl group, and a cyano group.

2. The organic compound according to claim 1, wherein each of $R_6$, $R_7$, $R_{12}$, and $R_{13}$ is not a hydrogen atom.

3. The organic compound according to claim 1, wherein at least one of $R_8$ to $R_{11}$ is a substituted or unsubstituted amino group or a group containing a substituted or unsubstituted amino group.

4. The organic compound according to claim 3, wherein at least one of $R_8$ to $R_{11}$ is a substituted or unsubstituted amino group.

5. The organic compound according to claim 1, wherein at least one of $R_8$ to $R_{11}$ is an amino group having any of structures:

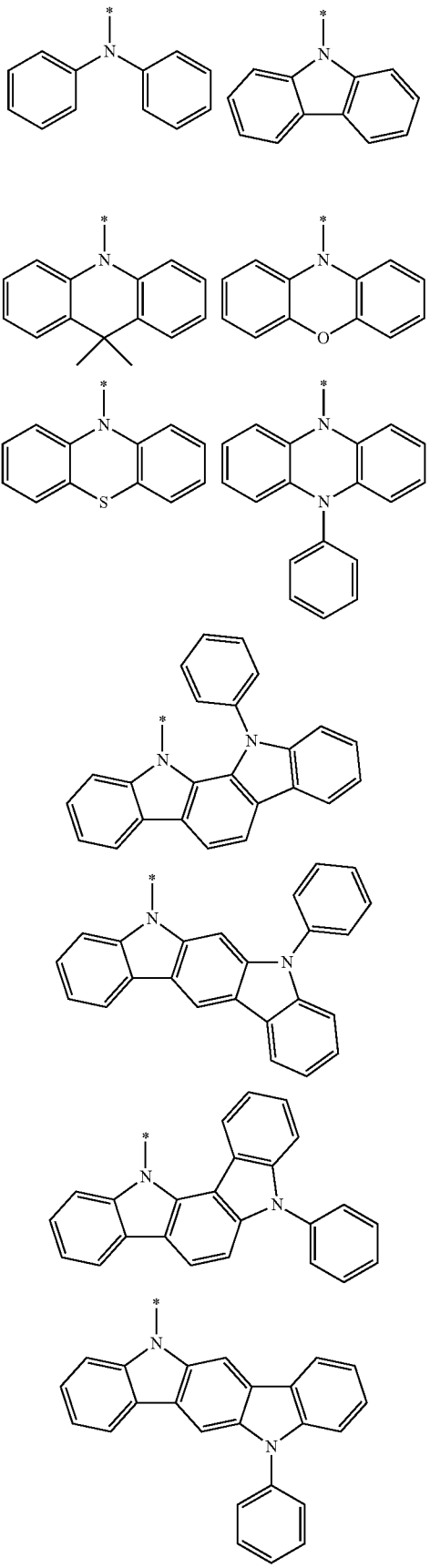

111
-continued
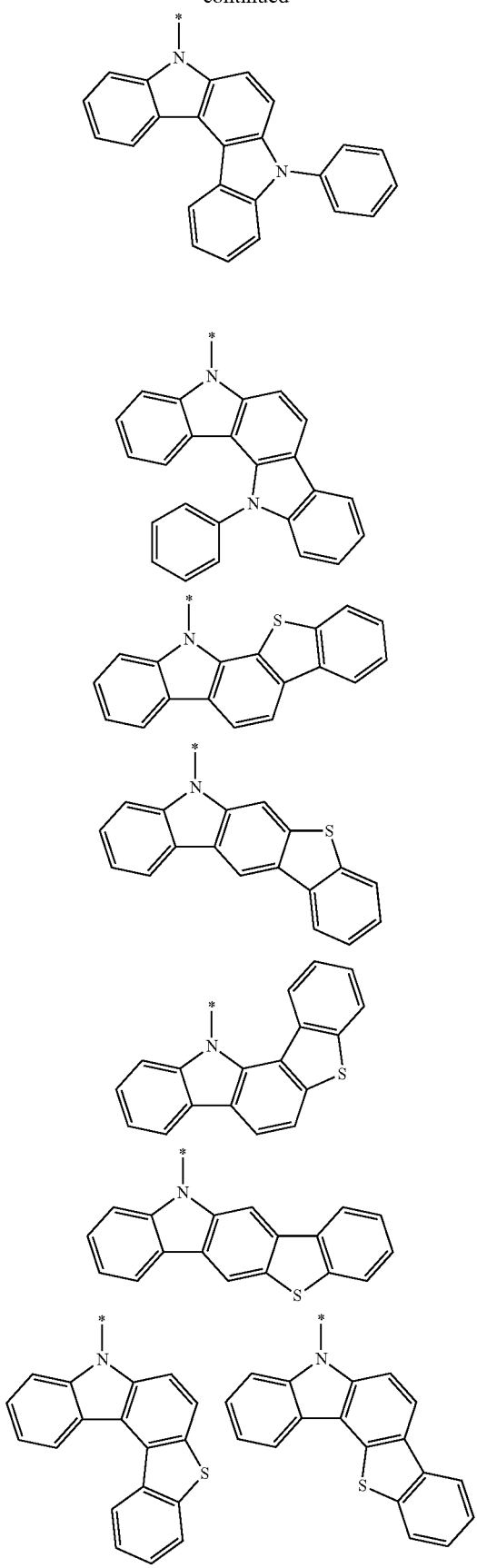
112
-continued
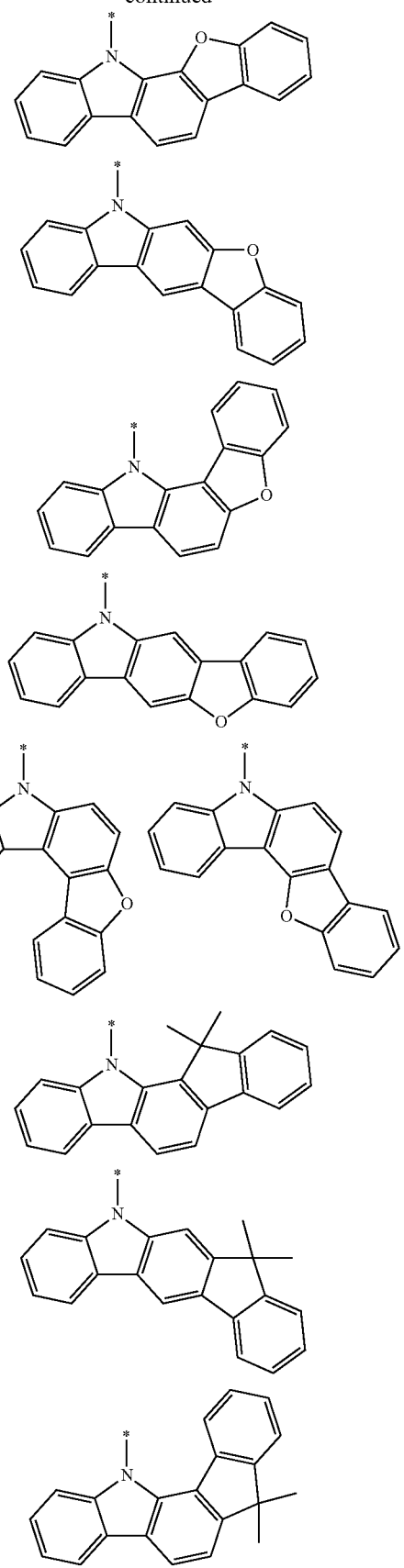

-continued
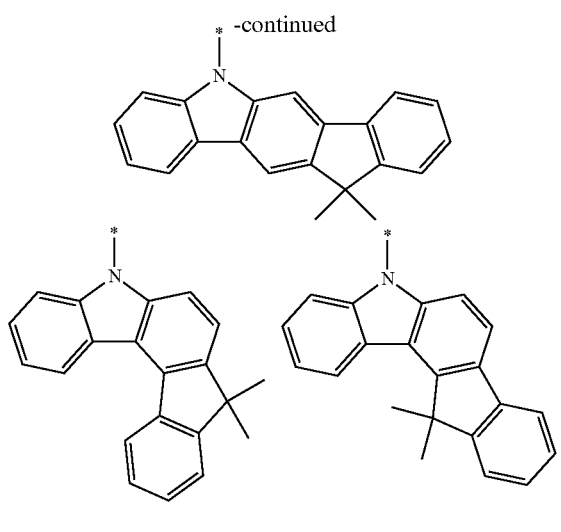
where each * represents a binding position.
6. The organic compound according to claim 5, wherein at least one of $R_8$ to $R_{11}$ is an amino group having any of structures:
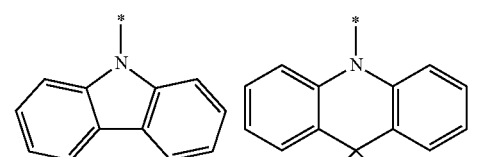
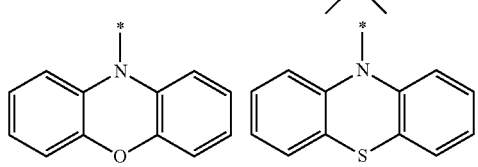
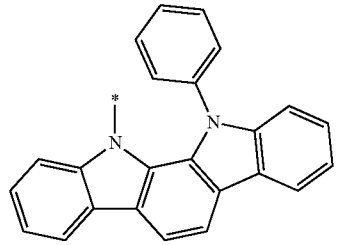
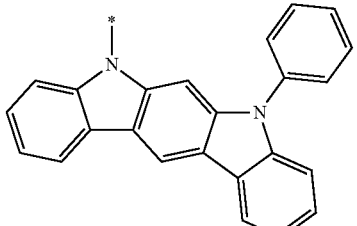
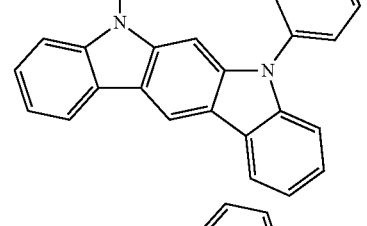
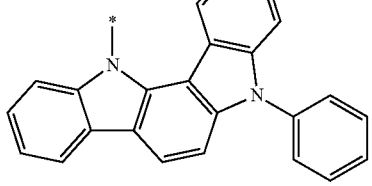
-continued
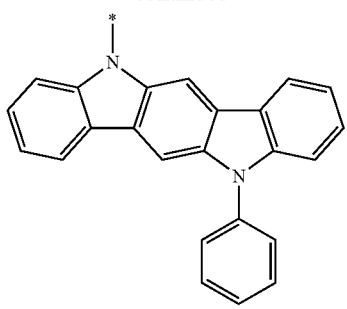
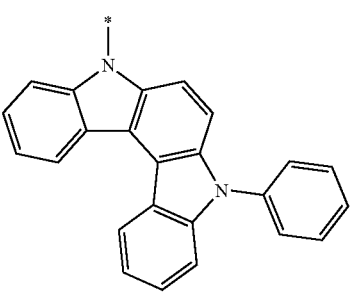
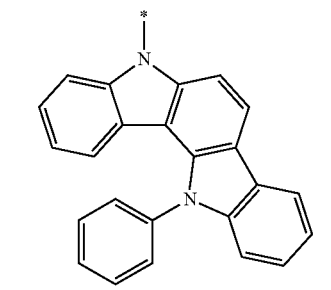
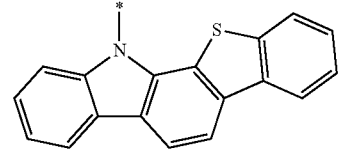
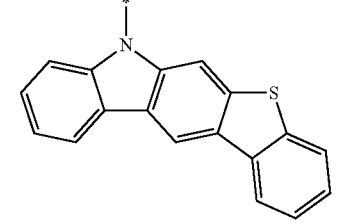
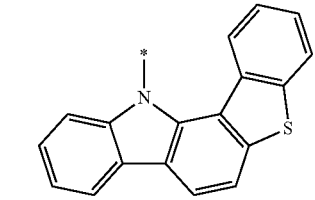
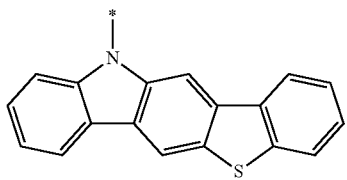

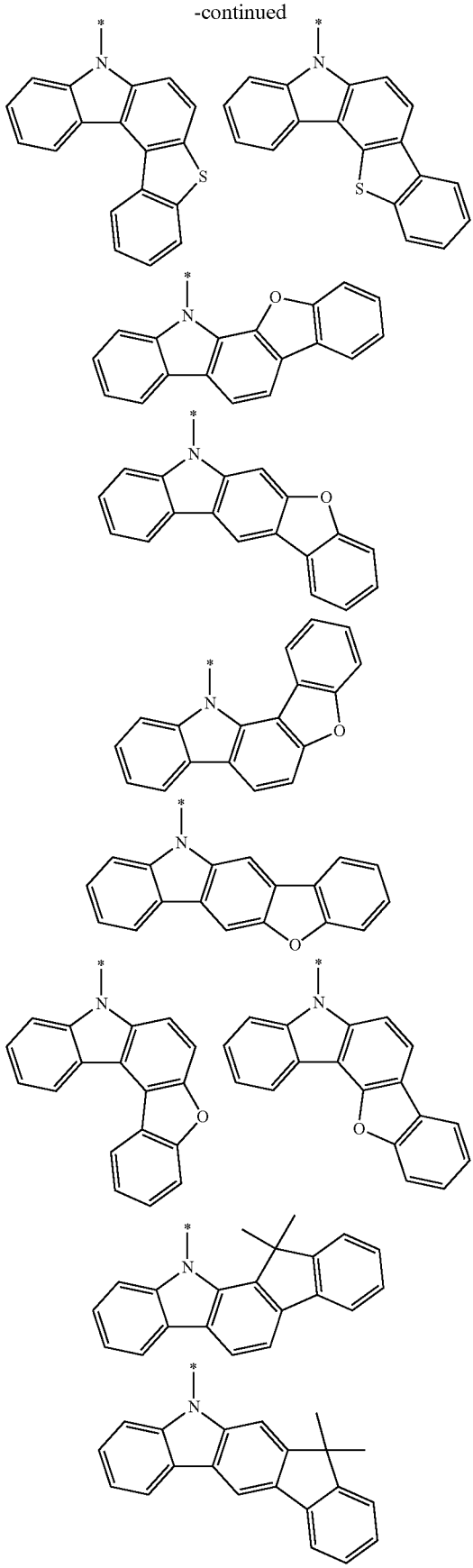

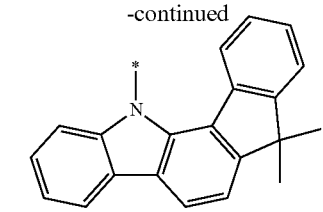

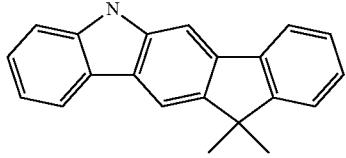

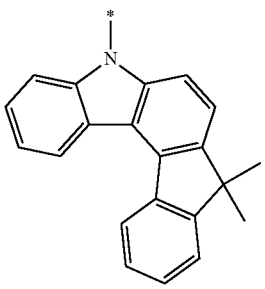 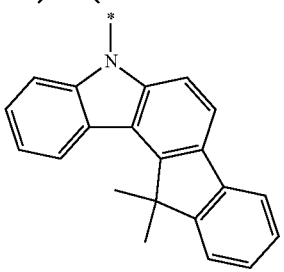

where each * represents a binding position.

7. The organic compound according to claim 1, wherein X is selected from oxygen and sulfur.

8. The organic compound according to claim 1, wherein $R_1$ to $R_5$ and $R_{14}$ are each independently selected from the group consisting of a hydrogen atom, a substituted or unsubstituted alkyl group, a phenyl group, a biphenyl group, a naphthyl group, a pyridyl group, a pyrazinyl group, a triazinyl group, fluorine, or a cyano group.

9. An organic light-emitting device, comprising:
an anode;
a cathode; and
at least one organic compound layer disposed between the anode and the cathode,
wherein at least one layer of the at least one organic compound layer contains the organic compound according to claim 1.

10. The organic light-emitting device according to claim 9, wherein the at least one layer containing the organic compound is a light-emitting layer.

11. The organic light-emitting device according to claim 10, wherein the light-emitting layer further contains a host material.

12. The organic light-emitting device according to claim 11, wherein the host material is a hydrocarbon compound.

13. The organic light-emitting device according to claim 11, wherein the light-emitting layer further contains a light-emitting material.

14. The organic light-emitting device according to claim 13, wherein the light-emitting material is a hydrocarbon compound.

15. The organic light-emitting device according to claim 10, wherein the light-emitting layer emits green light or red light.

16. A display apparatus, comprising:
multiple pixels,
at least one of the multiple pixels including:
the organic light-emitting device according to claim 9, and an active element coupled to the organic light-emitting device.

17. A photoelectric conversion apparatus, comprising:
an optical unit including multiple lenses;
an image pickup device configured to receive light passing through the optical unit; and
a display unit configured to display an image captured by the image pickup device,
wherein the display unit includes the organic light-emitting device according to claim 9.

18. An electronic apparatus, comprising:
a display unit including the organic light-emitting device according to claim 9;
a housing provided with the display unit; and
a communication unit being disposed in the housing and communicating with an outside.

19. A lighting apparatus, comprising:
a light source including the organic light-emitting device according to claim 9; and
a light diffusion unit or an optical filter configured to transmit light emitted from the light source.

20. A moving object, comprising:
a lighting unit including the organic light-emitting device according to claim 9; and
a body provided with the lighting unit.

21. An exposure light source for an electrophotographic image-forming apparatus, comprising:
the organic light-emitting device according to claim 9.

* * * * *